US008043362B2

(12) United States Patent
Gong et al.

(10) Patent No.: US 8,043,362 B2
(45) Date of Patent: Oct. 25, 2011

(54) APPARATUS AND METHODS FOR USE OF EXPANDABLE MEMBERS IN SURGICAL APPLICATIONS

(75) Inventors: Gorman Gong, Santa Clara, CA (US); Bryan J. Auyoung, Santa Clara, CA (US); Nishith Chasmawala, San Francisco, CA (US); Alex Hsia, San Jose, CA (US); Reynaldo A. Osorio, Daly City, CA (US); Christopher U. Phan, San Leandro, CA (US); Warren Sapida, Santa Clara, CA (US)

(73) Assignee: Kyphon SARL, Neuchatel (CH)

( * ) Notice: Subject to any disclaimer, the term of this patent is extended or adjusted under 35 U.S.C. 154(b) by 1243 days.

(21) Appl. No.: 11/730,348

(22) Filed: Mar. 30, 2007

(65) Prior Publication Data

US 2008/0051820 A1 Feb. 28, 2008

Related U.S. Application Data

(60) Provisional application No. 60/884,050, filed on Jan. 9, 2007, provisional application No. 60/823,566, filed on Aug. 25, 2006.

(51) Int. Cl.
*A61F 2/06* (2006.01)
(52) U.S. Cl. ...................................... 623/1.23
(58) Field of Classification Search ................. 623/1.23; 606/153, 200
See application file for complete search history.

(56) References Cited

U.S. PATENT DOCUMENTS

| 4,083,369 | A |   | 4/1978  | Sinnreich |
|-----------|---|---|---------|-----------|
| 4,261,339 | A | * | 4/1981  | Hanson et al. .................. 600/18 |
| 4,313,434 | A |   | 2/1982  | Segal |
| 4,327,736 | A |   | 5/1982  | Inoue |
| 4,338,942 | A | * | 7/1982  | Fogarty ......................... 606/194 |
| 4,346,698 | A | * | 8/1982  | Hanson et al. .................. 600/18 |
| 4,362,150 | A | * | 12/1982 | Lombardi et al. .............. 600/18 |
| 4,395,806 | A | * | 8/1983  | Wonder et al. ........... 29/890.122 |
| 4,402,307 | A | * | 9/1983  | Hanson et al. .................. 600/18 |
| 4,403,612 | A | * | 9/1983  | Fogarty ......................... 606/194 |

(Continued)

FOREIGN PATENT DOCUMENTS
JP          8038618          2/1996
(Continued)

OTHER PUBLICATIONS

International Search Report for PCT/US07/76639 mailed Apr. 29, 2008.

*Primary Examiner* — Darwin Erezo
*Assistant Examiner* — Son Dang
(74) *Attorney, Agent, or Firm* — Haynes and Boone, LLP

(57) ABSTRACT

An apparatus includes an expandable member and an elongate assembly. The expandable member is configured to displace a first portion of a bone structure relative to a second portion of the bone structure when moved from a collapsed configuration to an expanded configuration. The elongate assembly includes a shaft and an elongated member disposed with a lumen defined by the shaft. A proximal end portion of the expandable member is coupled to a distal end portion of the shaft such that the proximal end portion of the expandable member does not rotate relative to the distal end portion of the shaft when at least a portion of the expandable member is twisted about the elongated member through at least four revolutions.

24 Claims, 25 Drawing Sheets

U.S. PATENT DOCUMENTS

| | | | |
|---|---|---|---|
| 4,422,447 A * | 12/1983 | Schiff | 600/18 |
| 4,444,186 A * | 4/1984 | Wolvek et al. | 606/194 |
| 4,467,790 A | 8/1984 | Schiff | |
| 4,483,340 A | 11/1984 | Fogarty | |
| 4,531,512 A | 7/1985 | Wolvek et al. | |
| 4,608,984 A * | 9/1986 | Fogarty | 606/194 |
| 4,619,263 A | 10/1986 | Frisbie et al. | |
| 4,820,349 A | 4/1989 | Saab | |
| 4,885,003 A | 12/1989 | Hillstead | |
| 4,886,506 A | 12/1989 | Lovgren et al. | |
| 4,906,244 A | 3/1990 | Pinchuk et al. | |
| 4,909,789 A | 3/1990 | Taguchi et al. | |
| 4,938,676 A | 7/1990 | Jackowski et al. | |
| 4,955,895 A * | 9/1990 | Sugiyama et al. | 606/194 |
| 4,969,888 A | 11/1990 | Scholten et al. | |
| 4,981,478 A * | 1/1991 | Evard et al. | 604/527 |
| 5,034,001 A | 7/1991 | Garrison et al. | |
| 5,035,694 A * | 7/1991 | Kasprzyk et al. | 606/27 |
| 5,037,392 A | 8/1991 | Hillstead | |
| 5,049,132 A | 9/1991 | Shaffer et al. | |
| 5,087,246 A | 2/1992 | Smith | |
| 5,102,390 A | 4/1992 | Crittenden et al. | |
| 5,104,376 A | 4/1992 | Crittenden et al. | |
| 5,108,404 A | 4/1992 | Scholten et al. | |
| 5,114,423 A * | 5/1992 | Kasprzyk et al. | 606/27 |
| 5,116,305 A | 5/1992 | Milder et al. | |
| 5,213,576 A | 5/1993 | Abiuso et al. | |
| 5,254,090 A | 10/1993 | Lombardi et al. | |
| 5,254,091 A | 10/1993 | Aliahmad | |
| 5,304,134 A * | 4/1994 | Kraus et al. | 604/96.01 |
| 5,304,135 A | 4/1994 | Shonk | |
| 5,306,246 A | 4/1994 | Sahatjian et al. | |
| 5,318,531 A | 6/1994 | Leone | |
| 5,328,468 A | 7/1994 | Kaneko et al. | |
| 5,338,301 A | 8/1994 | Diaz | |
| 5,348,017 A | 9/1994 | Thornton et al. | |
| 5,356,591 A | 10/1994 | Pinchuk et al. | |
| 5,358,486 A | 10/1994 | Saab | |
| 5,364,352 A | 11/1994 | Cimino et al. | |
| 5,397,306 A | 3/1995 | Nobuyoshi et al. | |
| 5,405,472 A | 4/1995 | Leone | |
| 5,411,477 A | 5/1995 | Saab | |
| 5,417,707 A | 5/1995 | Parkola | |
| 5,423,754 A * | 6/1995 | Cornelius et al. | 604/103 |
| 5,425,710 A | 6/1995 | Khair et al. | |
| 5,439,447 A | 8/1995 | Miraki | |
| 5,443,477 A | 8/1995 | Marin et al. | |
| 5,447,497 A | 9/1995 | Sogard et al. | |
| 5,454,365 A | 10/1995 | Bonutti | |
| 5,499,973 A | 3/1996 | Saab | |
| 5,501,759 A | 3/1996 | Forman | |
| 5,533,968 A | 7/1996 | Muni et al. | |
| 5,549,552 A * | 8/1996 | Peters et al. | 604/103.1 |
| 5,643,279 A | 7/1997 | Trotta | |
| 5,653,691 A * | 8/1997 | Rupp et al. | 604/103.06 |
| 5,676,659 A | 10/1997 | McGurk | |
| 5,681,344 A | 10/1997 | Kelly | |
| 5,681,522 A | 10/1997 | Roychowdhury | |
| 5,702,410 A | 12/1997 | Klunder et al. | |
| 5,728,063 A | 3/1998 | Preissman et al. | |
| 5,759,173 A | 6/1998 | Preissman et al. | |
| 5,759,191 A | 6/1998 | Barbere | |
| 5,797,877 A | 8/1998 | Hamilton et al. | |
| 5,820,594 A | 10/1998 | Fontirroche et al. | |
| 5,824,173 A | 10/1998 | Fontirroche et al. | |
| 5,827,242 A | 10/1998 | Follmer et al. | |
| 5,833,652 A | 11/1998 | Preissman et al. | |
| 5,843,032 A * | 12/1998 | Kastenhofer | 604/103.06 |
| 5,868,707 A | 2/1999 | Williams et al. | |
| 5,897,567 A | 4/1999 | Ressemann et al. | |
| 5,968,052 A | 10/1999 | Sullivan, II et al. | |
| 5,972,015 A | 10/1999 | Scribner et al. | |
| 5,980,532 A | 11/1999 | Wang | |
| 6,027,477 A * | 2/2000 | Kastenhofer | 604/103.09 |
| 6,124,007 A | 9/2000 | Wang et al. | |
| 6,139,525 A | 10/2000 | Davis-Lemessy et al. | |
| 6,171,278 B1 | 1/2001 | Wang et al. | |
| 6,217,585 B1 * | 4/2001 | Houser et al. | 606/108 |
| 6,235,043 B1 | 5/2001 | Reiley et al. | |
| 6,241,734 B1 | 6/2001 | Scribner et al. | |
| 6,296,655 B1 | 10/2001 | Gaudoin et al. | |
| 6,423,012 B1 | 7/2002 | Kato et al. | |
| 6,423,083 B2 | 7/2002 | Reiley et al. | |
| 6,471,673 B1 * | 10/2002 | Kastenhofer | 604/103.06 |
| 6,585,687 B1 | 7/2003 | Shkolnik | |
| 6,596,217 B1 | 7/2003 | Davis-Lemessy et al. | |
| 6,599,296 B1 | 7/2003 | Gillick et al. | |
| 6,602,224 B1 | 8/2003 | Simhambhatla | |
| 6,659,977 B2 * | 12/2003 | Kastenhofer | 604/96.01 |
| 6,663,646 B1 | 12/2003 | Shah | |
| 6,663,648 B1 | 12/2003 | Trotta | |
| 6,719,773 B1 | 4/2004 | Boucher et al. | |
| 6,723,113 B1 | 4/2004 | Shkolnik | |
| 6,833,392 B1 | 12/2004 | Acquarulo, Jr. et al. | |
| 6,946,173 B2 | 9/2005 | Lim et al. | |
| 7,066,998 B2 | 6/2006 | Rohrbaugh et al. | |
| 7,070,613 B2 | 7/2006 | Weber et al. | |
| 7,485,108 B2 * | 2/2009 | Kastenhofer | 604/96.01 |
| 7,485,250 B2 * | 2/2009 | Boatman et al. | 264/494 |
| 7,635,347 B2 * | 12/2009 | Kastenhofer | 604/103.06 |
| 2002/0010420 A1 | 1/2002 | Bagaoisan et al. | |
| 2002/0163104 A1 | 11/2002 | Motsenbocker et al. | |
| 2003/0074017 A1 | 4/2003 | Shah | |
| 2003/0135231 A1 | 7/2003 | Goodin et al. | |
| 2003/0229184 A1 | 12/2003 | Acquarulo, Jr. et al. | |
| 2004/0062890 A1 | 4/2004 | Wang et al. | |
| 2004/0092948 A1 | 5/2004 | Stevens et al. | |
| 2004/0098017 A1 | 5/2004 | Saab et al. | |
| 2004/0225296 A1 | 11/2004 | Reiss et al. | |
| 2005/0059989 A1 | 3/2005 | Eidenschink | |
| 2005/0070846 A1 | 3/2005 | Wang | |
| 2005/0113856 A1 | 5/2005 | Epstein et al. | |
| 2006/0085023 A1 | 4/2006 | Davies et al. | |
| 2006/0282150 A1 | 12/2006 | Olson et al. | |
| 2008/0051707 A1 | 2/2008 | Phan et al. | |
| 2008/0051818 A1 | 2/2008 | Phan et al. | |
| 2008/0051819 A1 | 2/2008 | Chasmawala et al. | |
| 2008/0086083 A1 * | 4/2008 | Towler | 604/103.06 |
| 2008/0097374 A1 * | 4/2008 | Korleski et al. | 604/500 |
| 2008/0140173 A1 * | 6/2008 | Eskaros et al. | 623/1.11 |
| 2009/0226504 A1 * | 9/2009 | Peters | 424/426 |

FOREIGN PATENT DOCUMENTS

| | | |
|---|---|---|
| WO | 9856301 | 12/1998 |
| WO | WO 2006/034396 A2 | 3/2006 |

* cited by examiner

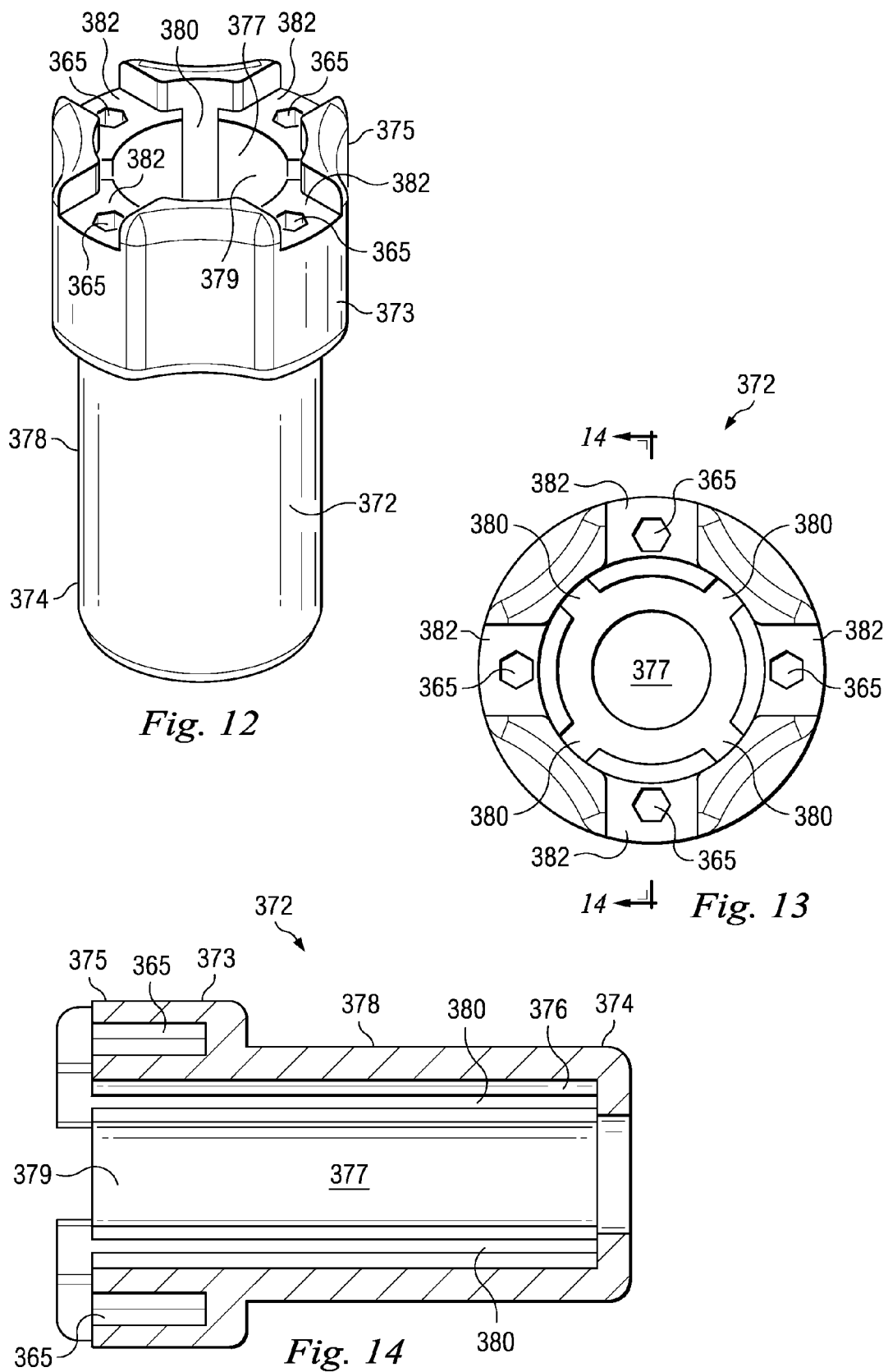

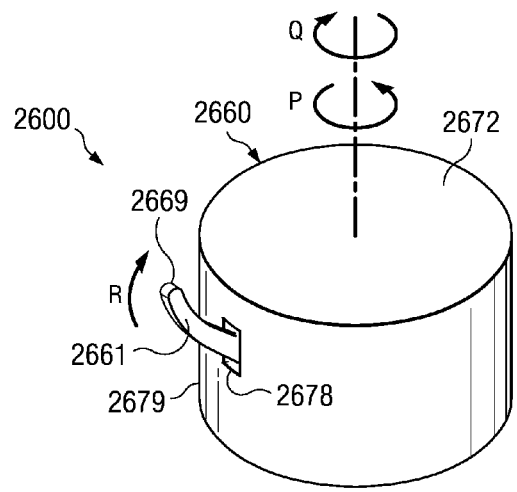
*Fig. 27*
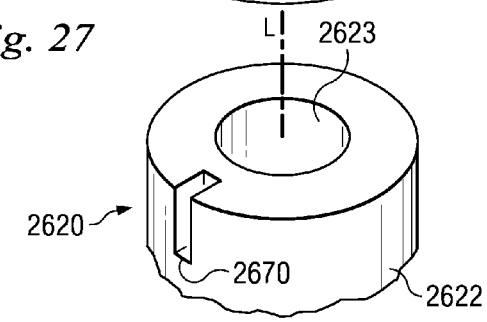
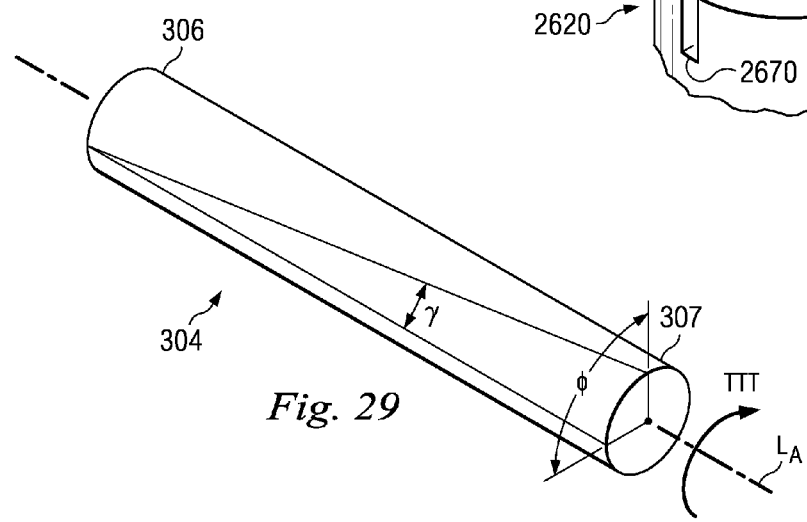
*Fig. 29*
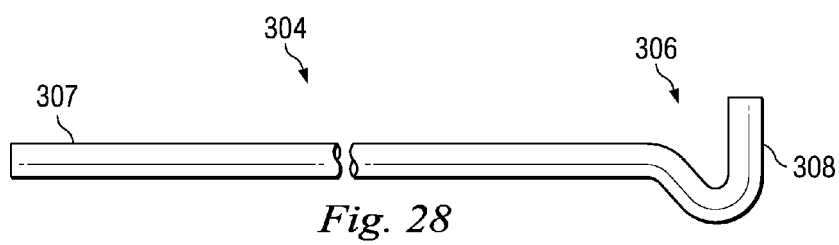
*Fig. 28*

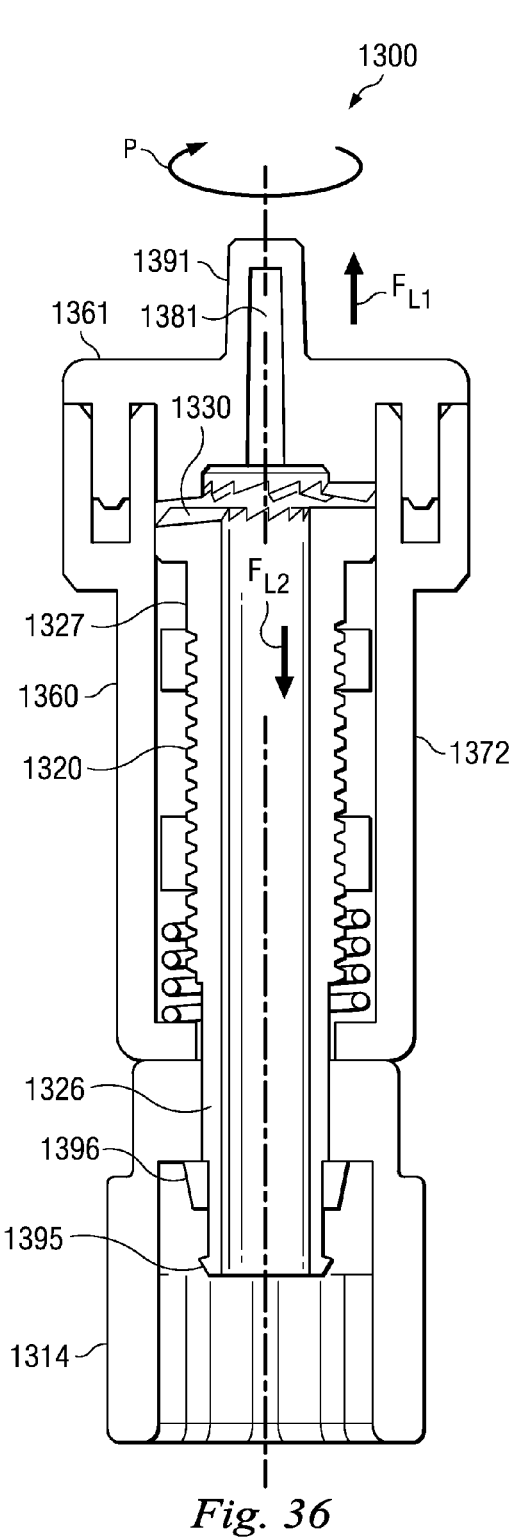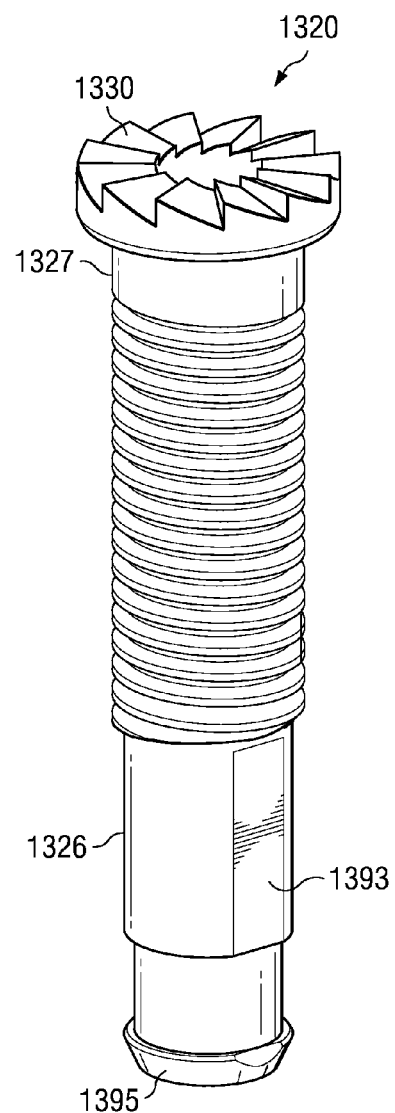
Fig. 36
Fig. 37

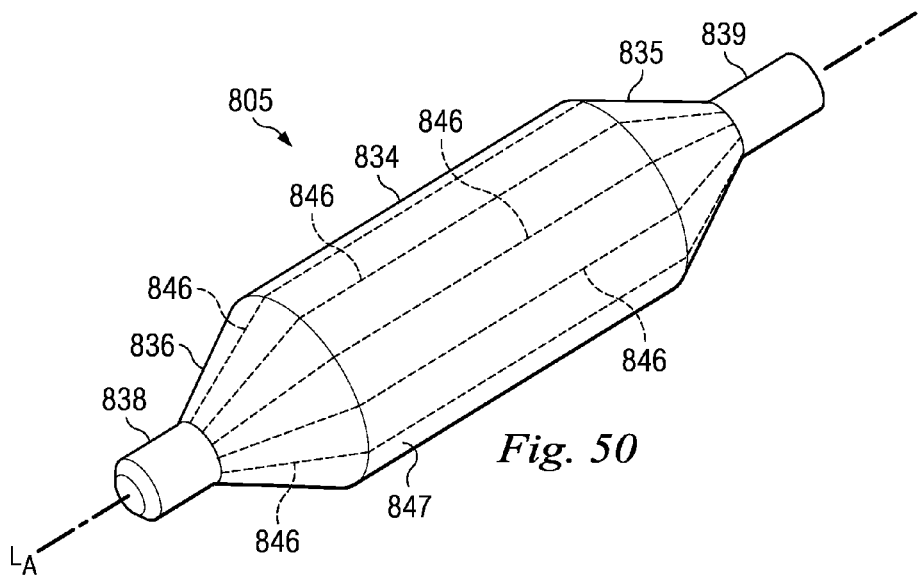
Fig. 50
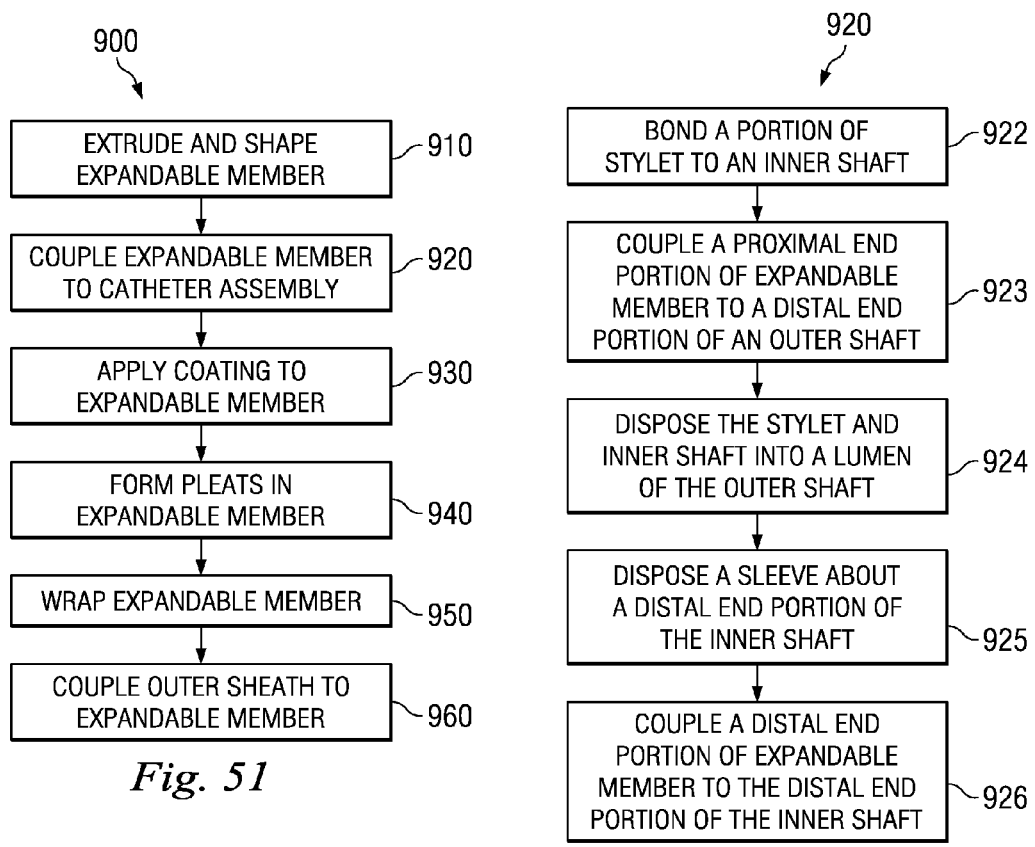
Fig. 51
Fig. 52

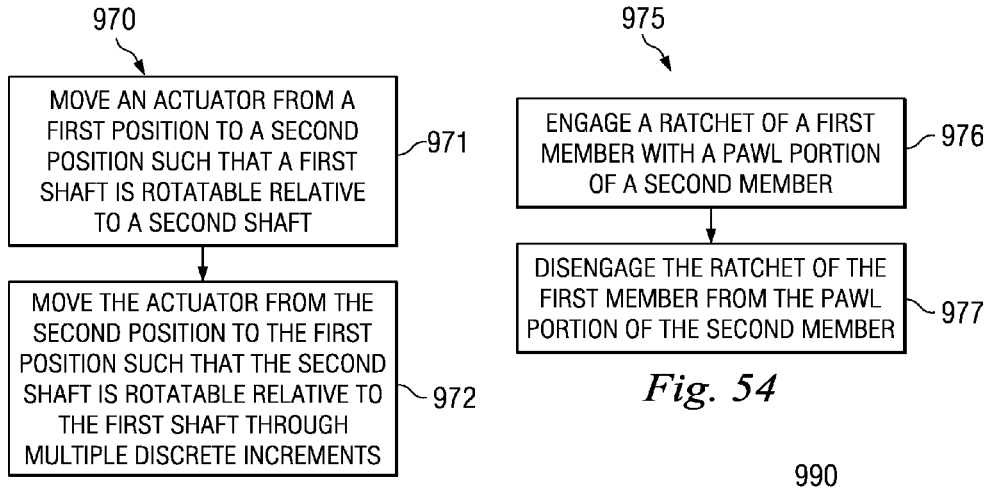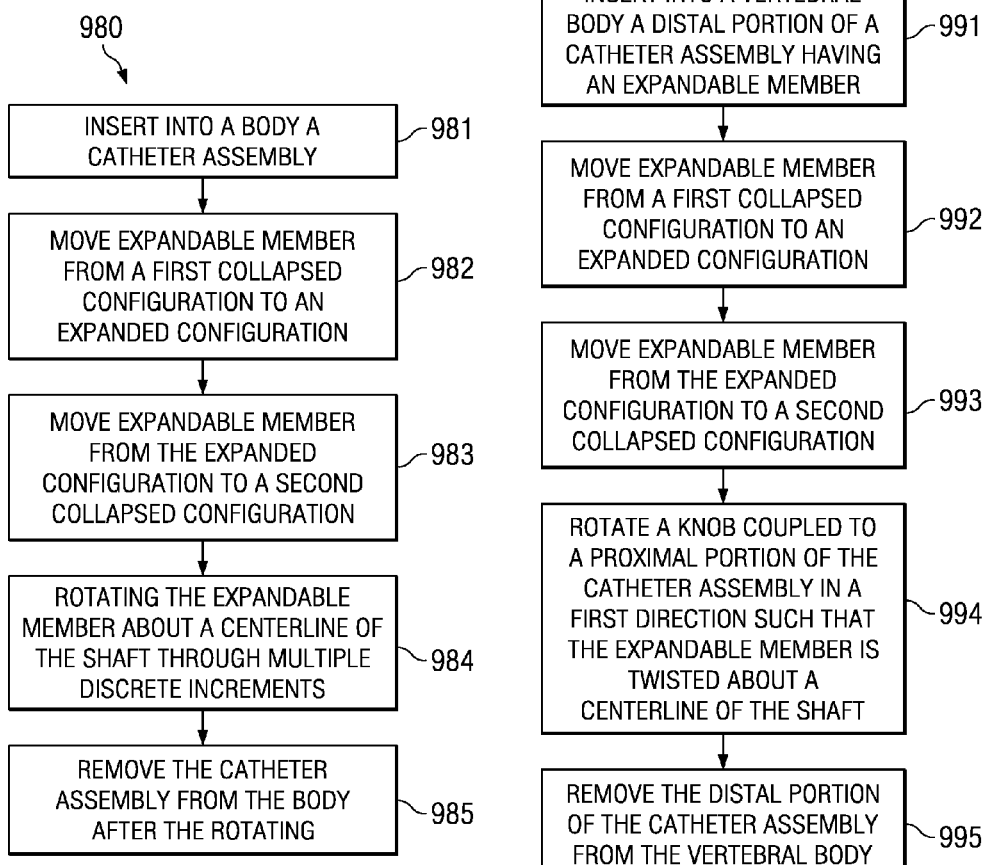

APPARATUS AND METHODS FOR USE OF EXPANDABLE MEMBERS IN SURGICAL APPLICATIONS

CROSS-REFERENCE TO RELATED APPLICATIONS

This application claims priority to U.S. Provisional Application Ser. No. 60/884,050, entitled "Apparatus and Methods for Use of Expandable Members in Surgical Applications," filed Jan. 9, 2007, which is incorporated herein by reference in its entirety.

This application claims priority to U.S. Provisional Patent Application Ser. No. 60/823,566, entitled "Apparatus and Methods for Collapsing an Expandable Member of a Medical Device," filed Aug. 25, 2006, which is incorporated herein by reference in its entirety.

This application is related to U.S. patent application Ser. Nos. 11/730,347, 11/730,349 and 11/730,345, each entitled "Apparatus and Methods for Use of Expandable Members in Surgical Applications," filed on the same date, each of which is incorporated herein by reference in their entirety.

BACKGROUND

The invention relates generally to medical devices and procedures. More particularly, in some embodiments, an apparatus comprises a catheter assembly and an expandable member for repairing bone defects, displacing tissue and/or compressing tissue.

Expandable members are used in various minimally-invasive medical procedures. When deployed, the expandable member may be exposed to rough surfaces and/or high inflation pressures. Such an environment can cause abrasion, tearing and/or puncturing of the expandable member, thereby rendering them inoperative. Moreover, upon completion of such procedures, the expandable member is often returned to its collapsed configuration so that it can be removed from the patient's body, for example, via a cannula. Even when placed in a collapsed configuration, however, expandable members can have a wall thickness and/or an overall size such that even when in the collapsed configuration the balloons are not easily removed through the cannula.

Some known medical devices are configured to wrap an expandable member to reduce the size of the expandable member when in the collapsed configuration. Many of these medical devices, however, do not include components, such as for example, a shaft, a connector or the like, configured to withstand the torsional stress caused by such twisting.

Some known medical devices are configured to wrap and/or fold the expandable member to reduce the size of the expandable member when in the collapsed configuration. Many of these medical devices, however, do not include any mechanism for controlling the rotation of the expandable member.

Thus, a need exists for medical devices with expandable members having improved resistance against abrasion, tearing and/or puncturing for in various medical applications. For example, a medical device having an expandable member having multiple layers and/or coatings configured to resist tearing and puncturing may be desirable for use in environments in which the expandable member may contact hard, rough surfaces. A medical device having a mechanism for controlling the rotation of an expandable member may also be desirable. For example, an improved mechanism for contracting an expandable member after deployment may be particularly applicable in percutaneous medical procedures.

SUMMARY

Medical devices having expandable members are described herein. In some embodiments, an apparatus includes an expandable member and an elongate assembly. The expandable member is configured to displace a first portion of a bone structure relative to a second portion of the bone structure when moved from a collapsed configuration to an expanded configuration. The elongate assembly includes a shaft and an elongated member disposed with a lumen defined by the shaft. A proximal end portion of the expandable member is coupled to a distal end portion of the shaft such that the proximal end portion of the expandable member does not rotate relative to the distal end portion of the shaft when at least a portion of the expandable member is twisted about the elongated member through at least four revolutions. A distal end portion of the expandable member is coupled to a distal end portion of the elongated member such that the distal end portion of the expandable member does not rotate relative to the distal end portion of the elongated member when at least the portion of the expandable member is twisted about the elongated member through at least four revolutions.

BRIEF DESCRIPTION OF THE DRAWINGS

FIGS. 12 through 14 show a perspective view, a top view and a cross-sectional view, respectively, of a housing portion of the medical device shown in FIG. 3.

FIG. 27 is a perspective exploded view of a medical device according to an embodiment of the invention.

FIG. 28 is a front view of a stylet portion of the medical device shown in FIG. 3.

FIG. 29 is a perspective view of a portion of the medical device shown in FIG. 3.

FIGS. 35 and 36 are cross-sectional views of a twisting apparatus according to an embodiment of the invention in a first configuration and a second configuration, respectively.

FIG. 37 is a perspective view of a portion of the twisting apparatus shown in FIGS. 35 and 36.

FIG. 50 is a perspective view of an expandable member according to an embodiment of the invention in an expanded configuration.

FIG. 51 is a flow chart of a method according to an embodiment of the invention.

FIG. 52 is a flow chart of a method according to an embodiment of the invention.

FIG. 53 is a flow chart of a method according to an embodiment of the invention.

FIG. 54 is a flow chart of a method according to an embodiment of the invention.

FIG. 55 is a flow chart of a method according to an embodiment of the invention.

FIG. 56 is a flow chart of a method according to an embodiment of the invention.

DETAILED DESCRIPTION

Figure 1A:
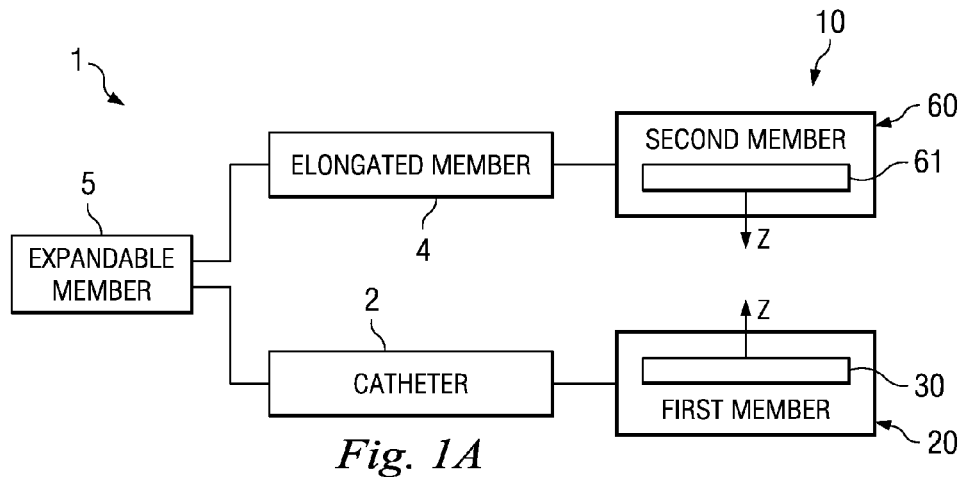
FIG. 1A is a schematic illustration showing a medical device according to an embodiment of the invention.

Medical devices having expandable members are described herein. In some embodiments, an apparatus includes a support member and a knob, each having an engagement portion. The support member is coupled to a shaft of a catheter assembly. The knob is configured to engage a stylet of the catheter assembly. The knob is configured to rotate relative to the support member through multiple discrete increments when the engagement portion of the knob is engaged with the engagement portion of the support member. Each discrete increment can be, for example, less than one revolution (e.g., thirty degrees of rotation). In some embodiments, for example, the catheter assembly includes an expandable member coupled to the shaft and the stylet such that when the knob is rotated relative to the support member, at least a portion of the expandable member is twisted about the catheter assembly.

In some embodiments, an apparatus includes an elongate assembly and an actuator. The elongate assembly has a first shaft and a second shaft disposed within the first shaft. The first shaft is configured to be coupled to a proximal portion of an expandable member. The second shaft is configured to be coupled to a distal portion of the expandable member. The actuator is configured to rotate the second shaft relative to the first shaft through multiple discrete increments. In some embodiments, for example, the actuator can include a ratchet wheel have multiple ratchet teeth and a pawl configured to engage the ratchet teeth, such that each discrete increment is associated with a ratchet tooth.

In some embodiments, an apparatus includes a first member and a second member. The first member has a ratchet wheel and is coupled to a catheter. The second member has a pawl portion and engages a shaft rotatably disposed within the catheter. The pawl portion is configured to engage the ratchet wheel to cooperatively resist the rotation of the second member with respect to the first member when the second member and the first member are collectively in a first configuration. The pawl portion is configured to be spaced apart from the ratchet wheel when the second member and the first member are collectively in a second configuration.

In some embodiments, an apparatus includes a support member and a knob. The support is configured to be coupled to a shaft of a catheter assembly. The knob is configured to engage an elongated member of the catheter assembly rotatably disposed within the shaft of the catheter assembly. The knob is configured to rotate unidirectionally relative to the support member when the support member and the knob are collectively in a first configuration. The knob is configured to rotate bidirectionally relative to the support member when the support member and the knob are collectively in a second configuration. In some embodiments, the catheter assembly includes an expandable member having a proximal end portion and a distal end portion. The proximal end portion of the expandable member is coupled to a distal end portion of the shaft. The distal end portion of the expandable member is coupled to a distal end portion of the elongated member. In this manner, when the knob is rotated relative to the support member, at least a portion of the expandable member is twisted about a longitudinal axis of the catheter assembly.

In some embodiments, an apparatus includes a catheter assembly, an expandable member and an actuator. The catheter assembly has a first shaft and a second shaft disposed within the first shaft. The expandable member has a proximal portion coupled to the first shaft and a distal portion coupled to the second shaft. The actuator is configured to rotate the second shaft relative to the first shaft in a first direction to twist at least a portion of the expandable member about a centerline of the second shaft. The actuator is configured to prevent rotation of the second shaft relative to the first shaft in a second direction opposite the first direction.

In some embodiments, an apparatus includes an elongated member, an expandable member coupled to the elongated member, and an outer sheath. The outer sheath, which can be constructed from a different material than the expandable member, is disposed about the expandable member such that an outer surface of the expandable member is in discontinuous contact with an inner surface of the outer sheath. The expandable member and the outer sheath are configured to cooperatively displace a bone structure when moving between a collapsed configuration and an expanded configuration.

In some embodiments, an apparatus includes an elongated member, an expandable member, an outer sheath and a clamp. The expandable member is coupled to the elongated member and is constructed from a first material, such as, for example, Nylon 12. The outer sheath is disposed about the expandable member and is constructed from a second material different than the first material, such as Teflon. The clamp is configured to couple the outer sheath to the expandable member.

In some embodiments, an apparatus includes an elongated member and an expandable member. The expandable member is coupled to the elongated member and is configured to displace a first portion of a spine relative to a second portion of the spine when moving between a collapsed configuration and an expanded configuration. The expandable member includes a first layer and a second layer. The first layer is constructed from a first polymer. The second layer is disposed about the first layer and is constructed from a second polymer, different than the first polymer. The second polymer has a molecular structure that is more amorphous than the molecular structure of the first polymer. In some embodiments, the elongated member can further include an actuator configured to twist at least a portion of the expandable member about the elongated member through a predetermined number of rotations.

In some embodiments, an apparatus includes an elongated member and an expandable member. The expandable member is coupled to the elongated member and includes a first layer and a second layer. The first layer is constructed from a first material having a lubricity. The second layer is disposed about the first layer and is constructed from a second material having a lubricity greater than the lubricity of the first material. The elongated member can further include an actuator configured to twist the expandable member about the elongated member, the actuator including a ratchet.

In some embodiments, an apparatus includes an elongated member and an expandable member configured to displace bone. The expandable member is coupled to the elongated member and includes an abrasion-resistant coating disposed about a portion of an outer surface of the expandable member. The expandable member defines multiple pleats when in a collapsed configuration. In some embodiments, the elongated member can further include an actuator configured to twist the expandable member about a longitudinal axis of the elongated member.

In some embodiments, an apparatus includes an expandable member and an elongate assembly. The expandable member is configured to displace a first portion of a bone structure relative to a second portion of the bone structure when moved from a collapsed configuration to an expanded configuration. The elongate assembly includes a shaft and an elongated member disposed with a lumen defined by the shaft. A proximal end portion of the expandable member is coupled to a distal end portion of the shaft such that the proximal end portion of the expandable member does not rotate relative to the distal end portion of the shaft when at least a portion of the expandable member is twisted about the elongated member through at least four revolutions. A distal end portion of the expandable member is coupled to a distal end portion of the elongated member such that the distal end portion of the expandable member does not rotate relative to the distal end portion of the elongated member when at least the portion of the expandable member is twisted about the elongated member through at least four revolutions.

In some embodiments, an apparatus includes an expandable member, an elongate assembly and a sleeve. The expandable member is configured to displace a first portion of a spine relative to a second portion of the spine when moved from a collapsed configuration to an expanded configuration. The elongate assembly includes a shaft, an elongated member rotatably disposed within the shaft, and a stylet disposed within the elongated member. At least a portion of the stylet is bonded to at least a first portion of the elongated member. The sleeve is disposed between an outer surface of the elongated member and an inner surface of the expandable member. The sleeve is coupled to the distal end portion of the expandable member and a second portion of the elongated member. In some embodiments, the second portion of the elongated member can be different than the first portion of the elongated member.

In some embodiments, an apparatus includes an expandable member, a shaft and an elongated member rotatably disposed within the shaft. The expandable member is configured to displace a first portion of a bone structure relative to a second portion of the bone structure when moved from a collapsed configuration to an expanded configuration. The shaft has a distal end portion coupled to a proximal end portion of the expandable member. A distal end portion of the elongated member is coupled to a distal end portion of the expandable member. The shaft is configured to have an angle of twist between a proximal end portion of the shaft and the distal end portion of the shaft of less than one hundred eighty degrees when at least a portion of the elongated member is rotated relative to the shaft through at least four revolutions.

In some embodiments, an apparatus includes a catheter assembly and an expandable member. The expandable member is configured to displace bone when moving between a collapsed configuration and an expanded configuration. The catheter assembly includes an outer shaft, an inner shaft, a stylet and a twisting apparatus. A portion of the inner shaft is movably disposed within the outer shaft. Similarly, a portion of the stylet is disposed within the inner shaft. At least one of the stylet or the inner shaft is coupled to a distal end portion of the expandable member. Similarly, the outer shaft is coupled to a proximal end portion of the expandable member. The twisting apparatus is coupled to the outer shaft and the stylet and is configured to rotate the stylet within the outer shaft to twist the expandable member about the stylet. At least one of the outer shaft, the inner shaft or the stylet being constructed of a polymer reinforced with nano-particles.

In some embodiments, a method includes disposing a first portion of an expandable member about a first catheter shaft and a second portion of the expandable member about a second catheter shaft. An adhesive is disposed between the second portion of the expandable member and the second catheter shaft. An induction coil is disposed about the first catheter shaft without being in physical contact with the first catheter shaft or the second catheter shaft. An alternating current is supplied to the indication coil, thereby producing a magnetic field about the first catheter shaft, which induces a current within the first catheter shaft. The alternating current is supplied for a predetermined time period, during which the first portion of the expandable member changes from a solid to a liquid. The alternating current is then removed, allowing the first portion of the expandable member to solidify.

In some embodiments, a method includes coupling, to an elongated member, an expandable member configured to displace a first portion of a spine relative to a second portion of the spine when moving between a collapsed configuration and an expanded configuration. An outer sheath is disposed about the expandable member. A clamp is placed about a portion of the outer sheath to couple the outer sheath to the expandable member.

In some embodiments, a method includes bonding a portion of a stylet within an elongated member. A proximal end portion of an expandable member is coupled to a distal end portion of a shaft defining a lumen. The elongated member is disposed within the lumen of the shaft such that a distal end portion of the elongated member extends from the distal end portion of the shaft. A sleeve is disposed about the distal end portion of the elongated member. A distal end portion of the expandable member is coupled to the distal end portion of the elongated member.

In some embodiments, a method includes moving an actuator from a first position to a second position such that a first shaft is rotatable relative to a second shaft. The second shaft is disposed within the first shaft and coupled to an expandable member. The actuator is moved from the second position to the first position such that the second shaft is rotatable relative to the first shaft through a plurality of discrete increments.

In some embodiments, a method includes engaging a ratchet of a first member coupled to a first shaft with a pawl portion of a second member coupled to a second shaft such that the second shaft can rotate relative to the first shaft in a first direction. The second shaft is coupled to an expandable member. The ratchet of the first member is disengaged from the pawl portion of the second member such that that the second shaft can rotate relative to the first shaft in a second direction opposite the first direction.

In some embodiments, a method includes inserting into a body a catheter assembly including a shaft and an expandable member coupled to the shaft. The expandable member is moved from a first collapsed configuration to an expanded configuration. The expandable member is moved from the expanded configuration to a second collapsed configuration, after the moving the expandable member from the first collapsed configuration. The expandable member is rotated about a centerline of the shaft through a plurality of discrete increments.

In some embodiments, a method includes inserting into a vertebral body a distal portion of a catheter assembly. The catheter assembly includes a shaft and an expandable member coupled to the shaft. The expandable member is moved from a first collapsed configuration to an expanded configuration after the inserting. The expandable member is moved from the expanded configuration to a second collapsed configuration after the moving the expandable member from the first collapsed configuration. A knob coupled to a proximal portion of the catheter assembly is rotated in a first direction such that the expandable member is twisted about a centerline of the shaft. The knob is configured to resist rotation in a second direction opposite the first direction. The distal portion of the catheter assembly is removed from the vertebral body.

In some embodiments, a method includes inserting an expandable member into an interior portion of a bone structure. The expandable member includes a first layer and a second layer disposed about the first layer such that an outer surface of the first layer is in discontinuous contact with an inner surface of the second layer. The first layer is constructed from a first polymer having a molecular structure. The second layer is constructed from a second polymer having a molecular structure more amorphous than the molecular structure of the first polymer. The expandable member is expanded while disposed within the interior portion of the bone structure such that the expandable member exerts a force sufficient to cause a first portion of the bone structure to move relative to a second portion of the bone structure.

In some embodiments, a method includes inserting into a body a catheter assembly. The catheter assembly includes an expandable member, a shaft having a distal end portion coupled to a proximal end portion of the expandable member, and an elongated member rotatably disposed within the shaft. A distal end portion of the elongated member is coupled to a distal end portion of the expandable member. The expandable member is moved from a collapsed configuration to an expanded configuration. The expandable member is moved from the expanded configuration to the collapsed configuration. At least a portion of the elongated member is rotated relative to the shaft such that at least a portion of the expandable member is twisted about the elongated member through at least four revolutions while maintaining a fluid-tight seal between the distal end portion of the expandable member and the distal end portion of the elongated member.

In some embodiments, a method includes inserting a distal portion of a cannula into a patient's body to establish a percutaneous path to a tissue in the patient's body (e.g., a vertebral body). A balloon catheter having a balloon in a contracted and/or twisted configuration is inserted into the cannula, and the balloon is advanced into the tissue. Once the balloon is positioned within the tissue, a twisting apparatus disposed on the proximal portion of the balloon catheter is actuated to rotate the balloon relative to the catheter. In this manner, the balloon can be placed in an un-twisted configuration after being disposed inside the tissue. In some embodiments, for example, the twisting apparatus can include a counter to indicate the number of rotations through which the balloon has been rotated. Alternatively, the twisting apparatus can be configured such that after a pre-defined number of rotations have been applied, further rotation of the twisting apparatus will not lead to further un-twisting of the balloon. In yet other embodiments, the twisting apparatus can include a ratchet and/or a locking mechanism to prevent undesired un-twisting of the twisted/contracted balloon.

Once the balloon is un-twisted, a fluid is introduced through the catheter into the balloon to inflate the balloon. In some embodiments, the inflation of the balloon may result in a cavity being formed within the tissue. For example, in some embodiments, the balloon can be positioned within a bone structure having a first cortical wall, a second cortical wall and cancellous bone portion disposed within the first and the second cortical walls. The inflation of the balloon can result in the compression of at least portion of the cancellous bone portion, thereby forming the cavity. Moreover, in some embodiments, the inflation of the balloon can cause the first cortical wall to move in relation to the second cortical wall, thereby increasing the distance between the first cortical wall and the second cortical wall. In some embodiments, for example, the pressure of the fluid inside the balloon may need to be maintained between 1.4 MPa and 2.8 MPa (200 psi and 400 psi) to produce a lifting force sufficient to move the first cortical wall away from the second cortical wall.

Once the cavity is formed within the tissue, the fluid is then withdrawn from the balloon to deflate the balloon. The balloon is then rotated via the twisting apparatus to further reduce the profile of the balloon. As described herein, in some embodiments, the twisting apparatus can include a ratcheting mechanism such that the balloon can be twisted in a controlled and/or incremental fashion. After the balloon has been sufficiently twisted, the balloon is then withdrawn from the patient's body via the cannula.

The term "expandable member" as used herein includes a component of a medical device that is configured to be changed or moved from a collapsed configuration to an expanded configuration in which the expandable member is larger than in the collapsed configuration. In some variations, the expandable member is configured to be expanded, for example, by introducing a medium such as liquid and/or gas into the interior of the expandable member. The expandable member can be, for example, a balloon configured to expand from a collapsed configuration to an expanded configuration. In some applications, the balloon is constructed, at least in part, from a low-compliant material.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "proximal" and "distal" refer to the direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the end of a medical device first inserted inside the patient's body would be the distal end, while the opposite end of the medical device (e.g., the end of the medical device being operated by the operator) would be the proximal end of the medical device.

FIG. 1A is a schematic illustration of a medical device 1 according to an embodiment of the invention. The medical device 1 includes a twisting apparatus 10 configured to be coupled to a catheter 2. The catheter 2 is coupled to an elongated member 4, such as, for example, a stylet, a tube, a rod, a cannula an/or a combination thereof, such that the elongated member 4 can be moved relative to the catheter 2. The elongated member 4 is coupled to an expandable member 5. The expandable member 5 is also coupled to the catheter 2 such that movement of the elongated member 4 relative to the catheter 2 causes the expandable member 5 to be twisted and/or folded. Although the elongated member 4 is shown as being indirectly coupled to the catheter 2 via the expandable member 5 and/or the twisting apparatus 10, in other embodiments the elongated member 4 can be directly coupled to the catheter 2. For example, in some embodiments, the elongated member 4 can be directly coupled to the catheter 2 via a bearing, a retention surface or the like (none of which are shown in FIG. 1A).

The twisting apparatus 10 has a first member 20 and a second member 60. The first member 20 is coupled to the catheter 2 and has an engagement portion 30. The engagement portion 30 may also be referred to as a ratchet portion, a clutch portion or a locking portion. The second member 60 is engaged with a portion of the elongated member 4 such that movement of the second member 60 causes the elongated member 4 to move in a similar fashion. The second member 60 includes an engagement portion 61, which may also be referred to as a pawl portion. The engagement portion 61 of the second member 60 is configured to be removably engaged with the engagement portion 30 of the first member 20 (as indicated by the arrows Z) such that the movement of the second member 60 relative to the first member 20 can be controlled, thereby controlling the twisting and/or folding of the expandable member 5.

In some embodiments, for example, the engagement portion 61 of the second member 60 is configured to be removably engaged with the engagement portion 30 of the first member 20 such that when the engagement portion 61 of the second member 60 is engaged with the engagement portion 30 of the first member 20, the second member 60 can be rotated relative to the first member 20 through multiple discrete increments. Such discrete increments can be, for example, predefined discrete increments (e.g., one quarter of a turn, one full turn, etc.). Conversely when the engagement portion 61 of the second member 60 is engaged with the engagement portion 30 of the first member 20, the second member 60 can be rotated relative to the first member 20 in an continuous, uninterrupted fashion.

As described in more detail herein, in some embodiments, a twisting apparatus can include a ratcheting, clutching and/or locking mechanism, such that once the elongated member is rotated in a first direction (e.g., clockwise relative to the catheter), the ratcheting mechanism can prevent the elongated member from rotating in a second direction (e.g., counter-clockwise relative to the catheter). In this manner, the twisting apparatus can allow the operator to twist the expandable member through multiple rotations of the elongated member relative to the catheter in a controlled and/or incremental fashion. Moreover, the ratcheting mechanism can prevent the elongated member from "springing back" (e.g., rotating in the second direction) due to the increased tension and/or torque produced by the twisting of the expandable member about the catheter, thus allowing the user to wrap the expandable member very tightly about the catheter. In some embodiments, the twisting apparatus can include a release such that the operator can disengage the ratcheting mechanism to allow counter rotation of the elongated member, thus allowing the expandable member to be untwisted.

As described in more detail herein, in some embodiments, a twisting apparatus can be configured with a counter to indicate the number of rotations through which the expandable member has been rotated. Such a counter can be configured to provide an indication of the number of rotations in a single direction. Alternatively, a counter can be configured to provide an indication of the number of rotation in both a clockwise and a counter clockwise direction. In some embodiments, the counter is configured to provide a visual indicator of the number of rotations through which the expandable member has been rotated.

In some embodiments, as described in more detail herein, a twisting apparatus can also be configured with a mechanism to prevent over-rotation of the expandable member. For example, in some embodiments, a twisting apparatus can be configured to allow only six clockwise rotations of the elongated member in relation to the catheter. In some embodiments, a "rotation limiting" twisting apparatus can prevent further rotation of the twisting apparatus once the expandable member has been rotated a predetermined number of rotations. In other embodiments, a rotation limiting twisting apparatus can allow unlimited rotation of the twisting apparatus, however, once the expandable member has been rotated a predetermined number of rotations, further twisting of the twisting apparatus will not lead to further rotation of the elongated member relative to the catheter.

Although the catheter 2 is shown as being spaced apart from the elongated member 4, each of which is coupled to the same end portion of an expandable member, in some embodiments, a medical device can include an elongated member coaxially and rotatably positioned within the catheter. In such embodiments, for example, a distal portion of the catheter can be coupled to a proximal portion of an expandable member (e.g., balloon). A distal portion of the elongated member can be coupled to a distal portion of the expandable member. A twisting apparatus of the type described herein can couple the catheter to the elongated member such that the elongated member can be rotated relative to the catheter, resulting in the twisting or un-twisting of the expandable member. In some embodiments, the twisting apparatus can be connected to the proximal end of the catheter and/or the proximal end of the elongated member.

Figure 1B:
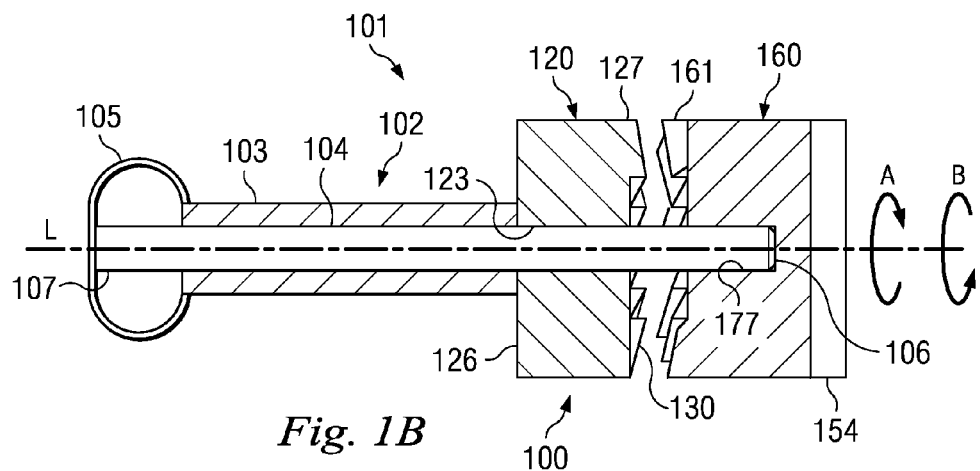
FIG. 1B is a schematic illustration showing a medical device according to an embodiment of the invention in which a twisting apparatus includes a first member having a ratchet wheel and a second member having a pawl portion configured to engage the ratchet wheel.

FIG. 1B is a schematic illustration of a cross-sectional view of a medical device 101 according to an embodiment of the invention. The medical device 101 includes a twisting apparatus 100 configured to be coupled to a catheter 102. The catheter 102 has an outer shaft 103 that defines a lumen through which a portion of an elongated member 104, such as, for example, a stylet, is disposed. The elongated member 104 has a distal end portion 107 coupled to an expandable member 105 and a proximal end portion 106. The expandable member 105 is also coupled to the outer shaft 103 such that rotation of the elongated member 104 relative to the outer shaft 103 causes the expandable member 105 to be twisted about a longitudinal axis L of the catheter 102.

The twisting apparatus 100 has a first member 120, a second member 160 and a biasing member 154. The distal end portion 126 of the first member 120 is coupled to the catheter 102. The first member 120 defines a lumen 123 through which the elongated member 104 is disposed and has a ratchet wheel 130 disposed at a proximal end portion 127 of the first member 120. The second member 160 defines an engagement portion 177 configured to engage the proximal end portion 106 of the elongated member 104 such that rotation of the second member 160 about the longitudinal axis L causes the elongated member 104 to rotate about the longitudinal axis L, as indicated by arrows A and B. The second member 160 includes a pawl portion 161 configured to engage the ratchet wheel 130 of the first member 120 such that the rotation of the second member 160 relative to the first member 120 can be controlled, thereby controlling the rotation of the elongated member 104. The biasing member 154 engages a portion of the second member 160 such that engagement between the pawl portion 161 and the ratchet wheel 130 is maintained. In use, the pawl portion 161 can be disengaged from the ratchet wheel 130 by applying an external force to counteract the biasing member 154.

Figure 2:
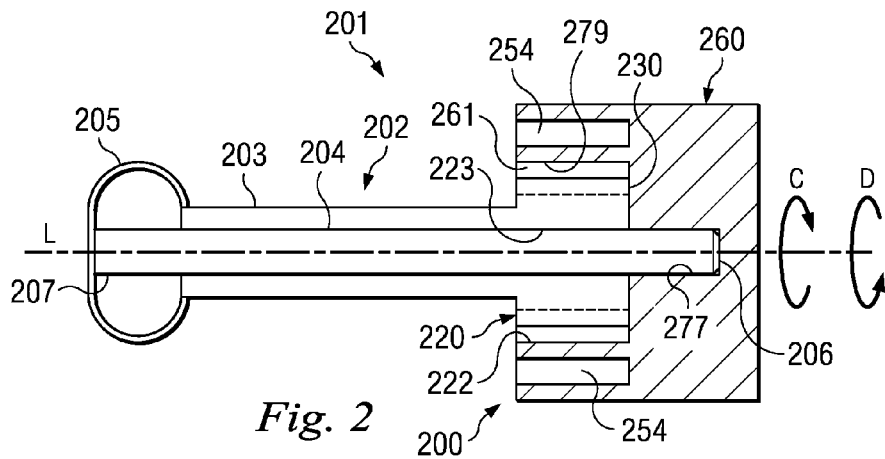
FIG. 2 is a schematic illustration showing a medical device according to an embodiment of the invention in which a twisting apparatus includes a first member having a ratchet wheel and a second member having a pawl portion and being disposed about the first member.

FIG. 2 is a schematic illustration of cross-sectional view of a medical device 201 according to an embodiment of the invention. The medical device 201 includes a twisting apparatus 200 configured to be coupled to a catheter 202 having an outer shaft 203 that defines a lumen through which a portion of an elongated member 204 is disposed. A distal end portion 207 of the elongated member 204 is coupled to an expandable member 205. As described above, the expandable member 205 is also coupled to the outer shaft 203 such that rotation of the elongated member 204 relative to the outer shaft 203 causes the expandable member 205 to be twisted about a longitudinal axis L of the catheter 202, as indicated by arrows C and D.

The illustrated twisting apparatus 200 has a first member 220, a second member 260 and a biasing member 254. A portion of the first member 220 is coupled to the catheter 202. The first member 220 defines a lumen 223 through which a portion of the elongated member 204 is disposed and has a ratchet wheel 230 disposed on its outer side wall 222. The second member 260 defines an engagement portion 277 configured to engage the proximal end portion 206 of the elongated member 204 such that rotation of the second member 260 about the longitudinal axis L causes the elongated member 204 to rotate about the longitudinal axis L. The second member 260 includes a pawl portion 261 disposed on the side wall 222 of the second member 260. As described above, the pawl portion 261 is configured to engage the ratchet wheel 230 of the first member 220 such that the rotation of the second member 260 relative to the first member 220 can be controlled. The biasing member 254 engages a portion of the second member 260 such that engagement between the pawl portion 261 and the ratchet wheel 230 is maintained.

Although the elongated members described herein are shown and described as being disposed within a portion of the catheter and a portion of the twisting apparatus, in other embodiments, an elongated member can be disposed outside of the catheter and/or the twisting apparatus. In yet other embodiments, an elongated member can be positioned such that its longitudinal axis is not parallel and/or coincident with the longitudinal axis of the catheter and/or the twisting apparatus.

Figure 3:
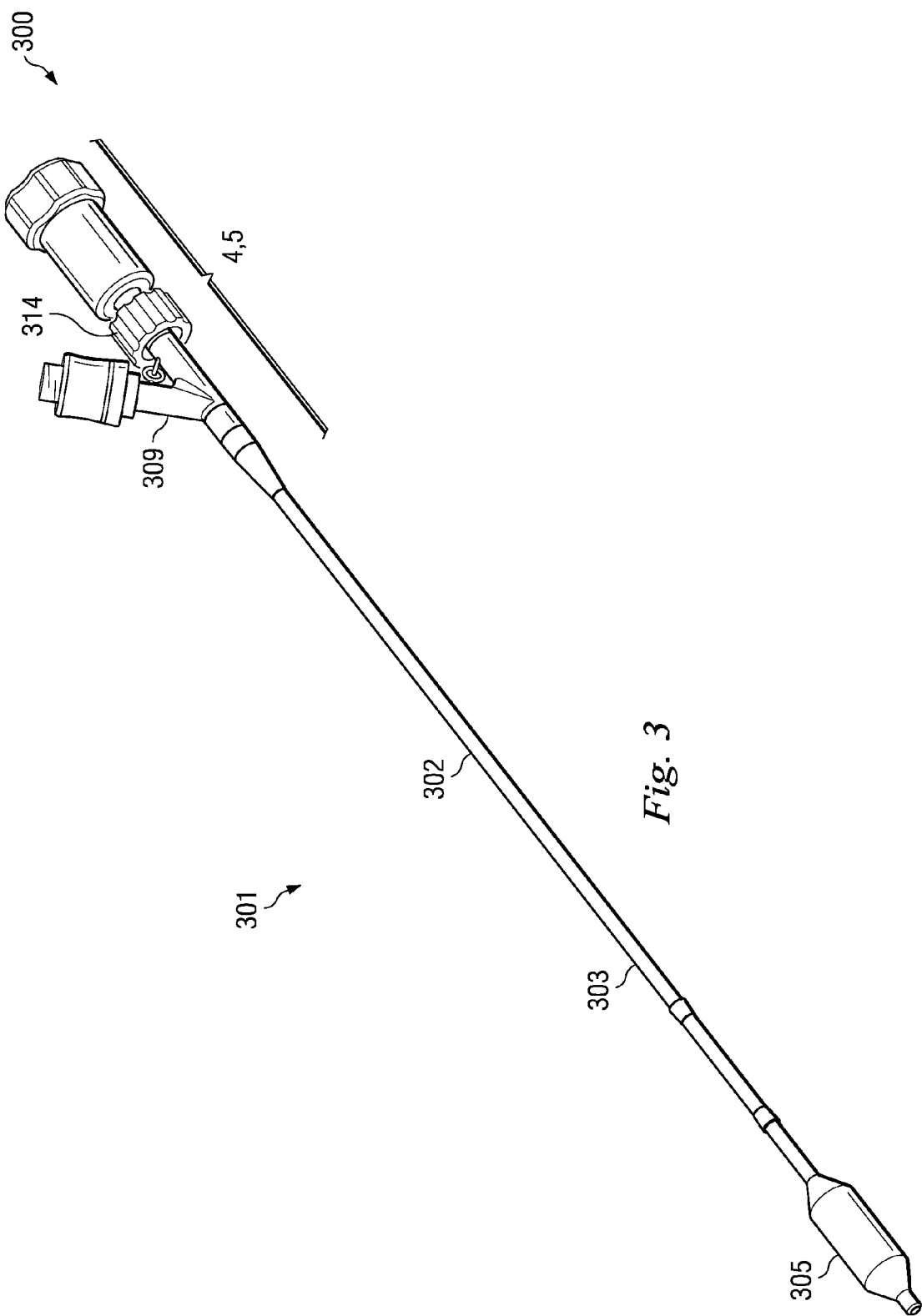
FIG. 3 is a perspective view of a medical device according to an embodiment of the invention.

FIG. 3 is a perspective view of a medical device 301 according to an embodiment of the invention that includes a actuator 300 coupled to a catheter assembly 302 via coupler 314. The illustrated catheter assembly 302 has a Y-connector 309 and an outer shaft 303 that defines a lumen through which a portion of a stylet 304 (see FIG. 6) is disposed. The catheter assembly 302 includes an expandable member 305 coupled to a distal portion of the outer shaft 303 and a distal portion of the stylet 304. In this manner, rotation of the stylet 304 relative to the outer shaft 303 causes at least a portion of the expandable member 305 to be twisted about the stylet 304.

As described in more detail herein, in some embodiments, the expandable member 305 is configured to be inserted into a body via a cannula (not shown in FIG. 3). Accordingly, in some embodiments, the actuator 300 is configured to twist at least a portion of the expandable member 305 about the stylet 304 such that the expandable member 305 can be removed via the cannula. Said another way, in some embodiments, the actuator 300 is configured twist at least a portion of the expandable member 305 about the stylet 304 such that the profile (e.g., the outer diameter) of the expandable member 305 is less than the diameter of the cannula. In some embodiments, for example, the medical device 301 is configured twist at least a portion of the expandable member 305 about the stylet 304 through at least three revolutions. In other embodiments, the medical device 301 is configured twist at least a portion of the expandable member 305 about the stylet 304 through at least four revolutions. In yet other embodiments, the medical device 301 is configured twist at least a portion of the expandable member 305 about the stylet 304 through at least six revolutions.

Figure 6:
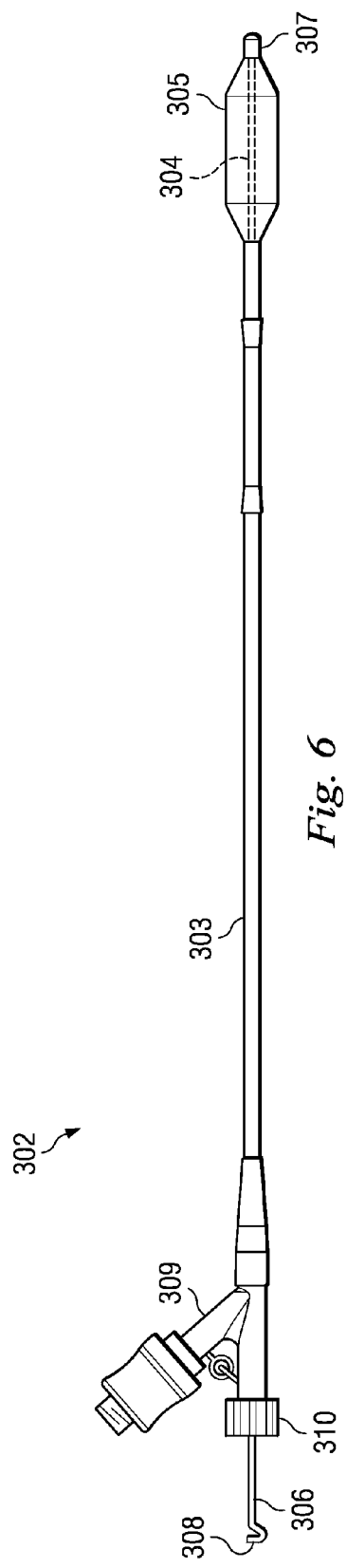
FIG. 6 is a front view of a portion of the medical device shown in FIG. 3.

FIG. 6 is a front view of the catheter assembly 302 decoupled from the actuator 300. As described above, the catheter assembly 302 has an outer shaft 303 that defines a lumen through which a portion of a stylet 304 is disposed. An expandable member 305 is coupled to a portion of the outer shaft 303 and a distal end portion 307 of the stylet 304. The outer shaft 303 is coupled to a Y-connector 309, which can be in communication with an inflation lumen (not shown) of the catheter assembly 302. In some embodiments, the Y-connector can include a valve to selectively place the inflation lumen in fluid communication with an inflation devices (e.g., a syringe, a source of pressurized fluid or the like). In some embodiments, for example, the Y-connector can include a check valve (e.g., a "one-way" valve) to control the direction of the flow of fluid into the inflation lumen. A luer cap 310 is disposed at the proximal end of the catheter assembly 302. The proximal end portion 306 of the stylet 304 extends beyond the luer cap 310 and includes a engagement portion 308 configured to be received by the actuator 300, as described herein. In some embodiments, the luer cap 310 can be constructed from a suitable polymer, such as polycarbonate.

Although shown as including a linear outer shaft and a stylet disposed therein, in some embodiments, as discussed in more detail herein, a catheter assembly can include any number of shafts, tubes and/or other components. For example, in some embodiments, the catheter assembly can include an outer shaft, an inner shaft and a stylet disposed within the inner shaft, similar to the catheter disclosed in U.S. Pat. No. 6,719,773, which is incorporated herein by reference in its entirety. In other embodiments, a catheter assembly can be devoid of a stylet and include only an outer shaft and an inner tube coupled to an expandable member, the inner tube being configured to rotate within the outer shaft to cause the expandable member to be twisted and/or folded as described herein. In other embodiments, the catheter can include an inner shaft defining a lumen configured to receive a portion of a guide wire. In yet other embodiments, the catheter assembly can include other components, such as a strain relief member configured to improve the strength at the connection between the Y-connector and the outer shaft, an insertion sleeve configured to protect the expandable member during insertion and removal and/or a distal sleeve.

Moreover, in some embodiments, a catheter assembly can include one or more non-linear portions. For example, in some embodiments, a catheter assembly can include an outer shaft having a curved portion. In other embodiments, the outer shaft and/or the stylet can be flexible.

Figure 4:
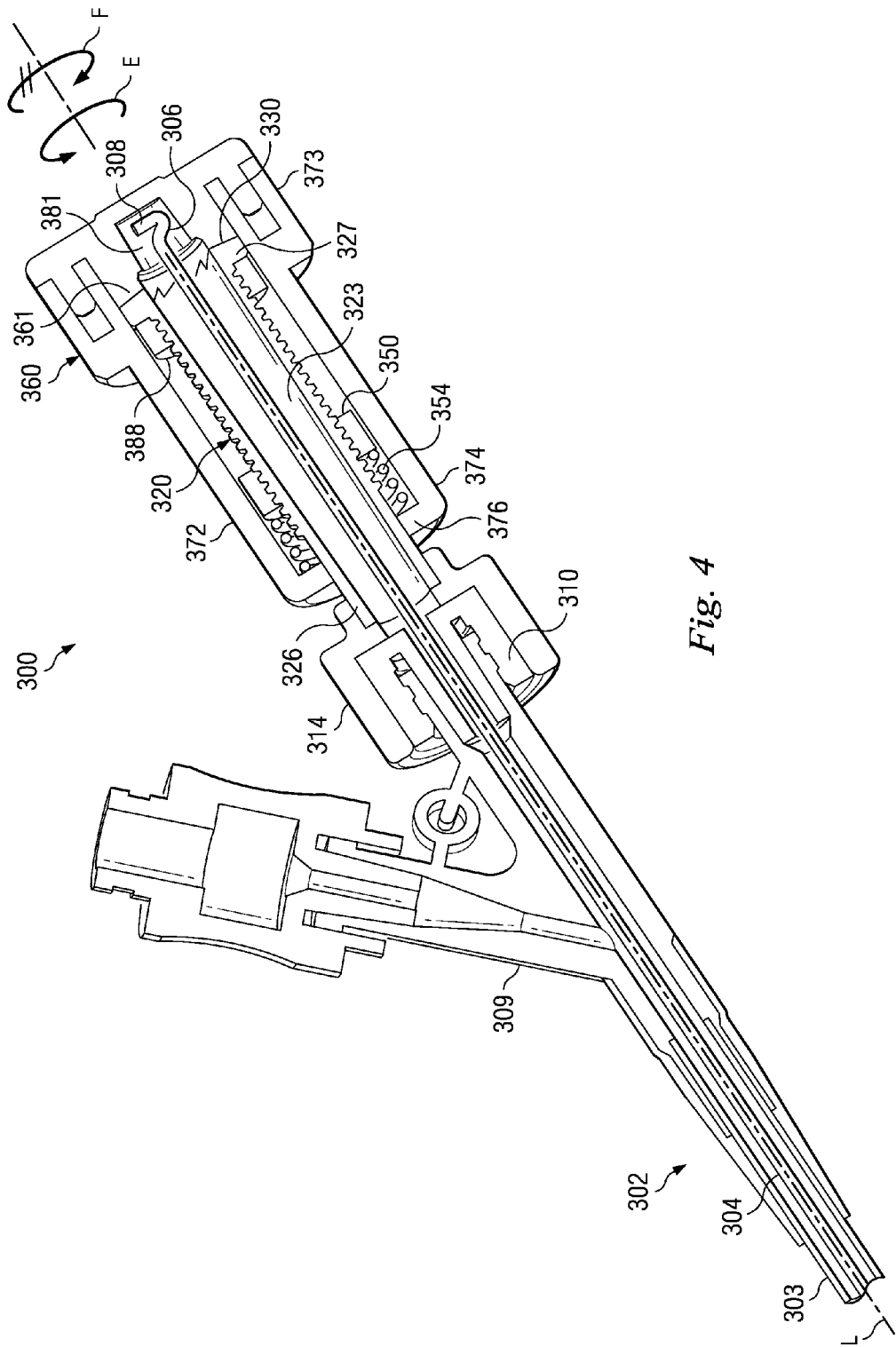
FIGS. 4 and 5 are cross-sectional perspective views of the portion of the medical device shown in FIG. 3 labeled as 4,5 in a first configuration and a second configuration, respectively.
Figure 5:
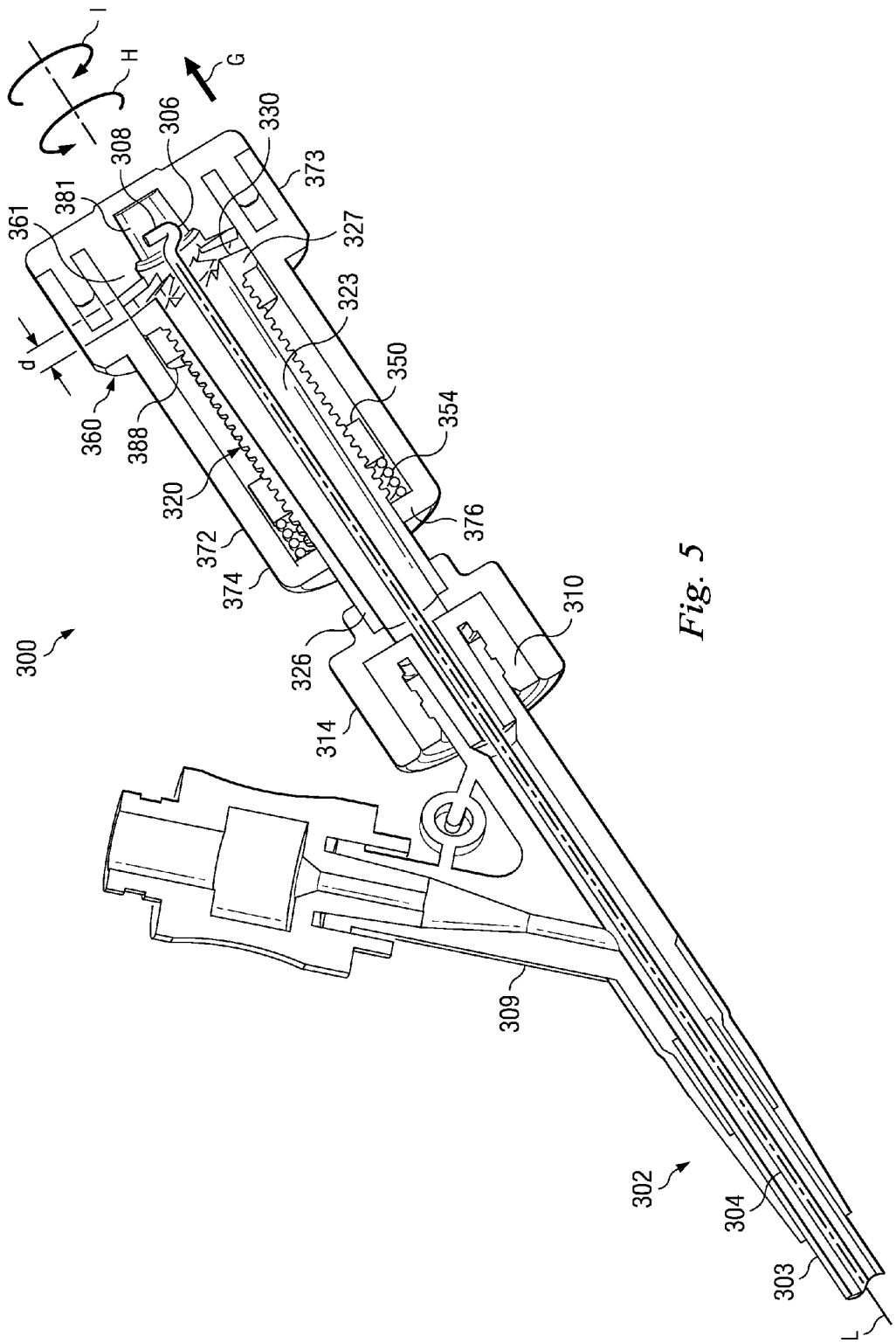
Figure 7:
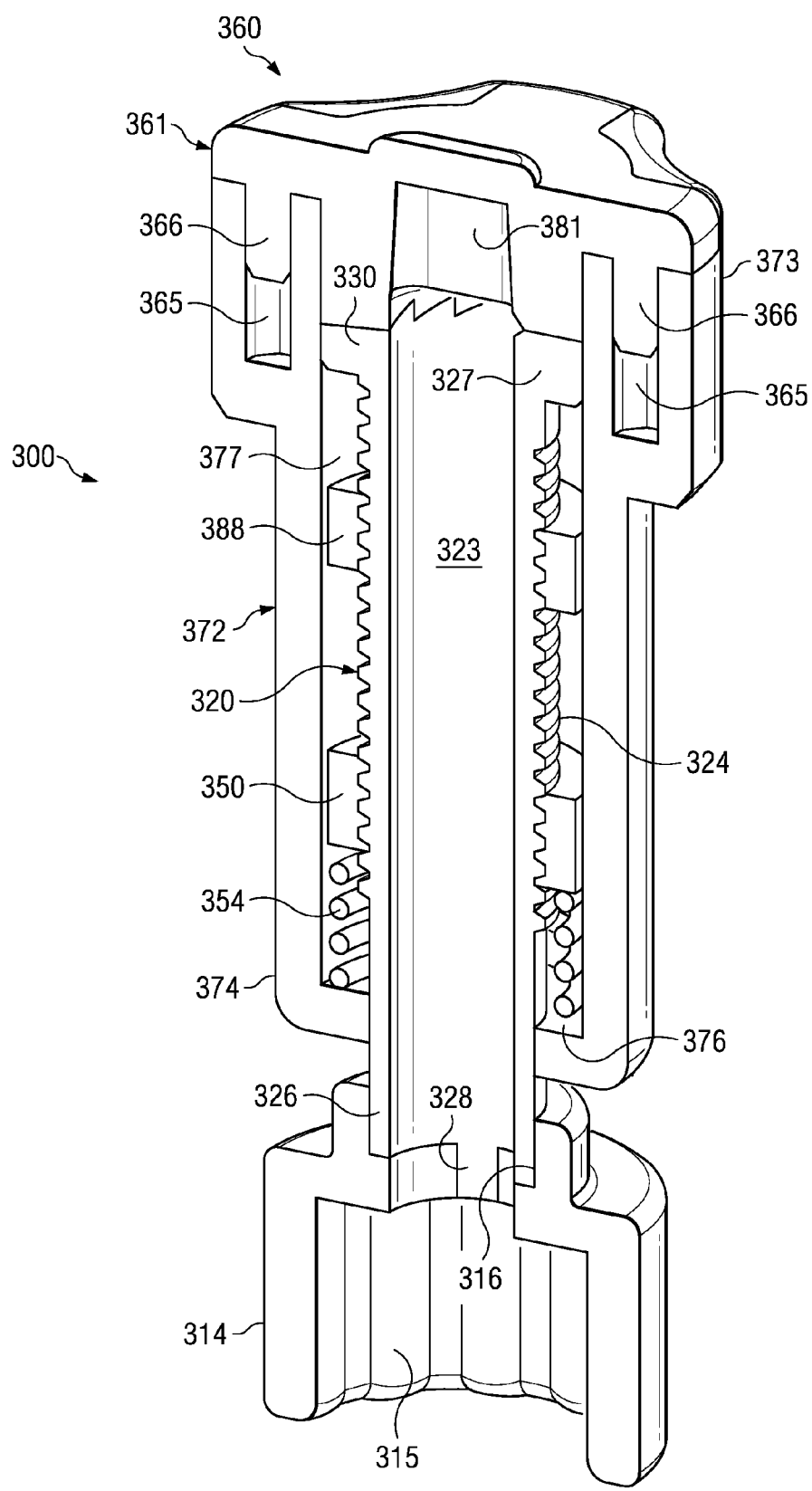
FIG. 7 is a cross-sectional perspective view of the twisting apparatus of the medical device shown in FIG. 3.
Figure 8:
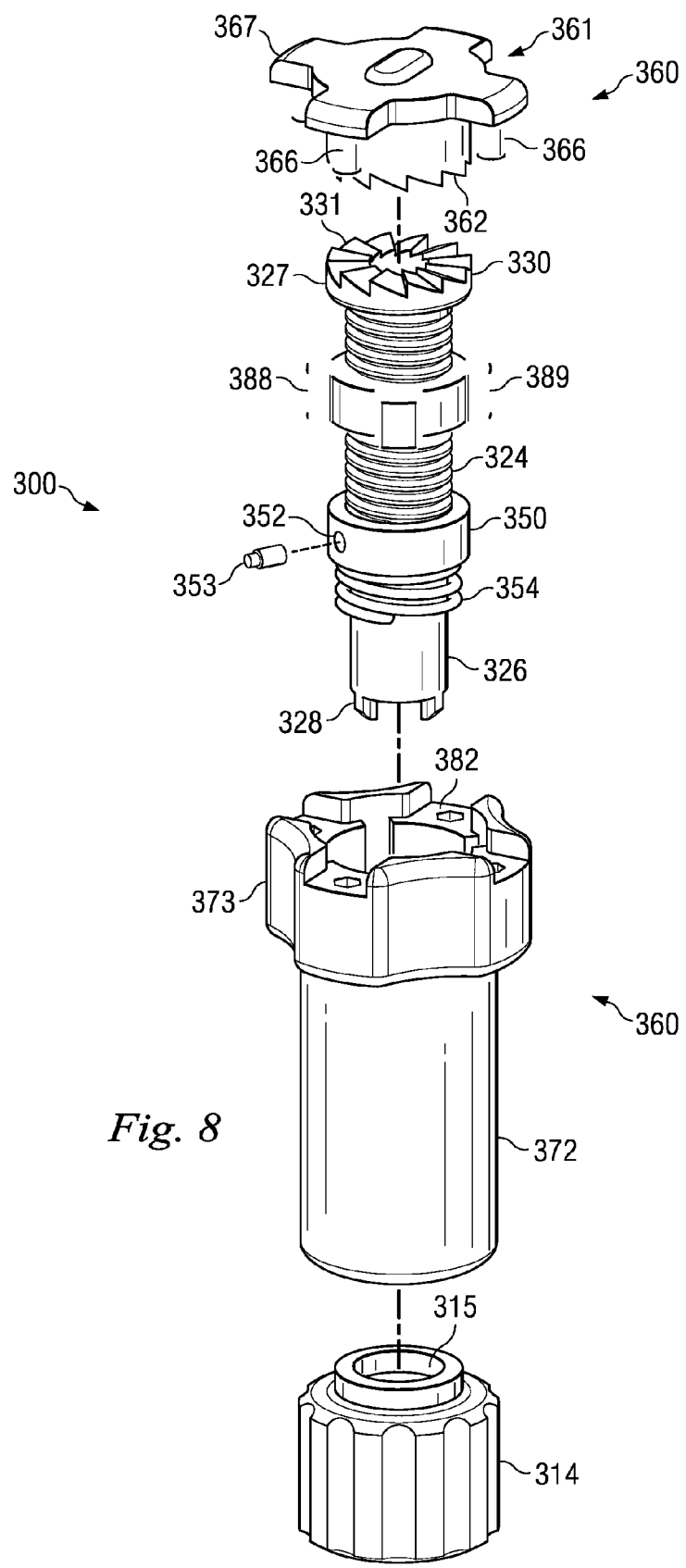
FIG. 8 is an exploded view of the twisting apparatus of the medical device shown in FIG. 3.

FIGS. 4 and 5 are cross-sectional views of the portion of the medical device 301 shown in FIG. 3 labeled as 4,5 showing the actuator 300 in a first configuration and a second configuration, respectively. FIG. 7 is a cross-sectional view of the actuator 300 decoupled from the catheter assembly 302. FIG. 8 is an exploded view of the actuator 300 decoupled from the catheter assembly 302. The illustrated actuator 300 includes a first member 320 and second member 360 disposed about the first member 320. The first member 320 includes a distal end portion 326 and a proximal end portion 327. The distal end portion 326 of the first member 320 is coupled to the luer cap 310 via coupler 314, such that the first member 320 cannot move relative to the catheter assembly 302. The proximal end portion 327 of the first member 320 includes a ratchet wheel 330 removably engagable with a pawl portion 361 of the second member 360. The first member 320 defines a lumen 323 through which a portion of the stylet 304 is disposed such that the stylet 304 can rotate about longitudinal axis L relative to the first member 320.

The second member 360 includes a housing portion 372 and a pawl portion 361 removably engagable with the ratchet wheel 330 of the first member 320. The housing portion 372 defines a lumen 377 within which the first member 320 is disposed. The housing portion 372 has a knob portion 373 and a spring engagement portion 376 disposed at its distal end 374. As illustrated, the spring engagement portion 376 is engaged with one end of a spring 354. The other end of the spring 354 is engaged with a spring shoulder 350 disposed about the first member 320. In this manner, the force from the spring 354 acts to move the second member 360 distally relative to the first member 320 such that the pawl portion 361 and the ratchet wheel 330 remain engaged (i.e., the first configuration as illustrated in FIG. 4).

Figure 15:
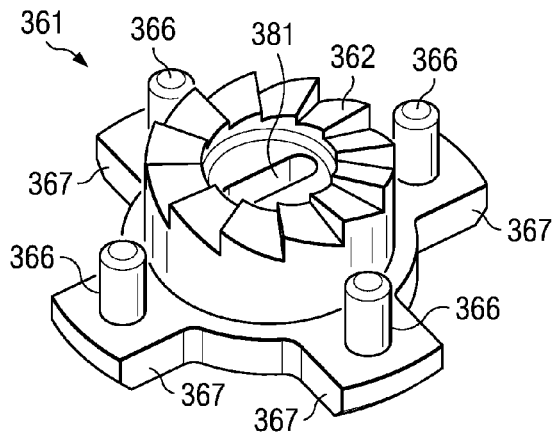
FIGS. 15 through 17 show a perspective view, a top view and a cross-sectional view, respectively, of a pawl portion of the medical device shown in FIG. 3.
Figure 16:
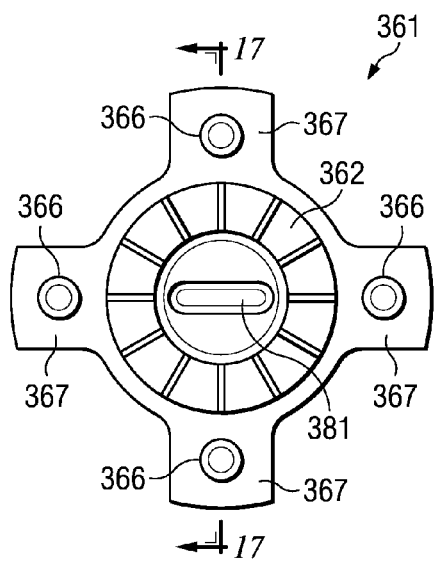
Figure 17:
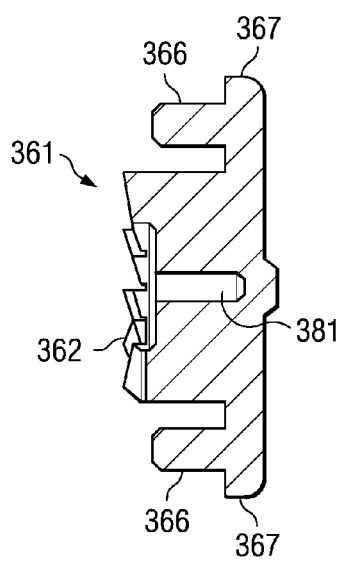

The pawl portion 361 of the second member 360 is fixedly coupled to the housing portion 372 and defines an opening 381 within which the engagement portion 308 of the stylet 304 is received. As illustrated in FIGS. 15 through 17, opening 381 has a long, narrow shape such that when the second member 360 rotates, the engagement portion 308 will engage the sides of the opening 381 thereby causing the stylet 304 to rotate with the second member 360. Moreover, because the engagement portion 308 is not coupled to the second member 360, the second member 360 can move axially relative to the stylet 304.

Figure 23:
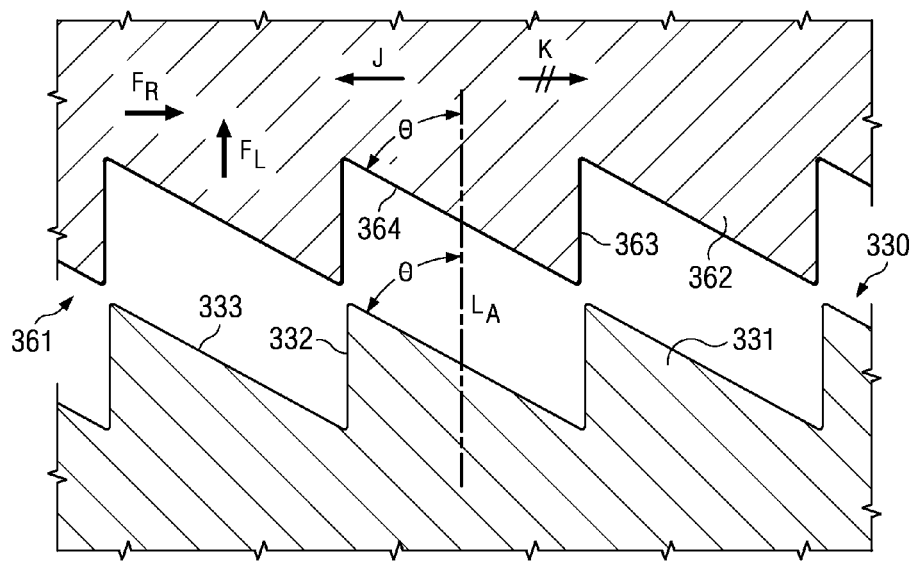
FIG. 23 is a schematic illustration showing the teeth portion of the ratchet wheel and pawl portion of the medical device shown in FIG. 3.

As illustrated in FIGS. 8 through 11, the ratchet wheel 330 of the first member 320 includes multiple teeth 331. Similarly, as illustrated in FIGS. 8 and 15 through 17, the pawl portion 361 of the second member 360 includes multiple teeth 362 configured to engage the teeth 331 on the ratchet wheel 330. As illustrated in FIG. 23, the teeth 331 on the ratchet wheel 330 each include a first retention surface 332 and a second retention surface 333 that collectively define a multiple recesses and protrusions that characterize the teeth 331. Similarly, the teeth 362 on the pawl portion 361 each include a first retention surface 363 and a second retention surface 364 that collectively define multiple recesses and protrusions that characterize the teeth 362 of the pawl portion 361. The first retention surfaces 363 of the pawl portion 361 are configured to complimentarily couple (e.g., mate) with the first retention surfaces 332 of the ratchet wheel 330. Similarly, the second retention surfaces 364 of the pawl portion 361 are configured to complimentarily couple (e.g., mate) with the second retention surfaces 333 of the ratchet wheel 330. The first retention surfaces 332, 363 are each substantially parallel to the longitudinal axis L, whereas the second retention surfaces 333, 364 are each at an angle $\Theta$ to the longitudinal axis L. In this manner, because the second retention surfaces 333, 364 are at an angle to the longitudinal axis L, the pawl portion 361 can move relative to the ratchet wheel 330 as indicated by the arrow J in FIG. 23 when the pawl portion 361 is engaged with the ratchet wheel 330. Said another way, when a rotational force is applied to the pawl portion 361, as indicated by the arrow J, the contact between the angled retention surfaces 333, 364 produces a resultant force $F_L$ on the pawl portion 361 that is parallel to the longitudinal axis L and in the proximal direction. Accordingly, when the resultant force $F_L$ is sufficient to overcome the force produced by the spring 354, the pawl portion 361 moves along the longitudinal axis L in a proximal direction away from the ratchet wheel 330, thereby allowing the pawl portion 361 to move as indicated by the arrow J.

Similarly, when a rotational force is applied to the pawl portion 361, as indicated by the arrow J, the contact between the angled retention surfaces 333, 364 produces a resultant force $F_R$ on the pawl portion 361 that opposes rotation in the direction as indicated by arrow J. Accordingly, when the actuator 300 is in its first (e.g., engaged) configuration (see FIG. 4), the pawl portion 361 and the ratchet wheel 330 cooperatively resist the rotation of the second member 360 relative to the first member 320. Such resistance can provide the user with better control when rotating the second member 360 relative to the first member 320.

Conversely, when a rotational force is applied to the pawl portion 361, as indicated by the arrow K, because the first retention surfaces 332, 363 are substantially parallel to the longitudinal axis L, no resultant force $F_L$ is produced when the first retention surfaces 332, 363 contact each other. Accordingly, the pawl portion 361 cannot move relative to the ratchet wheel 330 in the direction as indicated by the arrow K in FIG. 23 when the pawl portion 361 is engaged with the ratchet wheel 330.

Referring again to FIGS. 4 and 5, when the actuator 300 is in its first (e.g., engaged) configuration (see FIG. 4), the second member 360 (and therefore the stylet 304) can be rotated relative to the first member 320 about the longitudinal axis L in a direction as indicated by arrow E. The second member 360 cannot, however, be rotated in a direction as indicated by arrow F. As such, the expandable member 305 can be twisted and/or folded in a unidirectional fashion.

Moreover, when the actuator 300 is in its first configuration and the second member 360 is rotated in a direction as indicated by arrow E, the force exerted by the spring 354 urges the pawl portion 361 towards the ratchet wheel 360 when the tip portions (i.e., the protrusions) of the teeth 362 move past the tip portions (i.e., the protrusions) of the teeth 331. Accordingly, the tip portions of the teeth 362 of the pawl portion 361 snap into the corresponding recesses of the teeth 331 of the ratchet wheel 360. In this manner, the second member 360 can be rotated relative to the first member 320 in a controlled and/or incremental fashion. Said another way, when the actuator 300 is in its first (e.g., engaged) configuration, the second member 360 can be rotated relative to the first member 320 in a direction as indicated by arrow E through a set of discrete increments.

Each of the discrete increments is associated with the recesses and/or protrusions of the teeth 362 of the pawl portion 361 and/or the recesses and/or protrusions of the teeth 331 of the ratchet wheel 360. Said another way, the size of each discrete is proportional to the number of teeth 362 of the pawl portion 361 and/or the number of teeth 331 of the ratchet wheel 360. The size of each discrete increment can be any suitable amount. In some embodiments, for example, each discrete increment can be approximately thirty degrees of one revolution (e.g., when the number of teeth is twelve). In other embodiments, each discrete increment can be approximately one revolution. In yet other embodiments, the discrete increments can be non-uniform in size (e.g., the size of the increment decreases as a function of the angular position of the pawl portion 361 relative to the ratchet wheel 330.

In addition to allowing the pawl portion 361 to rotate relative to the ratchet wheel 330 through multiple discrete increments, the engagement of the teeth 362 of the pawl portion 361 and the teeth 331 of the ratchet wheel 360 can produce, for example, an audible noise and/or a haptic sensation at each discrete increment through which the pawl portion 361 is rotated. In this manner, the user can hear and/or feel the pawl portion 361 as it moves through each of the discrete increments.

When the actuator 300 is in its second (i.e., disengaged) configuration (see FIG. 5), the pawl portion 361 is displaced from the ratchet wheel 330 longitudinally by a distance d. As such, the second member 360 (and therefore the stylet 304) can be rotated relative to the first member 320 about the longitudinal axis L in either direction about the longitudinal axis L (as indicated by arrows H and I). Moreover, the rotation of the second member 360 relative to the first member 320 is not resisted by the pawl portion 361 and/or the ratchet wheel 330. In this manner, the actuator 300 can be disengaged to allow the expandable member 305 to be unfolded.

As described above, when the actuator 300 is in its first (i.e., engaged) configuration, the amount of force required rotate the first member 320 is related to, among other things, the friction force between the second retention surfaces 333, 364, the magnitude of the resultant force $F_L$, the magnitude of the force $F_R$ and/or the magnitude of the force produced by the spring 354. Accordingly, the ease with which the first member 320 can be rotated can be controlled by adjusting the angle Θ, the surface finish of the second retention surfaces 333, 364, the force of spring 354, and the like.

As discussed above, the spring 354 is disposed such that one end of the spring 354 is engaged with the spring engagement portion 376 of the second member 360 and the other end of the spring is engaged with the spring shoulder 350 coupled to the first member 320. In this manner, the spring 354 acts to bias the actuator 300 in the engaged configuration. In use, the actuator 300 can be placed in its disengaged configuration by moving the second member 360 axially in a direction indicated by arrow G (see FIG. 5), thereby displacing the pawl portion 361 from the ratchet wheel 330 by a distance d.

Figure 9:
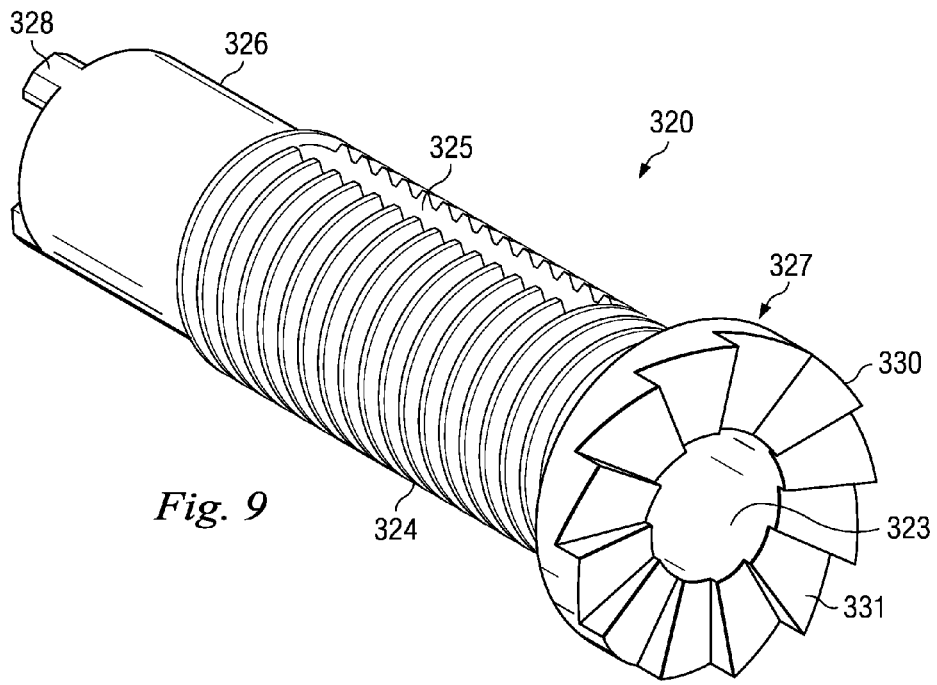
FIGS. 9 through 11 show a perspective view, a cross-sectional view and a front view, respectively, of a ratchet wheel portion of the medical device shown in FIG. 3.
Figure 10:
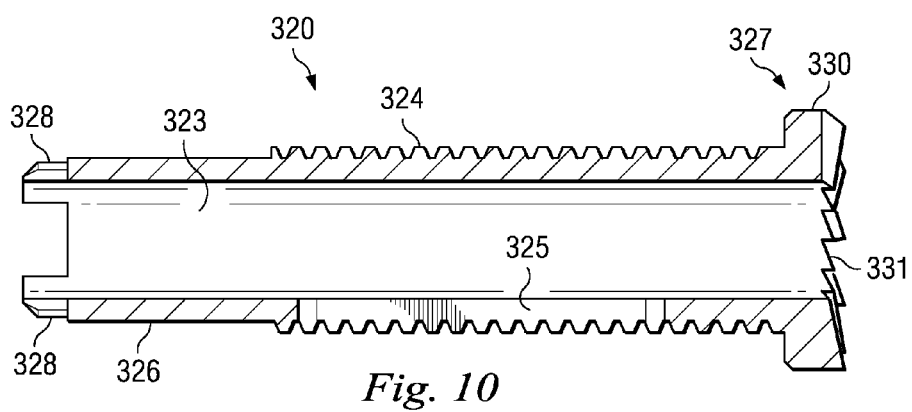
Figure 11:
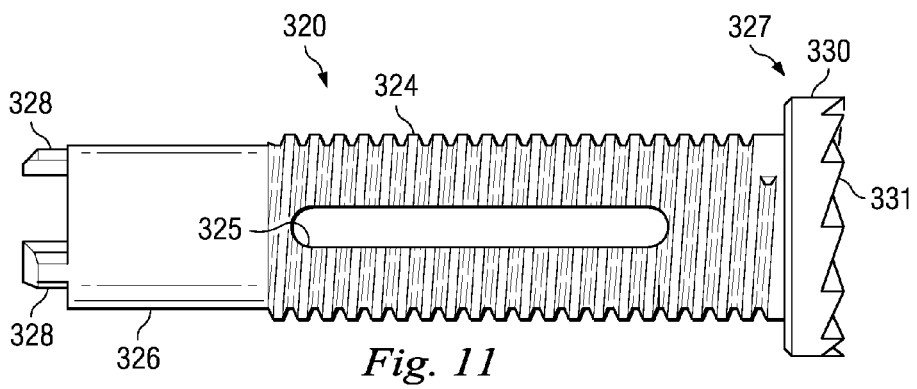
Figure 18:
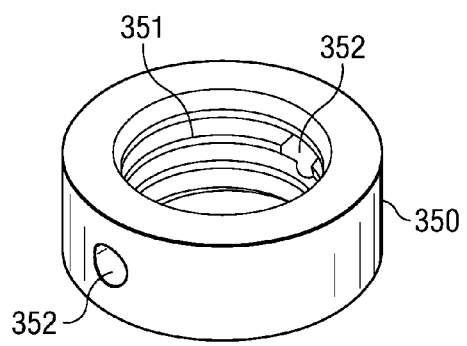
FIG. 18 is a perspective view of a spring shoulder portion of the medical device shown in FIG. 3.

The force required to displace the pawl portion 361 from the ratchet wheel 330 and/or the distance d can be adjusted by changing the position of the spring engagement portion 376, changing the position of the spring shoulder 350 and/or changing the spring constant associated with the spring 354. In the illustrated embodiment, the spring shoulder 350 is threadedly coupled to the first member 320, thereby allowing its position to be adjusted as desired. As illustrated in FIGS. 9 through 11, the first member 320 includes a threaded portion 324 having a slot 325 therethrough. The threaded portion 324 is configured to mate with the threaded portion 351 of the spring shoulder 350 (see FIG. 18). When the spring shoulder 350 is in the desired position, it is lockably coupled to the first member 320 by inserting a pin 353 through a pin bore 352 such that a portion of the pin extends into the slot 325 (see FIG. 8).

Figure 19:
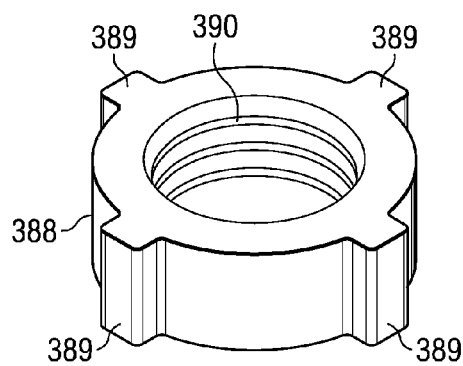
FIG. 19 is a perspective view of an indicator portion of the medical device shown in FIG. 3.

In addition to providing an engagement location for the spring 354, the spring shoulder 350 also acts in conjunction with the indicator 388 to limit the rotation of the second member 360. The indicator 388 is threadedly coupled to the first member 320 via mating threads 324 and 390 (see FIG. 19). In contrast to the arrangement of the spring shoulder 350, however, the indicator 388 is not lockably coupled to the first member 320, but is rather permitted to rotate freely along the threaded portion 324 of the first member 320. As shown in FIGS. 12, 13 and 19, the indicator 388 has four protrusions 389 configured to be received by the corresponding slots 380 defined by the inner surface 379 of the housing portion 372 of the second member 360. This arrangement allows the indicator 388 to move axially with respect to the second member 360, but prevents relative rotation between the indicator 388 and the second member 360. As such, when the second member 360 rotates relative to the first member 320, the indicator 388 rotates along the threaded portion 324 of the first member 320, thereby moving in an axial direction relative to the second member 360.

In use, when the expandable member 305 is in an untwisted configuration, the indicator 388 is positioned along the threaded portion 324 of the first member 320 such that it is in contact with a portion of the ratchet wheel 330. When the second member 360 is rotated in a direction corresponding to arrows E and H (in FIGS. 4 and 5, respectively), the indicator 388 travels axially along the threaded portion 324 of the first member 320 towards the spring shoulder 350. When the expandable member 305 is in its fully twisted configuration, the indicator 388 is in contact with the spring shoulder 350. In this manner, rotation of the second member 360 beyond point at which the expandable member 305 is in its fully twisted configuration is prevented because the indicator 388 cannot be moved further downward. Similarly, when the expandable member 305 is in its untwisted configuration, the contact between the indicator 388 and the ratchet wheel 330 prevents rotation in a direction corresponding to arrow I (see FIG. 5), even when the twisting apparatus in its disengaged configuration. Said another way, the spring shoulder 350 and the ratchet wheel 330 are positive stops limiting the rotation of the second member 360. In this manner, the actuator 300 can be configured to limit the number of turns through which the expandable member 305 can be twisted, thereby preventing the expandable member 305 from being over-twisted, which can potentially cause the expandable member 305 to fail or become decoupled from the stylet 304 and/or the catheter assembly 302. Similarly, the actuator 300 can be configured to prevent the expandable member 305 from being twisted in a direction opposite from that intended.

In some embodiments, the indicator 388 can provide an indication to a user of how many turns the second member 360 has undergone. In this manner, the user can monitor the twisting of the expandable member 305 to ensure that it is twisted a sufficient amount to facilitate removal via a cannula without over-twisting, which can potentially cause the expandable member 305 to fail or become decoupled from the stylet 304 and/or the catheter assembly 302. In some embodiments, the housing portion 372 is constructed from a transparent material, such as a clear polycarbonate, thereby allowing a user to visually determine how far the indicator has traveled. In other embodiments, the outer surface 378 of the housing portion 372 includes an indicia (not shown), such as a series of graduated markings, thereby allowing a user to easily determine the number of rotations that the second member has traveled. In yet other embodiments, the indicator includes a marking configured to be aligned with the corresponding markings on the housing portion 372. In yet other embodiments, the housing portion 372 includes a transparent window through which a user can view the indicator.

Although the indicator 388 is shown and described as being configured to provide both a visual indication of the amount of rotation and a positive stop, in other embodiments, the indicator can be configured to provide either a visual indication of the amount of rotation or act as a positive stop. In yet other embodiments, a twisting apparatus does not include an indicator.

Figure 20:
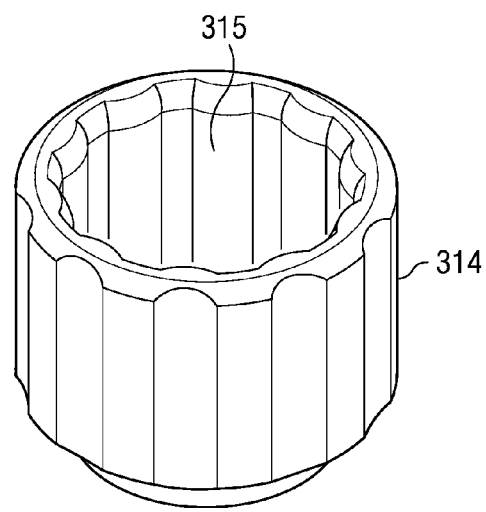
FIGS. 20 through 22 show a perspective view, a top view and a cross-sectional view, respectively, of a coupler portion of the medical device shown in FIG. 3.
Figure 21:
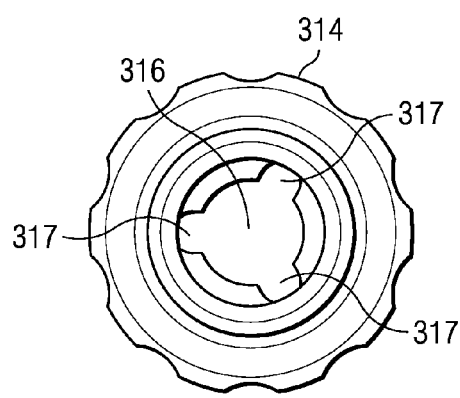
Figure 22:
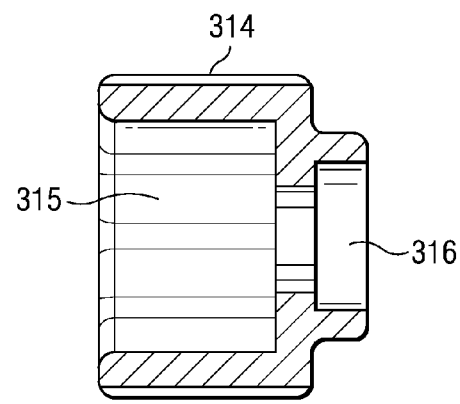

As previously discussed, the distal end portion 326 of the first member 320 is coupled to the catheter assembly 302 via coupler 314 such that the first member 320 cannot move relative to the catheter assembly 302. As shown in FIGS. 20 through 22, the coupler 314 has a first opening 315 configured to matingly receive a portion of the luer cap 310 of the catheter assembly 302. Similarly, the coupler 314 has a second opening 316 configured to receive the distal end portion 326 of the first member. The second opening 316 further defines three slots 317 configured to receive and mate with corresponding mounting tabs 328 on the first member 320 (see FIGS. 9 through 11). In this manner, the catheter assembly 302 and the actuator 300 can be keyed together such that the first member 320 cannot move relative to the catheter assembly 302.

In some embodiments, the first member 320 is fixedly coupled to the catheter assembly 302. For example, in some embodiments, the mounting tabs 328 are bonded into the slots 317 using known bonding techniques, such as an adhesive, a chemical bond, an RF weld or the like. In some embodiments, for example, the mounting tabs 328 are bonded into the slots 317 using a cyanoacrylate adhesive. In other embodiments, the first member can be removably coupled to the catheter, such as, for example, by a threadedly coupling. In yet other embodiments, the first member can be removably coupled to the catheter via a quick-connect fitting. In this manner, the twisting apparatus can be used repeatedly.

Although the catheter and the twisting apparatus are shown and described as being separate components, in some embodiments, the functionality of the twisting apparatus as described herein can be incorporated into a single component. In other embodiments, certain functionality of the catheter as described herein can be included in the twisting assembly and vice versa.

As previously discussed, the second member 360 includes a pawl portion 361 and a housing portion 372. As shown in FIGS. 12 through 17, the pawl portion 361 is a separate component that is configured to be fixedly coupled to the proximal end portion 375 of the housing portion 372. The pawl portion 361 includes four flange portions 367, each of which includes a mounting pin 366. The proximal end portion 375 of the housing portion 372 includes four corresponding recessed mounting areas 382, each of which includes a bore 365 configured to receive the mounting pins 366. In some embodiments, pins 366 are crush pins configured to have an interference fit with the bores 365, thereby causing the pawl portion 361 to be fixedly coupled to the housing portion 372 when pressed into place. In other embodiments, the pins can be bonded into their corresponding bores. In yet other embodiments, the pawl portion is coupled to the housing portion without the aid of mating pins and bores. For example, in some embodiments, the pawl portion can be coupled to the housing portion by laser welding, friction welding, adhesive bonding and the like.

The components of the actuator 300 can be constructed from any material having suitable biocompatibility, optical properties and/or mechanical properties. As described above, in some embodiments, portions of the actuator 300, such as, for example, the housing portion 372 can be constructed from a clear polycarbonate. In other embodiments, portions of the twisting apparatus, such as, for example, the first member 320 and/or the second member 360 can be constructed from a polymer having high toughness and/or high impact resistance to produce sufficient wear resistance of the teeth on the pawl portion 361 and/or the teeth on the ratchet wheel 330. Examples of such materials include Nylon and acrylonitrile butadiene styrene (ABS).

Figure 24:
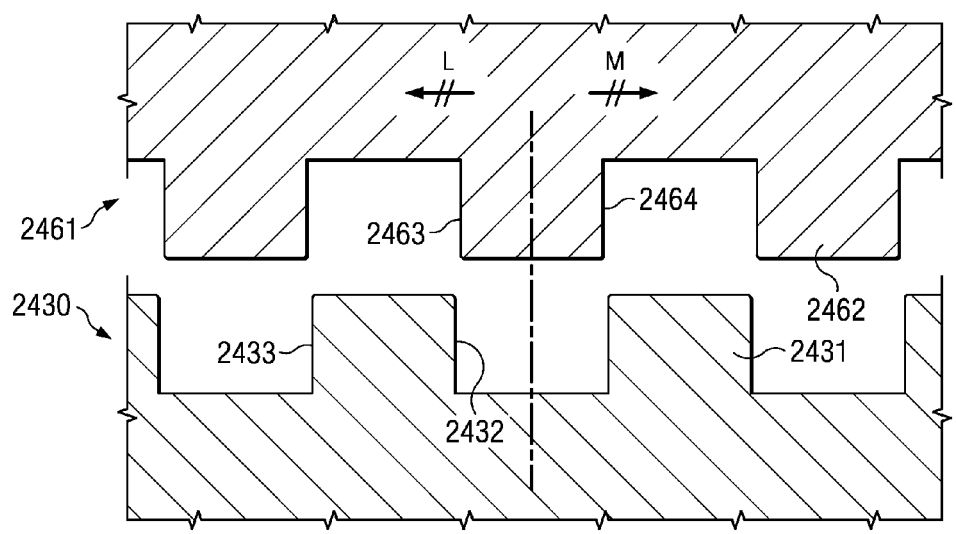
FIG. 24 is a schematic illustration showing the teeth portion of the ratchet wheel and pawl portion of a medical device according to an embodiment of the invention.

Although the twisting apparatus is shown and described as allowing unidirectional rotation when in the engaged configuration, in other embodiments a twisting apparatus can prevent any rotational motion when in the engaged configuration. One such arrangement is illustrated in FIG. 24, which shows a portion of a pawl portion 2461 and a ratchet wheel 2430 according to an embodiment of the invention. As described above, both the ratchet wheel 2430 and the pawl portion 2461 include a set of teeth 2431 and 2462, respectively. The teeth 2431 on the ratchet wheel 2430 each include a first retention surface 2432 and a second retention surface 2433. Similarly, the teeth 2462 on the pawl portion 2461 each include a first retention surface 2463 configured to mate with the first retention surface 2432 and a second retention surface 2464 configured to mate with the second retention surface 2464. All of the retention surfaces 2432, 2433, 2463, 2464 are each substantially parallel to the longitudinal axis $L_A$, thereby inhibiting motion normal to the longitudinal axis L in a direction that brings the retention surfaces into contact with each other. As such, the pawl portion 2461 cannot move relative to the ratchet wheel 2430 in either the direction as indicated by the arrow L or by the arrow M in FIG. 24 when the pawl portion 2461 is engaged with the ratchet wheel 2430. Said another way, the rotational position of a portion of the twisting apparatus and therefore the stylet is locked when the twisting apparatus is in its engaged configuration.

Figure 25:
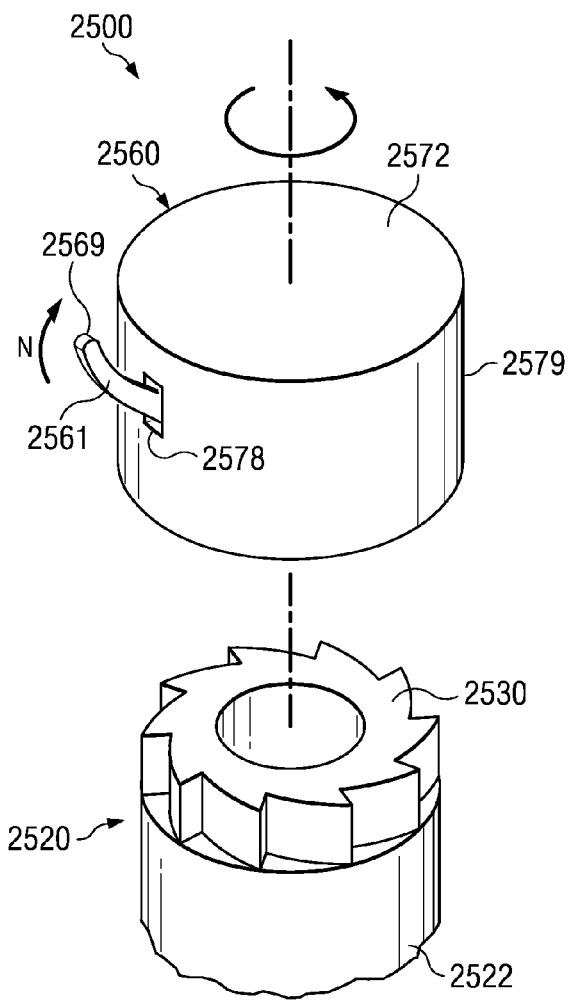
FIG. 25 is a perspective exploded view of a medical device according to an embodiment of the invention.
Figure 26:
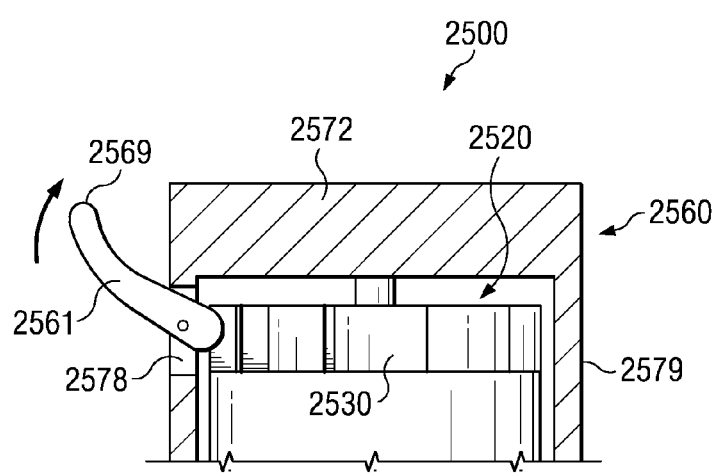
FIG. 26 is a cross-sectional view of the medical device shown in FIG. 25.
Figure 30:
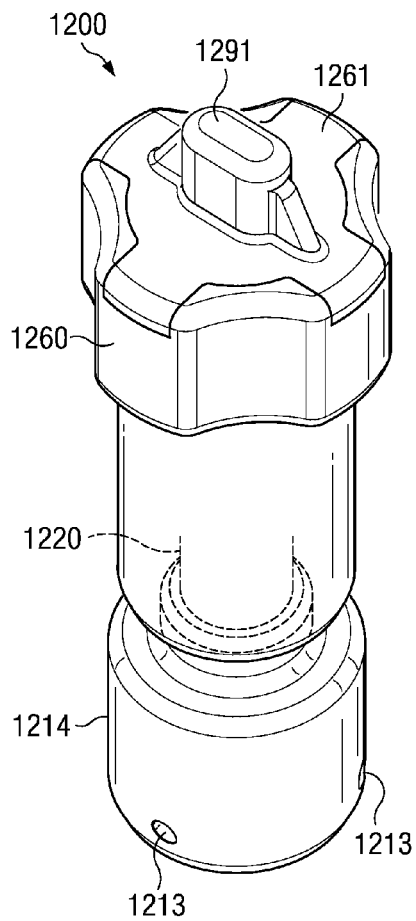
FIG. 30 is a perspective view of a twisting apparatus according to an embodiment of the invention.

Although the twisting apparatus is shown and described as having a ratchet wheel having teeth disposed on an end face of the first member and a corresponding pawl portion on the second member, in other embodiments, the ratchet mechanism can be located in any suitable position. One such arrangement is illustrated in FIGS. 25 and 26, which show a perspective exploded view and a cross-sectional view, respectively, of a portion of a twisting apparatus 2500 according to an embodiment of the invention. The twisting apparatus 2500 includes a first member 2520 and a second member 2560 disposed about the first member 2520. The first member 2520 and second member 2560 are similar to the first member 2320 and second member 2360 shown and described above. The first member 2520 differs, however, in that it includes a ratchet wheel 2530 disposed on a side surface 2522 of the first member 2520. Similarly, the second member 2560 includes a pawl portion 2561 disposed adjacent a side wall 2579 of the housing portion 2572 of the second member 2560. The second member 2560 includes a biasing member (not shown), such as a torsional spring, configured to maintain the engagement between the pawl portion 2561 and the ratchet wheel 2530. As illustrated, the pawl portion 2561 includes an end portion 2569 that extends through an opening 2578 in the side wall 2579 of the housing portion 2572. In this manner, a user can pivot the pawl portion 2561 in the direction of the arrow marked N to place the twisting apparatus 2500 in its disengaged configuration.

Although the actuators are shown and described as having a ratchet wheel with a set of teeth and a corresponding pawl portion having a set of teeth, in other embodiments, the ratchet wheel and/or the pawl portion can include only a single detent mechanism. One such arrangement is illustrated in FIGS. 25 and 26, which show a twisting apparatus 2500 including a second member 2560 having a pawl portion 2561 having a single protrusion. Another such arrangement is illustrated in FIG. 27, which shows an exploded view of a twisting apparatus 2600 including a first member 2620 and a second member 2660 disposed about the first member 2620. As described above, the first member 2620 defines a lumen 2623 through which a portion of a stylet (not illustrated) can be disposed such that the stylet can rotate about longitudinal axis L relative to the first member 2620. The side surface 2622 of the first member 2620 defines an opening 2670. The second member 2660, which is configured to engage an end portion of a stylet (not shown) as described above, includes a pawl portion 2661 disposed through an opening 2678 in a side wall 2679 of the second member 2660. The pawl portion 2661 includes a first end portion 2669 that extends outside of the second member 2660, and a second end portion (not shown) disposed within the second member 2660 and configured to engage the opening 2670. The second member 2660 also includes a biasing member (not shown) configured to bias the pawl portion 2661 to engage the side surface 2622 of the first member 2620.

In use, when the second portion 2660 is rotated relative to the first portion 2620, as indicated by the arrows marked P and Q, the pawl portion 2661 will engage the opening 2670 as the opening 2670 becomes aligned with the second end portion of the pawl portion 2661. Because the retention surfaces defined by the opening 2670 are substantially parallel to the longitudinal axis L, when the pawl portion 2661 is engaged with opening 2670, the second member 2660 is prevented from rotating about the longitudinal axis L in either direction (as indicated by the arrows P or Q). In this manner, the second member 2660 and therefore the stylet can be rotated one turn at which point the pawl portion 2661 will engage the opening 2670 preventing further rotation. When additional rotation of the second member 2660 is desired, a user can pivot the pawl portion 2661 in the direction of the arrow marked R to overcome the force exerted by the biasing member and place the twisting apparatus 2600 in its disengaged configuration, thereby allowing the second member 2660 to rotate relative to the first member 2620.

In some embodiments, a twisting apparatus can include multiple ratchet wheels and/or pawl portions of the types shown and described above. For example, in some embodiments, a twisting apparatus can include a first ratchet mechanism configured to allow a portion (i.e., a second member) of the twisting apparatus to be rotated when engaged and a second ratchet mechanism configured to prevent rotation the portion when engaged. In this arrangement, a portion of the twisting apparatus (i.e., a second member) can be rotated over a certain angular distance, such as for example, one turn, at which point the second ratchet mechanism can prevent further rotation. In this manner, a user can have greater control over the rotation of a medical device. Said another way, one ratchet mechanism can control gross rotation and the other ratchet mechanism can control fine rotation.

Returning now to the actuator 300, FIG. 28 shows a front view of the stylet 304. As described above, the stylet 304 includes a distal end portion 307 and a proximal end portion 306. As described above, the engagement portion 308 at the proximal end portion 306 of the stylet 304 is received by the actuator 300. This arrangement allows torque from the actuator 300 to be transmitted along the stylet 304 and to the expandable member 305 such that at least a portion of the expandable member 305 can be twisted about the stylet 304. Similarly, because the actuator 300 is coupled to the outer shaft 303, the outer shaft 303 is also subject to torsional stress.

The ability of the outer shaft 303 and/or the stylet 304 to withstand the torsional load applied by the actuator 300 can be characterized by an angle of twist $\phi$ and/or a shearing strain $\gamma$, as shown in FIG. 29. Although FIG. 29 shows only a portion of the stylet 304 for clarity, similar characteristics are applicable to the outer shaft 303 and/or any other shaft, rod or elongate member that can be included within the catheter assembly 302. The angle of twist $\phi$ of the stylet 304 is the angular displacement of the distal end portion 307 of the stylet 304 relative to the proximal end portion 306 of the stylet 304, as measured within a plane normal to the longitudinal axis LA (e.g., the end surface), when the stylet 304 is subjected to a torsional load (shown by arrow TTT in FIG. 29). Similarly, the shearing strain $\gamma$ of the stylet 304 is the angular displacement of the distal end portion 307 of the stylet 304 relative to the proximal end portion 306 of the stylet 304, as measured in a surface parallel to the longitudinal axis $L_A$, when the stylet 304 is subjected to the torsional load TTT. As the angle of twist and/or the shearing strain decreases, a structure is considered more torsionally rigid.

In some embodiments, the stylet 304 is configured to have an angle of twist $\phi$ between the proximal end portion 306 and the distal end portion 307 of less than three hundred sixty degrees (i.e. one revolution) when at least a portion of the expandable member 305 is twisted about the longitudinal axis L of the stylet 304 through four revolutions. In other embodiments, the stylet 304 is configured to have an angle of twist $\phi$ between the proximal end portion 306 and the distal end portion 307 of less than one hundred eighty degrees (i.e., a half revolution) when at least a portion of the expandable member 305 is twisted about the longitudinal axis L of the stylet 304 through four revolutions. In yet other embodiments, the stylet 304 is configured to have an angle of twist $\phi$ between the proximal end portion 306 and the distal end portion 307 of less than ninety degrees (i.e., a half revolution) when at least a portion of the expandable member 305 is twisted about the longitudinal axis L of the stylet 304 through four revolutions. In yet other embodiments, the stylet 304 is configured to have an angle of twist $\phi$ between the proximal end portion 306 and the distal end portion 307 of less than sixty degrees (i.e., a half revolution) when at least a portion of the expandable member 305 is twisted about the longitudinal axis L of the stylet 304 through four revolutions. In yet other embodiments, the stylet 304 is configured to have an angle of twist $\phi$ between the proximal end portion 306 and the distal end portion 307 of less than thirty degrees (i.e., a half revolution) when at least a portion of the expandable member 305 is twisted about the longitudinal axis L of the stylet 304 through four revolutions.

Similarly, in some embodiments, the outer shaft 303 is configured to have an angle of twist $\phi$ between the proximal end portion 306 and the distal end portion 307 of less than three hundred sixty degrees (i.e. one revolution) when at least a portion of the expandable member 305 is twisted about the longitudinal axis L of the stylet 304 through four revolutions. In other embodiments, the outer shaft 303 is configured to have an angle of twist $\phi$ between the proximal end portion 306 and the distal end portion 307 of less than one hundred eighty degrees (i.e., a half revolution) when at least a portion of the expandable member 305 is twisted about the longitudinal axis L of the stylet 304 through four revolutions. In yet other embodiments, the outer shaft 303 is configured to have an angle of twist $\phi$ between the proximal end portion 306 and the distal end portion 307 of less than ninety degrees (i.e., a half revolution) when at least a portion of the expandable member 305 is twisted about the longitudinal axis L of the stylet 304 through four revolutions. In yet other embodiments, the outer shaft 303 is configured to have an angle of twist $\phi$ between the proximal end portion 306 and the distal end portion 307 of less than sixty degrees (i.e., a half revolution) when at least a portion of the expandable member 305 is twisted about the longitudinal axis L of the stylet 304 through four revolutions. In yet other embodiments, the outer shaft 303 is configured to have an angle of twist $\phi$ between the proximal end portion 306 and the distal end portion 307 of less than thirty degrees (i.e., a half revolution) when at least a portion of the expandable member 305 is twisted about the longitudinal axis L of the stylet 304 through four revolutions.

Moreover, because the distal end portion 307 of the stylet 304 and the outer shaft 303 are inserted into the patient's body, compression and/or buckling forces applied during insertion can also transmitted along the stylet 304 and/or the outer shaft 303. Other forces applied to the stylet 304 and/or the outer shaft 303 can include forces produced by the inflation pressure and/or forces produced as the expandable member 305 is moved from the expanded configuration to the collapsed configuration (e.g., forces produced by applying a negative pressure to portions of the catheter assembly 302).

Accordingly, the stylet 304 and/or the outer shaft 303 can be constructed from any material suitable for withstanding the forces generated during the operation of the medical device 301. In some embodiments, for example, the stylet 304 and/or the outer shaft 303 can be constructed from a biocompatible stainless steel having a high tensile strength and/or a high shear modulus. In other embodiments, the stylet 304 and/or the outer shaft 303 can be constructed from a high-strength polymer. In yet other embodiments, the stylet 304 and/or the outer shaft 303 can be constructed from a composite material, such as, for example, a polymer including reinforcing glass fibers.

Although composite materials, such as glass reinforced polymers, can offer improved performance, the composite materials used to construct the stylet 304 and/or the outer shaft 303 need not be limited to such traditional materials. For example, in some embodiments, the stylet 304 and/or the outer shaft 303 can be constructed from extruded biocompatible polymers that are reinforced with nano-particles. For example, in some embodiments, the stylet 304 and/or the outer shaft can be constructed from a blend of Nylon 12, one or more colorants and nano-particle fillers. Nano-particles can include any inorganic mineral having a high aspect ratio (i.e., a length to width ratio of approximately between 300:1 and 1500:1) with at least one dimension having a size in the nanometer range. In some embodiments, for example, nano-particles can include hydrotalcite, montmorillonite and/or mica fluoride.

Because nano-particles have a size that approximates the size of the polymer molecules, the nano-particles can interact with the polymer at the molecular level, which can immobilize portions of the polymer chain. Such immobilization can lead to significant improvements in strength, hardness and/or chemical resistance. In some embodiments, the nano-particles can be combined with a cross-linking agent, such as, for example, trallylisocyanumrate, to promote such molecular interaction. In some embodiments, the mixture of nano-particles and the cross-linking agent can be exposed to irradiation to promote such molecular interaction.

Although the cross-sections of the stylet 304 and the outer shaft 303 are shown and described as being circular, in some embodiments, the cross-section of the stylet 304 and/or the outer shaft 303 can be of any suitable shape. For example, in some embodiments, the cross-section of the stylet 304 and/or the outer shaft 303 can have a rectangular shape. Such non-circular shapes can improve mechanical characteristics of the stylet 304 and/or the outer shaft 303, such as, for example, the column strength, the resistance to bending and/or the resistance to bending in torsion. Said another way, the cross-sectional shape of the stylet 304 and/or the outer shaft 303 can be selected to have a large shear modulus, thereby increasing the resistance to angular deflection.

Although the first member 320 of the actuator 300 is shown in FIGS. 4 and 5 and described above as being fixedly coupled catheter assembly 302, in some embodiments, the first member can be coupled to the catheter assembly in a manner that allows longitudinal movement between the first member and the catheter assembly. For example, FIGS. 30-34 show a portion of a twisting apparatus 1200 according to an embodiment of the invention in which a first member 1220 is coupleable to a catheter assembly (not shown in FIGS. 30-34) such that the first member 1220 can move longitudinally relative to the catheter assembly. In this manner, when a rotational force is applied to a second member 1260, the resultant longitudinal force produced by the angled surfaces of a pawl portion 1261 and a ratchet wheel 1230 causes the second member 1260 to move proximally and the first member 1220 to move distally. In some embodiments, the longitudinal movement of the first member 1220 can result in a twisting mechanism 1200 in which the mating teeth on the ratchet wheel 1230 and pawl portion 1261 engage each other consistently regardless of the number of turns through which the pawl portion 1261 has been twisted. Said another way, by allowing longitudinal movement of the first member 1220, the mating teeth on the ratchet wheel 1230 and the pawl portion 1261 can be less likely to slip when in the engaged configuration.

In the illustrated twisting apparatus 1200, the second member 1260 is disposed about the first member 1220. The first member 1220 includes a distal end portion 1226 and a proximal end portion 1227. As described above, the proximal end portion 1227 of the first member 1220 includes a ratchet wheel 1230 removably engagable with a pawl portion 1261 of the second member 1260. The second member 1260 includes a housing portion 1272 and the pawl portion 1261 that is removably engagable with the ratchet wheel 1230 of the first member 1220. The pawl portion 1261 of the second member 1260 is fixedly coupled to the housing portion 1272. The pawl portion 1261 includes an extension portion 1291 that defines an opening 1281 within which a portion of a stylet (not shown in FIGS. 30-34) is received. As described above, the opening 1281 has a long, narrow shape such that when the second member 1260 rotates, the stylet will engage the sides of the opening 1281 thereby causing the stylet to rotate with the second member 1260. Moreover, because the stylet is not fixedly coupled to the second member 1260, the second member 1260 can move axially relative to the stylet and/or the first member 1220.

Figure 31:
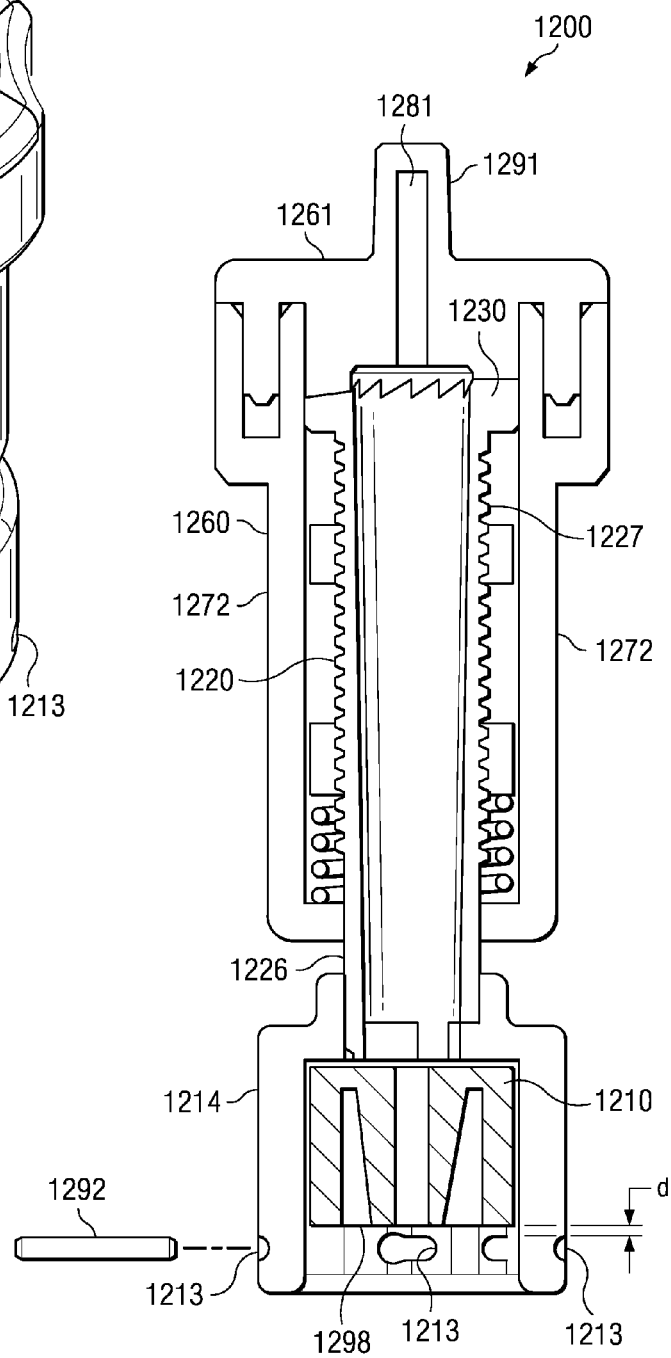
FIG. 31 is a cross-sectional view of the twisting apparatus shown in FIG. 30.
Figure 32:
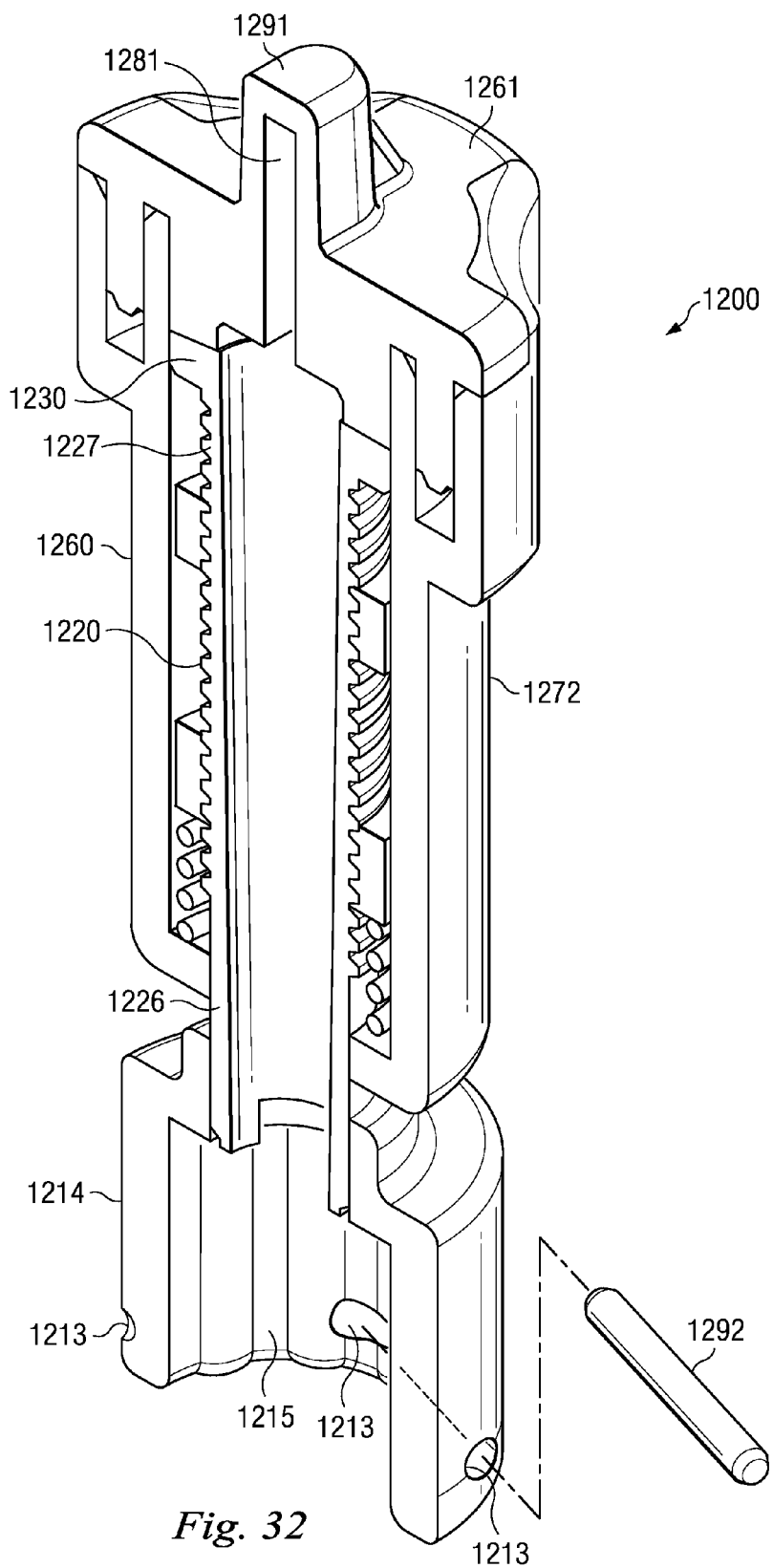
FIG. 32 is a cross-sectional perspective view of the twisting apparatus shown in FIG. 30.

In contrast to the actuator 300 shown and described above, the distal end portion 1226 of the first member 1220 can be movably coupled to a catheter assembly via coupler 1214, such that the first member 1220 can move longitudinally relative to the catheter assembly. Similar to the coupler 314 described above, the coupler 1214 has a first opening 1215 configured to matingly receive a portion of a luer cap 1210 of the catheter assembly (not shown in FIGS. 30-34). The coupler 1214 defines four openings 1213 through which two connecting pins 1292 (only one pin of the four pins is shown in FIGS. 31 and 32) can be disposed. Each pin 1292 is disposed within a corresponding pair of openings 1213 such that the distal end portion 1298 of the luer cap 1210 is spaced apart from the pins 1292 by a distance d, as shown in FIG. 31. In this manner, the coupler 1214 (and therefore, the first member 1220) can move longitudinally relative to the luer cap 1210 by the distance d.

Figure 33:
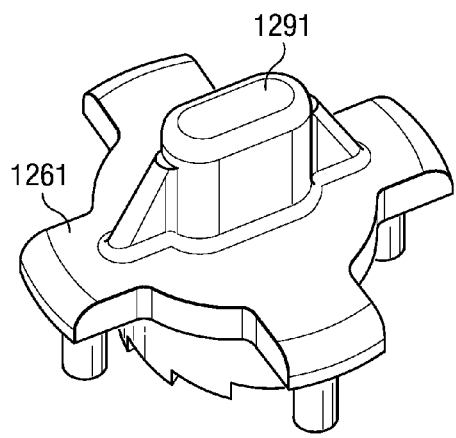
FIG. 33 is a perspective view of a portion of the twisting apparatus shown in FIG. 30.
Figure 34:
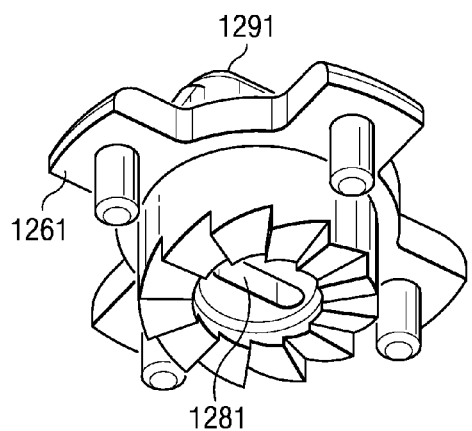
FIG. 34 is a perspective view of a portion of the twisting apparatus shown in FIG. 30.
Figure 35:
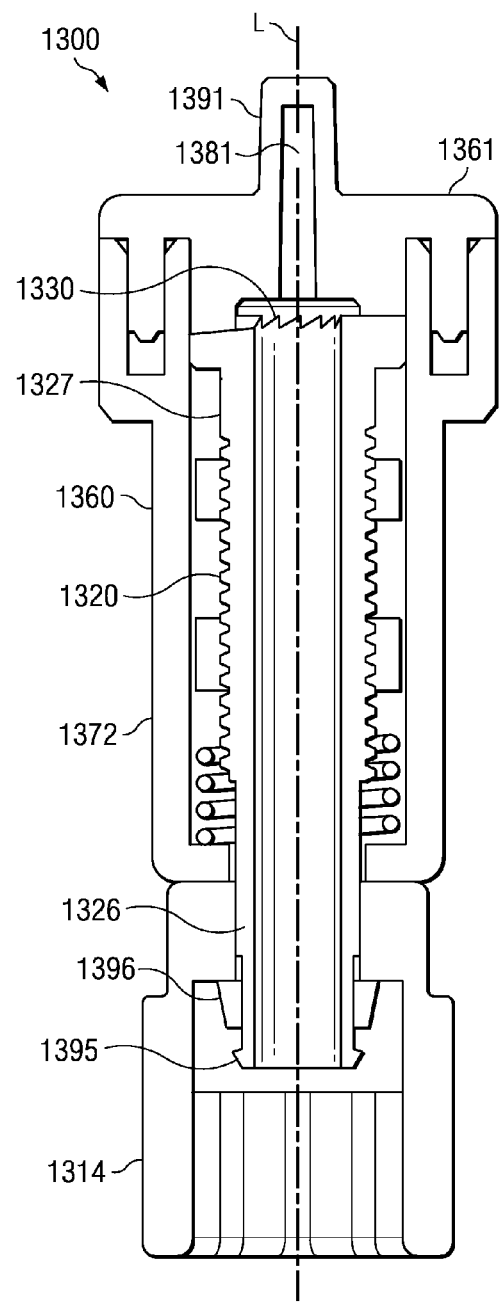
Figure 38:
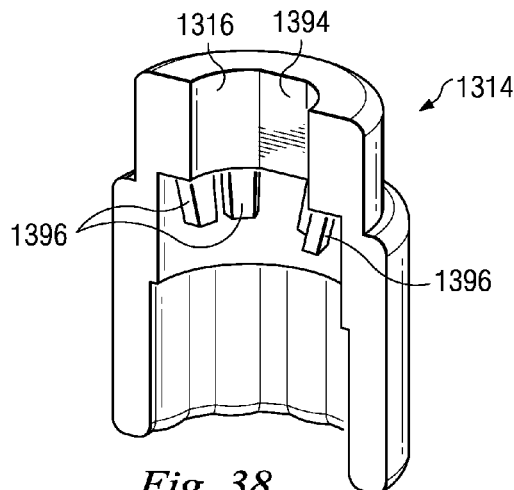
FIG. 38 is a perspective view of a portion of the twisting apparatus shown in FIGS. 35 and 36.

As shown in FIGS. 33 and 34, the extension portion 1291 of the pawl portion 1261 extends above the proximal surface of the pawl portion 1261. In this manner, the longitudinal length of the opening 1281 can be increased to allow a greater amount longitudinal movement of the stylet (not shown in FIGS. 33 and 34) within the opening. In other embodiments, an extension portion of the pawl portion can extend distally into the lumen defined by the first member 1220 of the twisting apparatus 1200.

Although the pins 1292 are shown as being disposed within the openings 1213 such that the distal end portion 1298 of the luer cap 1210 is spaced apart from the pin 1292 by a distance d, in other embodiments, the pins 1292 can be disposed within the openings 1213 such that substantially no space exists between the distal end portion 1298 of the luer cap 1210 and the pins 1213. In such embodiments, the connecting pins 1292 can be constructed from a flexible material, such as, for example, stainless steel spring wire, to allow the connecting pins 1292 to bend when the coupler 1214 (and therefore, the first member 1220) is moved longitudinally relative to the luer cap 1210. In this manner, when a longitudinal force, such as, for example, the resultant force produced when the twisting apparatus 1200 is rotated, is applied to the first member 1220 of the twisting apparatus 1200, the first member 1220 can move longitudinally relative to the catheter assembly.

The range of motion of the first member 1220 relative to the catheter assembly and/or the force used to move the first member 1220 relative to the catheter assembly is a function of the distance d between the connecting pins 1292 and the luer cap 1210 and the flexibility of the connecting pins 1292. In some embodiments, for example, the connecting pins 1292 can be configured to allow the first member 1220 to move approximately a distance corresponding to the height of the teeth on the ratchet wheel and pawl. In some embodiments, for example, the openings 1213 and connecting pins 1292 can be configured to allow the first member 1220 to move between 1 and 3 mm relative to the catheter assembly. In other embodiments, for example, the openings 1213 and connecting pins 1292 can be configured to allow the first member 1220 to move a distance greater than the height of the teeth on the ratchet wheel and pawl.

Although the coupler 1214 is shown and described as being movably coupled to the luer cap via connecting pins 1292 that can be flexible, in other embodiments, the connecting pins need not be flexible. For example, in some embodiments, a coupler can include slotted openings through which rigid pins are disposed to connect the coupler to the luer cap. In such an arrangement the rigid pins can be coupled to the luer cap, for example, by being press fit into an opening defined by the luer cap, thereby allowing the coupler to move relative to the luer cap as the slotted openings move about the rigid pins. In other embodiments, the rigid pins can be fixedly coupled to the coupler and the luer cap can include corresponding slotted openings, within which the pins can move.

Although the twisting apparatus 1200 is shown and described above as allowing relative motion between the first member 1220 and a catheter assembly via motion of the coupler with respect to the luer cap, in other embodiments, any suitable mechanism for permitting longitudinal motion between the first member and a catheter assembly can be employed. For example, FIGS. 35-38 show a twisting mechanism 1300 having a first member 1320 that is movably coupled to a coupler 1314.

Similar to the twisting apparatuses shown and described above, the illustrated twisting apparatus 1300 includes a first member 1320 and a second member 1360 disposed about the first member 1320. The second member 1360 includes a housing portion 1372 and the pawl portion 1361 that is removably engagable with the ratchet wheel 1330 of the first member 1320. The pawl portion 1361 of the second member 1360 is fixedly coupled to the housing portion 1372. The pawl portion 1361 includes an extension portion 1391 that defines an opening 1381 within which a portion of a stylet (not shown in FIGS. 35-38) is received.

The first member 1320 includes a distal end portion 1326 and a proximal end portion 1327. As described above, the proximal end portion 1327 of the first member 1320 includes a ratchet wheel 1330 removably engagable with a pawl portion 1361 of the second member 1360. As described in more detail herein, the distal end portion 1326 is movably coupled to the coupler 1314, which is fixedly coupled to a catheter assembly (not shown in FIGS. 35-38). In this manner, the first member 1320 can move longitudinally relative to the catheter assembly.

In use, when the twisting apparatus 1300 is in its first (e.g., engaged) configuration (see FIGS. 35 and 38), the second member 1360 can be rotated relative to the first member 1320 about the longitudinal axis L in a direction as indicated by arrow P in FIG. 36. As described above, the rotational force applied to the pawl portion 1361 produces a resultant force $F_{L1}$ that acts on the second member 1360 and an equal and opposite resultant force $F_{L2}$ that acts on the first member 1320 portion parallel to the longitudinal axis L and in the proximal direction. The resultant forces $F_{L1}$ and $F_{L2}$ cause the pawl portion 1361 to move proximally and/or the first member 1320 to move distally, as shown in FIG. 36. In this manner, the pawl portion 1361 can be rotated relative to the ratchet wheel 1330 in the direction P in a unidirectional, controlled and/or incremental fashion, as described above.

The distal end portion 1326 of the first member 1320 includes two flatted portions 1393. The coupler 1314 includes corresponding flatted portions 1394 within the opening 1316. This arrangement prevents relative rotation between the first member 1320 and the coupler 1314. Similarly, the coupler 1314 includes multiple retention tabs 1396 that engage a retention lip 1395 on the distal end portion 1326 of the first member 1320 (see FIG. 35). In this manner, the range of motion of the first member 1320 relative to the catheter assembly can be limited.

Figure 39:
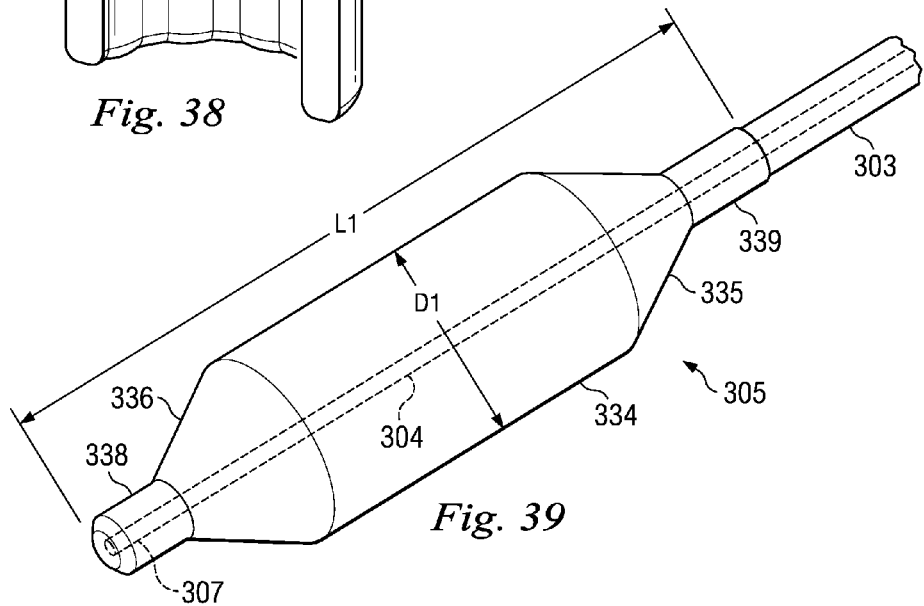
FIG. 39 is a perspective view of the expandable member shown in FIG. 3 in an expanded configuration.

Other aspects of the invention include various configurations of the expandable member. Various methods for improving the structural integrity of expandable member are also disclosed herein. Details of the expandable member 305 are now discussed with reference to FIG. 39. FIG. 39 is a perspective view of the expandable member 305 in its expanded configuration. The expandable member 305 includes a distal tapered portion 336, a proximal tapered portion 335 and a central portion 334 disposed between the distal tapered portion 336 and the proximal tapered portion 335. The proximal tapered portion 335 terminates in a proximal bond portion 339 that is coupled to the outer shaft 303. Similarly, the distal tapered portion 336 terminates in a distal bond portion 338 that is coupled to the distal end portion 307 of the stylet 304.

The central portion 334 of the expandable member 305 is substantially cylindrical in shape and has a diameter D1 and a length L1. The distal tapered portion 336 and the proximal tapered portion 335 are each substantially conical in shape. The total volume of the expandable member 305 when in the expanded configuration is a function of the diameter D1, the length L1 and the configuration of the tapered portions 336, 335. In some embodiments, the diameter D1 can be between 8 mm and 20 mm (0.315 in. and 0.787 in.). In other embodiments, the diameter D1 can be between 8 mm and 13 mm (0.315 in. and 0.512 in.). In yet other embodiments, the diameter D1 can be approximately 12 mm (0.472 in.). Similarly, in some embodiments, the length L1 can be up to 30 mm (1.181 in.). In other embodiments, the length L1 can be approximately 22 mm (0.866 in.). The volume of the expandable member 305 when in the expanded configuration can range from 0.5 cubic centimeters to 10 cubic centimeters. In some embodiments, the volume of the expandable member 305 when in the expanded configuration is approximately 3.5 cubic centimeters.

Although shown as having a substantially cylindrical shape, in some embodiments, the expandable member 305 can be configured to assume any suitable shape and/or size when in the expanded configuration. For example, in some embodiments, an expandable member can have a shape that approximates the inner shape of the bone structure in which it is to be deployed, as described in U.S. Pat. No. 6,981,981 and incorporated herein by reference in its entirety. In other embodiments, an expandable member can have various portions each of which has a different shape, thereby resulting in an expandable member having a discontinuous shape. In yet other embodiments, an expandable member can have an asymmetrical shape, such as, for example, a kidney bean shape, an asymmetrical ring shape or the like.

Figure 40:
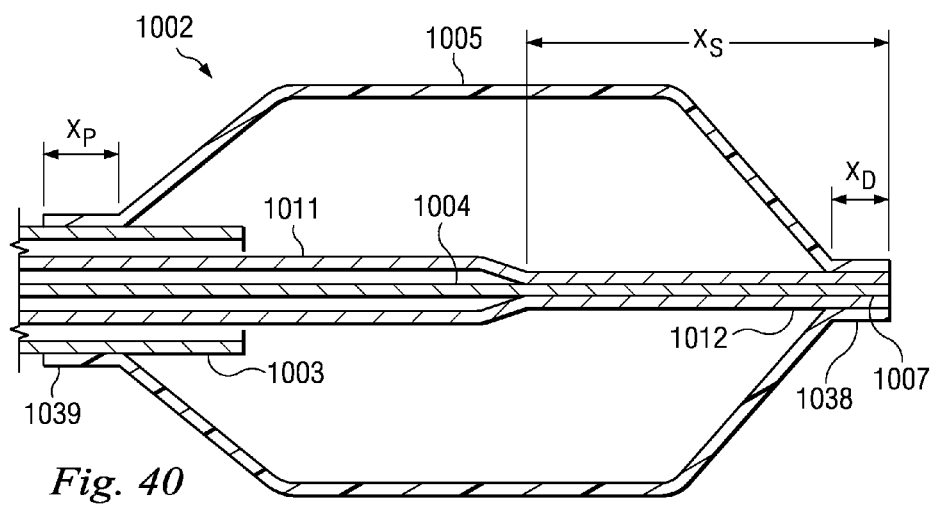
FIG. 40 is a schematic illustration of a portion of a catheter assembly according to an embodiment of the invention having an outer shaft, an inner shaft and a stylet.

Although the catheter assembly 302 is shown and described above as including a stylet 304 disposed within an outer shaft 309 wherein the distal end 307 of the stylet 304 is coupled to the distal bond portion 338 of the expandable member 305, in some embodiments, a catheter can include any number of shafts, tubes and/or other components. For example, FIG. 40 shows a portion of a catheter assembly 1002 having an outer shaft 1003 and an inner shaft 1011 according to an embodiment of the invention. The outer shaft 1003 defines a lumen through which a portion of the inner shaft 1011 is rotatably disposed. Similarly, the inner shaft 1011 defines a lumen through which a portion of a stylet 1004 is disposed. In some embodiments, the inner shaft 1011 can be constructed from similar materials from which the outer shaft 1003 and/or the stylet 1004 are constructed. In some embodiments, for example, the inner shaft can be constructed from Nylon 12.

The catheter assembly 1002 includes an expandable member 1005 of the type shown and described herein. A proximal bond portion 1039 of the expandable member 1005 is coupled to the outer shaft 1003 over a distance $X_P$ to form a fluid-tight seal. Similarly, a distal bond portion 1038 of the expandable member 1005 is coupled to a distal portion 1012 of the inner shaft 1011 over a distance $X_D$ to form a fluid-tight seal. The distal portion 1012 of the inner shaft 1011 is coupled to the distal end portion 1007 of the stylet 1004 over a distance $X_S$. In this manner, the distal bond portion 1038 of the expandable member 1005, the inner shaft 1011 and the stylet 1004 are joined together to form a fluid-tight seal. As used herein, the term "fluid-tight seal" refers to a seal that substantially prevents a liquid and/or a gas from passing therethrough. For example, in some embodiments, a fluid-tight seal can prevent a liquid inflation medium, such as saline, from passing therethrough, while allowing a gas to pass therethrough. In other embodiments, a fluid-tight seal can prevent both a liquid and a gas from passing therethrough.

As previously discussed, in some embodiments, the catheter assembly 1002 includes an actuator (not shown in FIG. 40) to twist at least a portion of the expandable member 1005 about the stylet 1004. In this manner, a profile (e.g., the outer diameter) of the expandable member 1005 can be minimized when the expandable member 1005 is in its collapsed configuration (see e.g., FIG. 42) to facilitate insertion and/or removal of the expandable member 1005 via a cannula. Accordingly, as described above, the components of the catheter assembly 1005, including the regions where the expandable member 1005 is coupled to the outer shaft 1003 and/or the inner shaft 1011, can be subject to torsional load transmitted by the actuator.

In some embodiments, for example, the proximal bond portion 1039 of the expandable member 1005 is coupled to the outer shaft 1003 such that the proximal bond portion 1039 does not rotate relative to the distal end portion of the outer shaft 1003 (e.g., the proximal bond portion 1039 remains securely coupled to the outer shaft 10030) when at least a portion of the expandable member 1005 is twisted about the inner shaft 1011 and/or the stylet 1004 through at least four revolutions. In some embodiments, the proximal bond portion 1039 of the expandable member 1005 is coupled to the outer shaft 1003 such that a fluid-tight seal is maintained between the proximal bond portion 1039 and the distal end portion of the outer shaft 1003 when at least a portion of the expandable member 1005 is twisted about the inner shaft 1011 and/or the stylet 1004 through at least four revolutions. In other embodiments, the proximal bond portion 1039 of the expandable member 1005 is coupled to the outer shaft 1003 such that a fluid-tight seal is maintained between the proximal bond portion 1039 and the distal end portion of the outer shaft 1003 when at least a portion of the expandable member 1005 is twisted about the inner shaft 1011 and/or the stylet 1004 through at least six revolutions.

Similarly, in some embodiments, the distal bond portion 1038 of the expandable member 1005 is coupled to the distal portion 1012 of the inner shaft 1011 such that the distal bond portion 1038 does not rotate relative to the distal portion 1012 of the inner shaft 1011 when at least the portion of the expandable member 1005 is twisted about the inner shaft 1011 and/or the stylet 1004 through at least four revolutions. In some embodiments, the distal bond portion 1038 of the expandable member 1005 is coupled to the distal portion 1012 of the inner shaft 1011 such that a fluid-tight seal is maintained between the distal bond portion 1038 and the distal portion 1012 of the inner shaft 1011 when at least the portion of the expandable member 1005 is twisted about the inner shaft 1011 and/or the stylet 1004 through at least four revolutions. In other embodiments, the distal bond portion 1038 of the expandable member 1005 is coupled to the distal portion 1012 of the inner shaft 1011 such that a fluid-tight seal is maintained between the distal bond portion 1038 and the distal portion 1012 of the inner shaft 1011 when at least the portion of the expandable member 1005 is twisted about the inner shaft 1011 and/or the stylet 1004 through at least six revolutions.

The strength of the coupling between the expandable member 1005 and the outer shaft 1003 and/or the inner shaft 1011 is dependent on a wide range of parameters, which can include the manufacturing processes used to coupled the expandable member 1005 to the outer shaft 1003 and/or the inner shaft 1011, the material properties of the components being coupled and/or the axial length of the coupling ($X_P$ and $X_D$). In some embodiments, the greater the axial length of the coupling, the greater the strength (i.e., ability to withstand torsional stress) of the coupling. In some embodiments, however, the axial length of the coupling ($X_P$ and $X_D$) is minimized to increase the length that the central portion of the expandable member (see e.g., central portion 334 in FIG. 39) can extend into a bone structure. Accordingly, as described herein, the axial length of the coupling ($X_P$ and $X_D$) and the manufacturing processes used to couple the expandable member to the inner shaft and/or the outer shaft can be selected to provide the desired strength with the shortest possible axial length ($X_P$ and $X_D$).

In some embodiments, for example, the distance $X_P$ can be between 1 mm and 7 mm (0.040 in. and 0.275 in.). In other embodiments, the distance $X_P$ can be approximately 2.5 mm (0.100 in.). Similarly, in some embodiments, the distance $X_D$ can be between 1 mm and 5 mm (0.040 in. and 0.200 in.). In other embodiments, the distance $X_D$ can be approximately 3 mm (0.118 in.). In yet other embodiments, the distance $X_D$ can be approximately 2 mm (0.080 in.). Similarly, in some embodiments, the distance $X_S$ can be between 5 mm and 38 mm (0.200 in. and 1.5 in.). In other embodiments, the distance $X_S$ can correspond approximately to the length of the expandable member 1005. In yet other embodiments, the inner shaft 1011 can be coupled to the stylet 1004 at several longitudinal locations. In yet other embodiments, the inner shaft 1011 can be coupled to the stylet 1004 along the entire length of the inner shaft 1011. Said another way, in some embodiments, the inner shaft 1011 can be coupled to the stylet 1004 along the entire length of the inner shaft 1011, thereby forming a composite member configured to be coupled to the expandable member 1005 and transmit the torsional forces produced by a twisting apparatus of the type shown and described above.

In some embodiments, the stylet 1004, the inner shaft 1011 and the distal bond portion 1038 of the expandable member 1005 can be coupled together in a single manufacturing operation. In other embodiments, the stylet 1004 and the inner shaft 1011 can be coupled together in a first operation, and the distal bond portion 1038 of the expandable member 1005 and the distal portion 1012 of the inner shaft 1011 can be coupled together in a second operation. For example, in some embodiments, the stylet 1004 and the inner shaft 1011 can be coupled together using a radio frequency induction heating process (i.e., an RF bonding process) and the distal bond portion 1038 of the expandable member 1005 and the distal portion 1012 of the inner shaft 1011 can be coupled together using a laser bond process. The RF bonding process and the laser bond process are described in more detail herein.

In some embodiments, the proximal end portion of the inner shaft 1011 (not shown in FIG. 40) can be retained within a Y-connector of a catheter assembly, similar to the Y-connector 309 shown and described above with reference to FIG. 6. In this manner, the Y-connector can act as an interface for the outer shaft, the inner shaft, the inflation device and/or the twisting apparatus. In some embodiments, the proximal end portion of the inner shaft 1011 can be retained within the Y-connector such that the inner shaft 1011 rotates with the stylet 1004 relative to the outer shaft 1003 and/or the Y-connector. In other embodiments, the proximal end portion of the inner shaft 1011 can be retained within the Y-connector such that the proximal end portion of the inner shaft 1011 does not rotate with the stylet 1004. In yet other embodiments, as described above, a catheter assembly includes only one of a stylet or an inner shaft.

Figure 41:
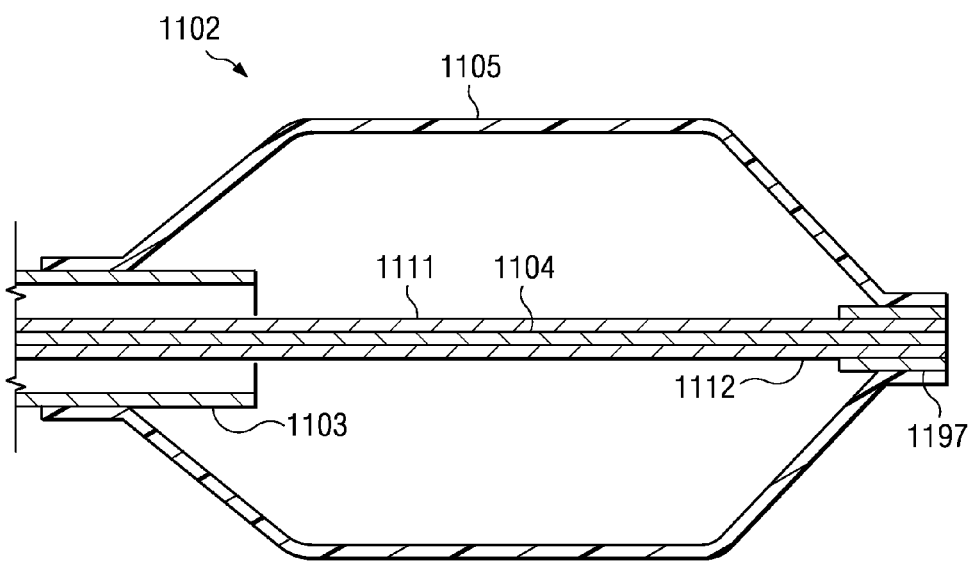
FIG. 41 is a schematic illustration of a portion of a catheter assembly according to an embodiment of the invention having an outer shaft, an inner shaft, a stylet and a sleeve.

Although the catheter 1002 is shown and described as including a stylet 1004, an inner shaft 1011 and an outer shaft 1003, in other embodiments, a catheter can include any number of shafts, tubes and/or stylets. For example, FIG. 41 shows a portion of a catheter 1102 having an outer shaft 1103, an inner shaft 1111, a stylet 1104 and a sleeve 1197 according to an embodiment of the invention. Similar to the catheter 1002 described above, the outer shaft 1103 defines a lumen through which a portion of the inner shaft 1111 is rotatably disposed. The inner shaft 1111 defines a lumen through which at least a portion of a stylet 1104 is disposed. The catheter 1102 differs from the catheter 1002, however, in that catheter 1102 includes a sleeve 1197 disposed between the expandable member 1105 and the inner shaft 1111 along the distal end portion 1112 of the inner shaft 1111. In some embodiments, the sleeve 1197 can be constructed from a polymer, such as PEBAX®, configured to enhance the strength of the distal bond (e.g., the bond between the expandable member 1105 and the inner shaft 1111). As described herein, in some embodiments, the expandable member 1105, the inner shaft 1111 and the sleeve 1197 can be collectively coupled (e.g., coupled in one process such that there is not a first coupling between the inner shaft 1111 and the sleeve 1197 and a second coupling between the sleeve 1197 and the expandable member 1105 that is separate and distinct from the first coupling).

In some embodiments, the sleeve 1197 can include a colorant for identification purposes and/or to be excited by a laser used to couple the expandable member 1105, the inner shaft 1111 and the sleeve 1197. For example, in some embodiments, the sleeve 1197 can be constructed from a polymer that includes two percent purple resin.

Although the catheters shown and described above include a stylet, in some embodiments, a catheter do not include a stylet. For example, in some embodiments, a catheter can include an outer shaft and an inner shaft of the type described above. In such embodiments, for example, the inner shaft can engage a twisting apparatus configured to rotate the inner shaft relative to the outer shaft, thereby causing the expandable member to be twisted, as described above.

Figure 42:
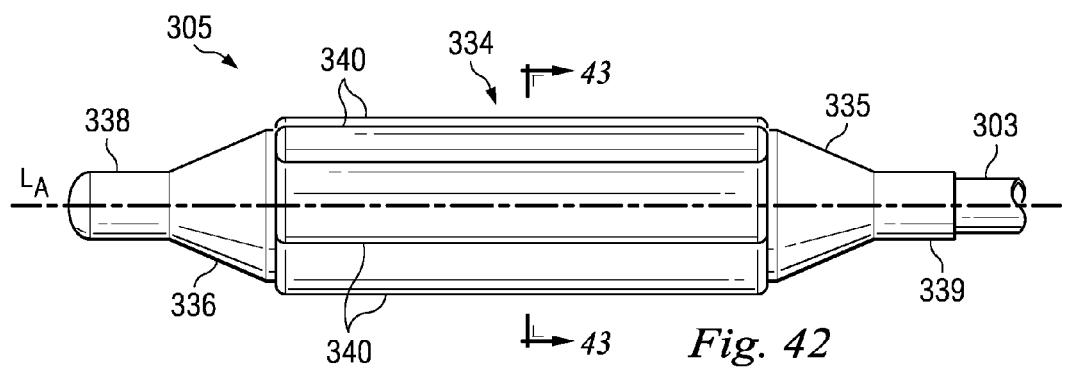
FIG. 42 is a front view of the expandable member shown in FIGS. 3 and 39 in a collapsed configuration.
Figure 43:
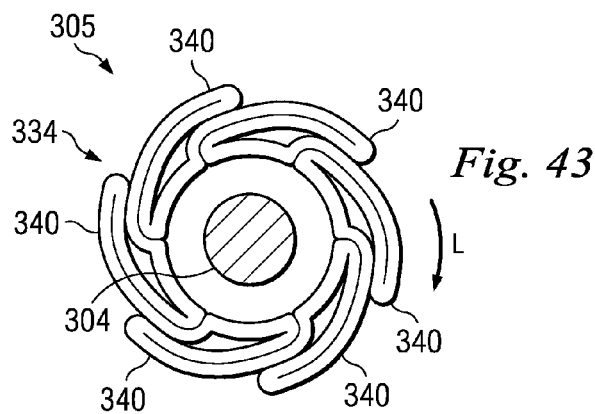
FIGS. 43 and 44 are cross-sectional views of the expandable member shown in FIG. 42 taken along line 43-43, in a twisted configuration and an untwisted configuration, respectively.
Figure 44:
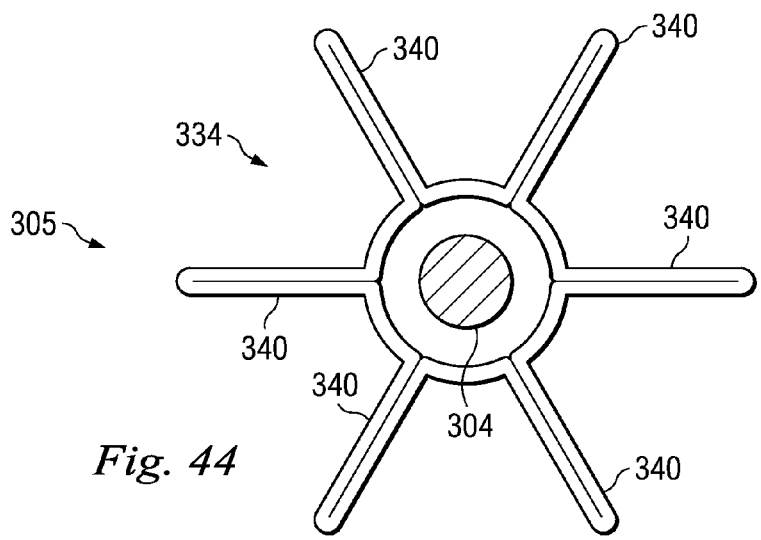

FIG. 42 shows the expandable member 305 in its collapsed configuration, with the expandable member being wrapped about the stylet 304. The expandable member 305 includes multiple pleats 340 disposed longitudinally along the central portion 334. As shown in FIGS. 43 and 44, the pleats 340 can be folded and/or wrapped circumferentially about the longitudinal axis La of the stylet 304, as indicated by the arrow L in FIG. 43, to minimize the profile (e.g., the outer diameter) of the expandable member 305 when in its collapsed configuration. In this manner, the expandable member 305 can be inserted and/or removed via a cannula. The formation of the pleats is discussed in more detail herein.

Although the expandable member 305 is shown and described as having pleats 340 along the central portion 334, in some embodiments the pleats 340 can extend along the proximal tapered portion 335 and/or the distal tapered portion 336. Similarly, the pleats 340 can be of any suitable size and/or shape. For example, in some embodiments, the pleats 340 can be non-linear. In other embodiments, the pleats 340 can be asymmetrically disposed about the central portion 334 of the expandable member 305. In yet other embodiments, an expandable member can include any number of pleats, such as three, four, five, six or more pleats.

Figure 45:
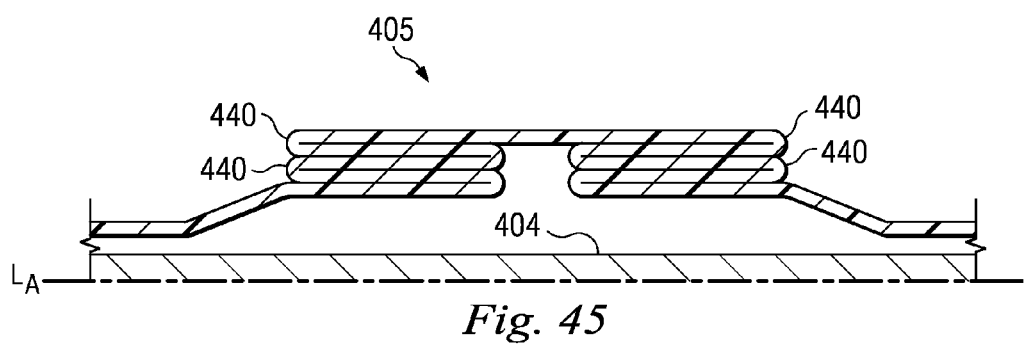
FIG. 45 is a cross-sectional view of an expandable member according to an embodiment of the invention in a collapsed configuration.

Although the pleats 340 are shown and described as being folded and/or wrapped about the longitudinal axis of the stylet 304, in other embodiments, the pleats 340 can be folded and/or wrapped about any suitable axis. For example, FIG. 45 is a cross-sectional view of an expandable member 405 according to an embodiment of the invention having pleats 440 that are folded in an accordion-like fashion about an axis normal to the longitudinal axis La of the stylet 404. In some embodiments, an expandable member can include pleats that are folded in multiple directions about multiple axes. For example, in some embodiments, an expandable member can include some pleats that are folded in an accordion-like fashion, similar to that shown in FIG. 45, and some pleats that are also wrapped about the longitudinal axis of the stylet, similar to that shown in FIG. 43.

Returning to FIGS. 39-44, the expandable members shown and described herein can be constructed from any material having suitable properties for being inserted percutaneously into a bone structure, compacting bone material and/or displacing bone material. Such material properties can include, for example, biocompatibility, resistance to corrosion and/or degradation, high tensile strength, high tear resistance, high puncture resistance, high lubricity, suitable hardness, compliance (e.g., the expandable member's ability to expand appreciably beyond its nominal size) and/or elasticity. Moreover, the material properties suitable for operation within a bone structure can be different than the material properties that may be suitable for expandable members operating in other regions of a patient's body. Said another way, an expandable member suitable for use in the cardiovascular system may not be suitable for use in bone structures because of the nature of such bone structures, which can include multiple regions of bone having different densities, sharp protrusions, narrow access channels and the like, and because of the intended operation of the expandable member within the bone structure, which can include compacting bone and/or displacing bone.

In some embodiments, for example, an expandable member can be a high-compliant balloon configured to significantly elastically deform when expanded. In other embodiments, an expandable member can be a low-compliant balloon configured to compact and/or displace bone material without significantly deforming. The compliance of a balloon is the degree to which a size of the balloon in an unfolded state changes as a function of the pressure within the balloon. For example, in some embodiments, the compliance of a balloon can be used to characterize the change in the diameter of the unfolded balloon as a function of the balloon pressure. In some embodiments, the diameter of an unfolded balloon characterized as a low-compliant balloon can change by zero to ten percent over the range of inflation pressure. In other embodiments, an unfolded balloon in which the diameter changes by as much as 20 percent may be characterized as a low-compliant balloon. Similarly, in some embodiments, the diameter of an unfolded balloon characterized as a high-compliant balloon can change by 18 to 30 percent. In other embodiments, the diameter of an unfolded high-compliant balloon can change by as much as 100 to 600 percent over the range of inflation.

In some embodiments, the compliance of a balloon can be used to characterize the change in the length of the balloon as a function of the balloon pressure. The change in length can also be referred to as the elongation percentage of the balloon. In other embodiments, the compliance of a balloon can be used to characterized the change in volume of the balloon as a function of the balloon pressure. Similarly, in some embodiments, the compliance of a balloon can be used to characterize the material properties from which the balloon or portions of the balloon are constructed.

In some embodiments, for example, an expandable member can be constructed from a low-compliant material (e.g., a material having a low modulus of elasticity), such as polyamide, polyethylene terephthalate (PET), Nylons, cross-linked Polyethylene, PEBAX®, Polyurethanes, PVC or any blend of these compounds. In some embodiments, an expandable member can be constructed from Nylon 12.

Because the overall characteristics of the expandable member, including the compliance, can be a function of both the material from which the expandable member is constructed and the structural characteristics of the expandable member, the material from which the expandable member 305 is constructed can be selected in conjunction with the desired structural characteristics of the expandable member. As discussed above, the overall characteristics of an expandable member to be deployed within a bone structure can be different than the characteristics that may be suitable for expandable members operating in other regions of a patient's body. For example, an expandable member used to displace a bone structure may be configured to exert a much higher lifting force when expanded than an expandable member used to deploy a stent. Similarly, an expandable member used to repair a fracture that occurred, for example, three months before treatment may be configured to exert a higher lifting force than an expandable member used to repair a new fracture. Similarly, an expandable member used to repair a fracture that occurred, for example, six months or more before treatment may be configured to exert a higher lifting force than an expandable member used to repair a new fracture.

In some embodiments, the performance characteristics of the expandable member 305, such as the burst pressure, the lifting force when the expandable member 305 is being expanded (e.g., the dynamic load capability) and/or the static load capability when expanded, can be a function of the tensile strength, the compliance of the material, the thickness of the material and/or the inclusion of any stress concentration risers (i.e., discontinuous surfaces and the like). Accordingly, in some embodiments, an expandable member can be constructed of a material having a very high tensile strength to offset the effects of stress concentration risers. In other embodiments, as discussed in more detail herein, an expandable member can include areas of reinforcement, such as for example, a coating, an abrasion-resistant filler, such as carbon or PEBAX®, within the primary layer and/or outer layer to produce the desired characteristics.

In some embodiments, for example, an expandable member can have a rated burst pressure of between 1.4 MPa and 2.8 MPa (200 psi and 400 psi). The rated burst pressure is the pressure to which a statistical sampling of expandable members can be inflated without failure. For example, the rated burst pressure can be associated with a 99 percent compliance with a statistical confidence of 95 percent. Said another way, the rated burst pressure is not the maximum pressure to which the expandable member can be inflated, but is a pressure level below which the expandable member will not likely fail. In other embodiments, the expandable member can have a rated burst pressure of as much as 5.5 MPa (800 psi). In yet other embodiments, the expandable member can have a rated burst pressure of approximately 2.4 MPa (350 psi). Similarly, in some embodiments, the expandable member 305 can be configured to have a static load capability, which can be an indication of the force that can be exerted when displacing bone, of between 0.25 MPa and 4 MPa (36 psi and 580 psi). In yet other embodiments the expandable member 305 can be configured to have a static load capability of approximately 3 MPa (435 psi).

Figure 46:
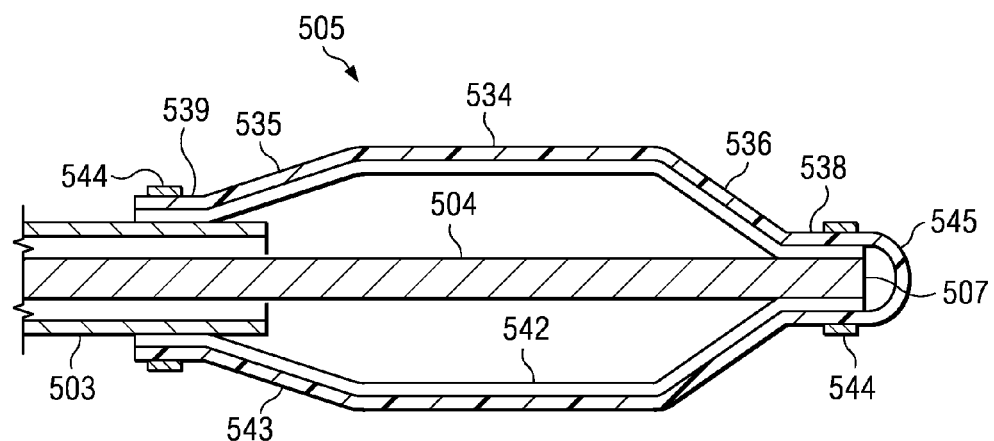
FIG. 46 is a cross-sectional view of an expandable member according to an embodiment of the invention in an expanded configuration.

Although the expandable member 305 is shown and described as being constructed from a single material, in some embodiments, an expandable member can be constructed from more than one material. In this manner, the expandable member can use the advantageous properties of multiple materials. For example, FIG. 46 is a cross-sectional view of an expandable member 505 according to an embodiment of the invention that is constructed of two different materials. As described above, the expandable member 505 includes a distal tapered portion 536, a proximal tapered portion 535 and a central portion 534 disposed between the distal tapered portion 536 and the proximal tapered portion 535. The proximal tapered portion 535 terminates in a proximal bond portion 539 that is coupled to the outer shaft 503. Similarly, the distal tapered portion 536 terminates in a distal bond portion 538 that is coupled to the distal end portion 507 of the stylet 504.

The expandable member 505 has an inner layer 542 disposed within an outer layer or sheath 543. The inner layer 542 is constructed from a first material and the outer sheath 543 is constructed from a second material, different than the first material. In some embodiments, the inner layer 542 can be constructed from a high strength, low-compliant material, such as, for example Nylon 12. Such low-compliant materials, however, can have a crystalline or semi-crystalline molecular structure, which can result in decreased abrasion resistance, decreased tear resistance and/or decreased puncture resistance. Moreover, to minimize the profile of the expandable member 505, the wall of the inner layer 542 can be relatively thin, which can further decrease the abrasion resistance, tear resistance and/or puncture resistance. Accordingly, the outer sheath 543 can be constructed from a polymer having a more amorphous molecular structure, thereby providing increased abrasion resistance, tear resistance and/or puncture resistance.

The ability of the outer sheath 543 to resist surface abrasion, tearing, and puncture when deployed within a bone structure can be characterized in various ways. For example, a Taber Abrasion Resistance Value of less than about 90 mg loss can indicate a sufficient level of resistance to puncture when the outer sheath 543 is in contact with bone. Similarly, a Rotating Drum Abrasion Resistance Value of less than 70 mm$^3$ can also indicate a sufficient resistance to puncture when contacting bone. The tear resistance of the outer sheath 543 can be characterized by the Elmendorf tear strength, which is a measure of the force required to propagate an existing slit a fixed distance to the edge of the test sample. In some embodiments, an Elmendorf tear strength of greater than about 280 lbf/in can indicate a sufficient resistance to tearing caused by bone abrasion. In other embodiments, the abrasion resistance, tear resistance and/or puncture resistance can be characterized by the Shore Hardness value of the outer sheath 543.

In yet other embodiments, the puncture and/or abrasion resistance of the expandable member 505 and/or the outer sheath 543 can be measured by determining the force required to puncture the expandable member 505 and/or outer sheath 543. In certain instances, for example, such a test can include placing a sample of the expandable member 505 and/or outer sheath 543 on a test bed while retaining the edges thereof. A test tool constructed from a predetermined material (e.g., stainless steel) and having a predetermined geometry (i.e., the tip geometry) is then lowered at a constant speed until the tip contacts the test specimen. The force required to puncture the expandable member 505 and/or outer sheath 543 is then determined by a load cell coupled to the test tool. The force can be used, for example, as a means to compare various materials, sizes and/or coatings from which expandable members are constructed. In some embodiments, an expandable member 505 and/or outer sheath 543 can have a puncture force according to the above-described test of 12 lbf.

Because polymers having a lesser degree of crystallinity can have a different level of compliance than the low-compliant materials from which the inner layer 542 can be constructed, the size of the outer sheath 543 can be selected in conjunction with the expansion ratio (i.e., a radial and a longitudinal elongation percentage) of the material from which the outer sheath 543 is constructed. In this manner, the outer sheath 543 can be selected to ensure that when the expandable member 505 is in the expanded configuration, the outer sheath 543 does not burst, limit the expansion of the inner layer 542 or the like. For example, in some embodiments, the inner layer 542 can be constructed from a low-compliant material such that a size of the inner layer 542 (e.g. the diameter when unfolded) changes by between zero and twenty percent and the outer sheath 543 can be constructed from a more compliant material such that a size of the outer sheath 543 (e.g. the diameter when unfolded) changes by approximately fifty percent. In other embodiments, the inner layer 542 can be constructed from a low-compliant material such that an unfolded size of the inner layer 542 changes by approximately ten to twenty percent and the outer sheath 543 can be constructed from a high-compliant material such that an unfolded size of the outer sheath 543 changes by approximately between 400 and 600 percent. In yet other embodiments, the inner layer 542 can be fabricated of a high-compliant material such that an unfolded size of the inner layer 542 changes by approximately 200 to 400 percent and the outer sheath 543 can be fabricated of a high-compliant material such that an unfolded size of the outer sheath 543 changes by approximately between 400 and 600 percent.

In some embodiments, the outer sheath 543 can be constructed from a material having a high lubricity, which can be beneficial during insertion and/or removal of the expandable member. During expansion, the lubricity of the outer sheath 543 can also prevent the folds and/or pleats of material from adhering together, thereby ensuring proper expansion. Similarly, the lubricity of the outer sheath 543 can also improve the tear resistance of the expandable member 505 by allowing the surface of the expandable member 505 to slide smoothly relative to protrusions that can exist within the bone structure. The use of a lubricious outer sheath 543 can also eliminate the need for a lubricious coating, which can be difficult to apply and can, at times, become ineffective. In some embodiments, the outer sheath can be constructed from a fluoropolymer, such as for example, polytetrafluoroethylene (i.e., Teflon). Similarly, the outer sheath 543 can be constructed using any suitable manufacturing process, such as, for example, an extrusion process.

As shown in FIG. 46, the outer sheath 543 includes a tapered distal end 545 covering both the distal bond portion 538 of the inner layer 542 and the distal end portion 507 of the stylet 504. This arrangement can allow for easier insertion.

The outer sheath 543 is coupled to the inner layer 542 by a pair of clamps 544 disposed on the distal bond portion 538 and the proximal bond portion 539 of the expandable member 505. The clamps 544 can be, for example, elastic bands, inelastic tie-wrap type clamps, spring clamps, swaged clamps or the like. The clamps 544 can be constructed from any suitable material, such as for example, stainless steel or nitinol. Moreover, in some embodiments, the clamps 544 can include a radio-opaque material, such as titanium or platinum.

In some embodiments, the clamps 544 also couple the expandable member 505 to the stylet 504 and the outer shaft 503 of the catheter. In such an embodiment, the clamps 544 are configured to provide sufficient clamping force to maintain a fluid-tight seal at the distal bond portion 538 and the proximal bond portion 539. In other embodiments, as discussed in more detail herein, the expandable member 505 is coupled to the stylet 504 and the outer shaft 503 independently from the clamps 544.

In some embodiments, the outer sheath 543 can be coupled to the inner layer 542 before any pleats, folds or the like are formed in the inner layer 542. In this manner, the pleats and/or folds are formed in the inner layer 542 and the outer sheath 543 simultaneously. In other embodiments, the outer sheath 543 can be coupled to the inner layer 542 after inner layer 542 has been pleated. In this manner, any folds and/or pleats formed the outer sheath 543 can be configured differently from those formed in the inner layer 542. In yet other embodiments, the outer sheath 543 can be devoid of any folds and/or pleats, relying instead upon other properties, such as for example high elasticity, to maintain a low profile when in the collapsed configuration.

Although the outer surface of the inner layer 542 is shown in FIG. 46 as being in continuous contact with the inner surface of the outer sheath 543 when the expandable member 505 is in the expanded configuration, in some embodiments, the outer surface of the inner layer 542 and the inner surface of the outer sheath 543 may not be in continuous contact when the expandable member 505 is in the collapsed and/or expanded configuration. For example, in some embodiments, because clamps 544 are used to couple the outer sheath 543 to the inner layer 542, the inner layer 542 may not be in continuous contact with the inner surface of the outer sheath 543. In this manner, for example, the inner layer 542 can move relative to the outer sheath 543 when the inner layer 542 and the outer sheath 543 are collectively moved between the collapsed configuration and the expanded configuration.

Figure 47:
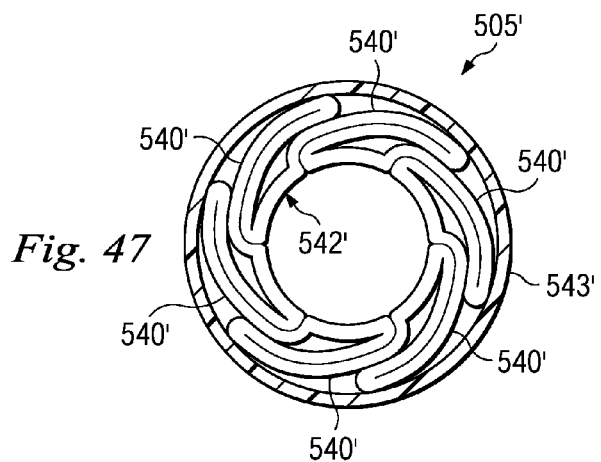
FIG. 47 is a cross-sectional view of an expandable member according to an embodiment of the invention in a collapsed configuration.

For example, FIG. 47 shows an example of an expandable member 505' according to an embodiment of the invention in a collapsed configuration. As described above, the expandable member 505' includes an inner layer 542' and an outer sheath 543' disposed about the inner layer 542'. The inner layer 542' has multiple pleats 540'. As shown in FIG. 47, the pleats 540' are folded circumferentially to minimize the profile (e.g., the outer diameter) of the expandable member 505' when in its collapsed configuration. As shown in FIG. 47, the outer sheath 543' is disposed about the inner layer 542' such that the outer sheath 543' is not in continuous contact with an inner layer 542'.

Although the outer sheath 543 and the inner layer 542 are shown and described as being coupled by a pair of clamps 544, in some embodiments, the outer sheath 543 can be coupled to the inner layer 542 by any suitable means. For example, in some embodiments, the outer sheath 543 can be coupled to the inner layer 542 via an adhesive, a thermal bond, an ultraviolet radiation (UV) bond or the like. In other embodiments, the outer sheath 543 is constructed from a material having a sufficient elasticity and size to remain coupled to the inner layer 542 without the need for an adhesive, clamp or the like.

Figure 48:
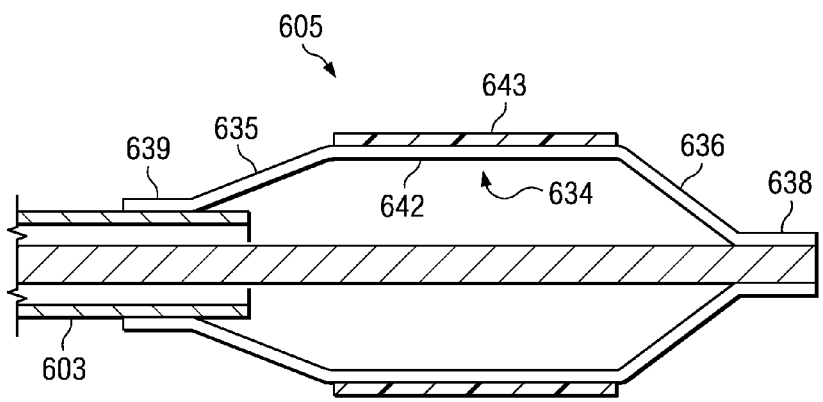
FIG. 48 is a cross-sectional view of an expandable member according to an embodiment of the invention in an expanded configuration, the expandable member including an outer sheath covering a portion of an inner layer.

Although the outer sheath 543 is shown and described as covering substantially the entire inner layer 542, in some embodiments, the outer sheath 543 can cover only a portion of the inner layer 542. FIG. 48 shows an example of an expandable member 605 that includes an outer sheath 643 that covers only a portion of an inner layer 642. Similar to the expandable members described above, the expandable member 605 includes a distal tapered portion 636, a proximal tapered portion 635 and a central portion 634 disposed between the distal tapered portion 636 and the proximal tapered portion 635. The proximal tapered portion 635 terminates in a proximal bond portion 639 and the distal tapered portion 636 terminates in a distal bond portion 638.

The expandable member 605 has an inner layer 642 constructed from a first material and an outer sheath 643 constructed from a second material, different than the first material. The outer sheath 643 is coupled to and disposed about the central portion 634 of the inner layer 642. In this manner, central portion 634, which can, in some embodiments, be thinner than the distal tapered portion 636 and the proximal tapered portion 635, can be selectively reinforced. Moreover, in some embodiments, when the expandable member 605 is in its expanded configuration, the central portion 634 can be the portion of the expandable member 605 configured to contact and/or displace bone that can be abrasive, sharp and/or cause punctures. Accordingly, constructing the expandable member such that the outer sheath 643 is disposed about a central portion of the expandable member, the expandable member 605 can be configured to resist such damage.

Although the outer sheath 643 is shown and described as covering the central portion 634 of the inner layer 642, in other embodiments, the outer sheath 643 can be configured to cover a different portion of the inner layer 642. For example, in some embodiments, an expandable member can be deployed in a bone structure such that the distal tapered portion is the portion of the expandable member that is configured to contact and/or displace bone. In such an embodiment, the distal tapered portion can be selectively reinforced. Moreover, the outer sheath 643 need not be disposed symmetrically about the inner layer 642.

Although the expandable members shown and described above include two layers, in some embodiments, an expandable member can include any suitable number of layers. For example, in some embodiments, an expandable member can include an inner layer, an intermediate layer disposed substantially about the entire inner layer and an outer layer disposed selectively about less than the entirety of the intermediate layer.

In some embodiments, an expandable member can include a coating applied to the exterior surface of the expandable member to improve the lubricity, abrasion resistance, tear resistance and/or puncture resistance of the expandable member. Additionally, a coating can be applied to enhance the optical properties, such as, for example, the radio-opacity, of the expandable member. In some embodiments, for example, the coating can be selectively disposed on less than the entirety of the exterior surface. For example, in some embodiments, an abrasion resistant coating can be applied to those portions of the exterior surface configured to contact bone.

The coating can include any material suitable for being applied to a polymeric substrate and having suitable properties, such as, for example, biocompatibility, abrasion resistance, hardness, tear resistance, puncture resistance, lubricity and the like. In some embodiments, for example, the coating can be an aliphatic elastomer, such as polyurethane, silicone, polyether block amide (PEBAX®), polyvinyl chloride (PVC) or the like. In other embodiments, the coating can be a hydrogel configured to improve the lubricity of the expandable member. In yet other embodiments, the coating can include an inorganic filler to provide increased durability. For example, in some embodiments, the coating can include a ceramic material, such as titanium carbide, disposed within a polymeric matrix.

Although described as including a single coating, in some embodiments, an expandable member can include multiple coatings. For example, in some embodiments an expandable member can include an abrasion resistant coating disposed on substantially the entire exterior surface and a lubricious coating disposed on the proximal portion of the exterior surface. The location of such a lubricious coating can be selected, for example, to improve the ease with which the expandable member can be inserted and/or removed from a cannula and/or a bone structure within a body. In other embodiments, an expandable member can include an abrasion resistant coating disposed on substantially the entire exterior surface and a therapeutic coating disposed on a portion of the exterior surfaces. Such therapeutic coatings can include, for example, a coating configured to sterilize the bone structure In yet other embodiments, an expandable member can include one or more layers of an abrasion resistant coating and one or more layers of a hydrophilic coating.

Figure 49:
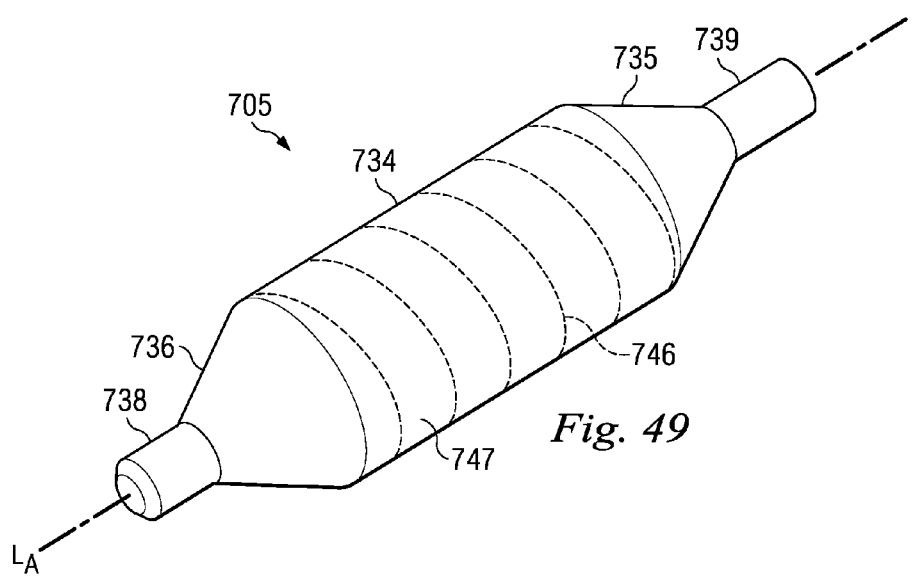
FIG. 49 is a perspective view of an expandable member according to an embodiment of the invention in an expanded configuration.

In alternative embodiments, an expandable member can include a reinforcement member to reinforce portions of the expandable member. For example, FIG. 49 is a perspective view of an expandable member 705 according to an embodiment of the invention that includes a reinforcement member 746. As described above, the expandable member 705 includes a distal tapered portion 736, a proximal tapered portion 735 and a central portion 734 disposed between the distal tapered portion 736 and the proximal tapered portion 735. The proximal tapered portion 735 terminates in a proximal bond portion 739 and the distal tapered portion 736 terminates in a distal bond portion 738. The reinforcement member 746 is disposed along an outer surface 747 of the central portion 734 expandable member 705. As illustrated, the reinforcement member 746 can be arranged spirally about the longitudinal axis La of the expandable member 705. In some embodiments, the reinforcement member 746 can be a single member that is wound around the central portion 734 of the expandable member 705 a predetermined number of turns. In other embodiments, the expandable member 705 can include multiple reinforcement members 746 arranged substantially parallel to each other and disposed radially about the circumference of the central portion 734 of the expandable member 705. The reinforcement member 746 can be constructed of any material having suitable properties, such as flexibility, elasticity, tensile strength and/or biocompatibility. Examples of materials from which the reinforcement member 746 can be constructed include Vectran, Kevlar, Nylon and the like.

The reinforcement member 746 can reinforce portions of the wall 742 of the expandable member 705, without significantly increasing the profile of the expandable member 705. For example, in some embodiments, the inclusion of a reinforcement member 746 can increase the rated burst pressure of the expandable member 705. In other embodiments, for example, in those embodiments in which the expandable member 705 has a high-compliant wall, the reinforcement member 746 can also prevent overexpansion of the wall 742 during use.

The reinforcement member 746 can have any suitable size and/or cross-sectional shape. In some embodiments, for example, the reinforcement member 746 can be a fiber having a substantially circular cross-sectional having a diameter of 0.25 mm (0.001 in.) or less. In other embodiments, the reinforcement member 746 can have a substantially rectangular cross-section. Similarly, the "wrap density" of the reinforcement member 746 (i.e., the number of reinforcement members per unit length) can be any suitable amount. For example, in some embodiments, the reinforcement member 746 can be disposed about the wall at a wrap density of between 1 and 4 wraps per millimeter. In other embodiments, the reinforcement member can be disposed about the wall at a wrap density of less than 1 wrap per millimeter or greater than 4 wraps per millimeter. In yet other embodiments, the wrap density of the reinforcement member 746 can vary along the longitudinal axis La of the expandable member. In this manner, the reinforcement member 746 can be concentrated in areas of the expandable member 705 where greater reinforcement is desired.

FIG. 50 is a perspective view of an expandable member 805 according to an embodiment of the invention that includes a series of reinforcement members 846 disposed longitudinally along the expandable member 805. The expandable member 805 includes a distal tapered portion 836, a proximal tapered portion 835 and a central portion 834 disposed between the distal tapered portion 836 and the proximal tapered portion 835. The proximal tapered portion 835 terminates in a proximal bond portion 839 and the distal tapered portion 836 terminates in a distal bond portion 838. The reinforcement members 846 are disposed longitudinally along an outer surface 847 of the expandable member 805.

Although the expandable members 705 and 805 are shown and described as including a reinforcement member or series of reinforcement members disposed either spirally or longitudinally, in other embodiments, an expandable member can include a first series of reinforcement members disposed radially about the circumference of the expandable member and a second series of reinforcement members disposed longitudinally along the surface of the expandable member. In other embodiments, a reinforcement member can be a closely knitted series of fibers (which can be referred to as a "sock") extending spirally, longitudinally and/or about the circumference of the expandable member.

Although the expandable members 705 and 805 are shown and described as including a reinforcement member or series of reinforcement members disposed along the outer surface of the expandable member, in some embodiments, an expandable member can include a reinforcement member disposed within the side wall of the expandable member. In other embodiments, an expandable member can include an inner layer, an outer sheath disposed about the inner layer and a reinforcing reinforcement member disposed between the inner layer and the outer sheath. In yet other embodiments, an expandable member can include a reinforcing reinforcement member disposed on the interior surface of the expandable member.

FIG. 51 is a flow chart illustrating a method 900 for manufacturing a catheter assembly having an expandable member according to an embodiment of the invention. The illustrated method includes manufacturing the expandable member, at 910. The expandable members shown and described above can be manufactured by a variety of processes, including, for example, an extrusion process and/or a blow molding process. Examples of such processes are described in U.S. Pat. No. 6,979,341, which is incorporated herein by reference in its entirety. In some embodiments, an expandable member is formed by first extruding a tube and then shaping the tube using a blow molding process to define the final shape of the expandable member. During the extrusion process, a variety of process parameters can have an effect on the mechanical properties of expandable member. Such process parameters can include, for example, the temperature profile from the feeding zone of the screw to the tooling, the tooling geometry of the cross head, the screw and/or the barrel, the rate at which the tubing is extruded (e.g., the rotation speed of the extrusion gear), the temperature of the cooling bath and/or the distance between the tooling and the cooling bath. In some embodiments, for example, the rate at which the extruded tubing is cooled (i.e., the quench rate) can impact the molecular structure of the tubing. For example, in some embodiments, a faster rate of cooling can result in a tubing having a more amorphous molecular structure. As discussed above, the level of crystallinity of the molecular structure can impact the compliance of the expandable member.

Similarly, during the blow molding process, a variety of parameters also can influence the properties of the expandable member. Such parameters can include, for example, the temperature of the heating jaws, the pre-pressure/warm-up time, the forming pressure, the rate of cooling, the annealing time, the stretch rate and/or the stretch distance. In some embodiments, for example, the forming pressure can impact the burst pressure of the expandable member. For example, in some embodiments, increasing the forming pressure from 1.4 MPa to 2.1 MPa (200 psi to 300 psi) can increase the rated burst pressure by approximately 207 KPa (30 psi).

Upon completion of the extrusion and/or blow molding processes, the method includes coupling the expandable member to the catheter assembly, at 920. In particular, referring to FIGS. 39 and 40, the distal bond portion 338 is coupled to the distal end portion 307 of the stylet 304 to form a fluid-tight seal. Similarly, the proximal bond portion 339 is coupled to the outer shaft 303 to form a fluid-tight seal. Moreover, the seal between the expandable member 305 and the catheter assembly 302 is configured to withstand the high operating pressures and/or torsional stress that can be required when using the expandable member 305 to displace and/or compact bone. For example, in some embodiments, the seal between the expandable member and the catheter assembly is configured to withstand inflation pressures of between 1.4 MPa and 2.8 MPa (200 psi and 400 psi). Similarly, in some embodiments, coupling between the expandable member and the catheter assembly is configured maintain a fluid-tight seal when at least a portion of the expandable member is twisted about catheter assembly through at least four revolutions.

The expandable member can be coupled to the catheter assembly using any suitable technique, such as, for example via an adhesive, a chemical bond, a UV bond, a laser bond, a shrink fit, a mechanical clamp or the like. In some embodiments, for example, the expandable member can be coupled to the catheter assembly using clamps similar to the clamps 544 shown and described above (see FIG. 30). In other embodiments, the expandable member can be coupled to the catheter assembly using a combination of techniques. For example, in some embodiments, the distal bond portion can be coupled to the stylet via a UV bond and the proximal bond portion can be coupled to the outer shaft via an adhesive.

In some embodiments, the expandable member can be bonded to the catheter assembly using a radio frequency induction heating process (i.e., an RF bonding process). The RF bonding process is particularly well suited for those embodiments that include a metallic outer shaft and/or stylet. For example, in some embodiments, the distal bond portion of the expandable member can be bonded to the distal end portion of a stainless steel stylet. First, the distal bond portion of the expandable member is placed in contact with the stylet. An induction coil is placed around a portion of the stylet and is energized with alternating current at a predetermined power and frequency. The alternating current produces magnetic field around the stylet, which generates an electrical current within the stylet. The electrical current produce areas of localized heat, which liquefy the adjacent portions of the expandable member. The liquid portions then move into the crevices on the surface of the stylet. When the current is removed, the liquid portions of the expandable member solidify to form a bond. In some embodiments, the surface of the stylet can be configured to improve the bond between the expandable member and the stylet. For example, in some embodiments, the surface of the stylet can be bead blasted to improve the bond between the expandable member and the stylet.

In some embodiments, as described above, a catheter assembly can include a polymeric inner shaft disposed between the stylet and the distal bond portion of the expandable member. The addition of the inner shaft can provide additional material to form the distal bond, thereby increasing the strength of the distal bond.

Because RF bonding produces areas of localized heating, a bond can be produced in the distal bond portion and/or the proximal bond portion of the expandable member without subjecting other portions of the expandable member to heat. In this manner, the expandable member can be coupled to the catheter assembly without further annealing the expandable member.

In some embodiments, the operation 920 of coupling the expandable member to the catheter assembly can include multiple different processes, as shown in FIG. 52. First a portion of the stylet is bonded within the inner shaft, 922, as shown and described above with reference to FIGS. 40 and 41. In some embodiments, for example, the stylet can be disposed within a lumen defined by the inner shaft and bonded over a portion of the longitudinal length of the stylet. In other embodiments, the stylet can be bonded within the inner shaft along the entire length of the inner shaft to form a composite member. As described above, in some embodiments, the stylet and the inner shaft can be coupled using an RF bonding process.

The proximal end portion of the expandable member is then coupled to the distal end portion of the outer shaft, 923. As shown and described above, with reference to FIGS. 40 and 41, the axial length of the proximal bond can be, for example, between 1 mm and 7 mm (0.040 in. and 0.275 in.). Any suitable method of coupling can be used (e.g., adhesive, a chemical bond, a UV bond, a laser bond, a shrink fit, a mechanical clamp or the like).

The stylet and inner shaft assembly is then disposed within the lumen of the outer shaft, 924. A sleeve, of the type shown and described above with reference to FIG. 42 is then disposed about the distal end portion of the inner shaft, 925. As described above, the sleeve can improve the characteristics of the distal bond. In some embodiments, the sleeve can include a colorant to be excited by a laser used to couple the expandable member, the inner shaft and the sleeve, as described below.

The distal end portion of the expandable member is then coupled to the distal end portion of the inner shaft/stylet assembly, 926. In some embodiments, the distal end portion expandable member, the inner shaft and the sleeve can be collectively coupled by using two distinct operations. First, a thermal bonding process (i.e., the application of heat to the areas to be bonded) can be used to form a fluid-tight seal at the distal bond location. Second, a laser bond process, which produces a more localized heating of the materials, can be used to form a distal bond such that the distal bond can withstand the torsional stresses, as discussed herein. In this manner, the axial length of the distal bond can be shortened without sacrificing the strength of the distal bond.

Although not necessary for the successful manufacture of the catheter assembly, the illustrated method includes applying a coating of the type described above, at 930. The coating can be applied by first placing the expandable member in its expanded configuration. The outer surface of the expandable member is then modified to produce a rough surface and/or otherwise prepare the outer surface for receiving the coating. Such modification can be referred to as "priming" or "etching," and can be done using any suitable technique. In some embodiments, for example, the surface of the expandable member is prepared by a plasma-etching process, in which the surface is exposed to a plasma to produce microscopic grooves for receiving the coating. In other embodiments, the expandable member is exposed to a thermoplastic polymer, such as for example parylene (C, D or N) to prepare the outer surface for receiving the coating.

After the outer surface is sufficiently prepared, the coating is applied using a dip coating process. The expandable member is then annealed at a temperature of approximately 60° C. for approximately 2-3 hours to stabilize the coating and/or promote cross-linking between the coating and the outer surface of the expandable member. Said another way, the annealing operation is done to help ensure that the coating will not crack, delaminate or otherwise deteriorate when the expandable member is in use.

Although described as being applied in a single layer, in some embodiments, the coating can be applied in multiple layers. For example, in some embodiments, an expandable member can include a single layer coating having a thickness of approximately 5 μm (0.0002 in.). In other embodiments, an expandable member can include up to six layers of the coating, having a total thickness of between 20 and 40 μm (0.0008 and 0.0016 in.). In yet other embodiments, an expandable member can include multiple layers of different coatings.

Although the illustrated method includes applying a coating to the expandable member, in other embodiments a coating need not be applied. For example, in some embodiments, an outer sheath of the type shown and described above can be coupled to the expandable member.

The illustrated method then includes forming the pleats and/or folds of the type described above, at 940. The pleats can be formed by placing a portion of the expandable member within a die having an aperture that includes the desired form (i.e., the shape and/or size) of the pleats. The die is then moved to compress the expandable member for a predetermined amount of time to form the pleats. In some embodiments, a vacuum is applied to the expandable member when the die is compressed about the expandable member. In other embodiments, the die can be placed about the expandable member when the expandable member is at least partially expanded. In such embodiments, the movement of the die can cause the expandable member to be collapsed. In some embodiments, the die can include a heating element to heat the expandable member during the pleat-forming process. In this manner, the pleats can be "heat set" to induce the pleats to remain after the die is removed.

During the pleat-forming process, a variety of process parameters can have an effect on the mechanical properties of the expandable member. Such process parameters can include, for example, the amount of time during which the expandable member is compressed, the temperature of the expandable member and/or the pressure of compression. For example, in some embodiments, the temperature at which the expandable member is exposed can be a trade-off between improving the "shape memory" of the pleats and thermally degrading the mechanical characteristics of the expandable member. Said another way, exposing the expandable member to a high temperature can result in improved "shape memory" of the pleats, but can also thermally degrade the mechanical characteristics of the expandable member. Accordingly, because the expandable members are exposed to high inflation pressures and the harsh environment that can exist within bone structures, in some embodiments, the pleat-forming process is configured to avoid compromising the overall characteristics of the expandable member. In some embodiments, the pleats are formed at approximately 70° C. under a pressure of no greater than 68 N for a duration of approximately 5 seconds.

The expandable member is then removed from the die and wrapped about the outer shaft and/or stylet to reduce the profile of the expandable member at 950. In some embodiments, the expandable member is wrapped and/or folded using the twisting apparatus as shown and described above. In other embodiments, the expandable member is wrapped and/or folded using a second die (i.e., a "wrapping die") that is configured to secure the pleats and rotate relative to the outer shaft of the catheter assembly. In some embodiments, the expandable member is folded at an elevated temperature and/or pressure. For example, in some embodiments, an expandable member can be folded at approximately 80° C. under a pressure of no greater than 133 N for a duration of approximately 150 seconds. A protective sleeve (not shown in the above figures) is then disposed about the expandable member. In some embodiments, the assembly (e.g., the expandable member and the protective sleeve) is annealed to further improve the "shape memory" of the expandable member.

The protective sleeve can be, for example, an extruded polymeric sleeve constructed of a PEBAX® blend. In some embodiments, for example, the protective sleeve can include a colorant. In this manner, the protective sleeve can serve to identify certain characteristics of the expandable member and/or the catheter assembly. For example, in some embodiments the size of the expandable member can be correlated to the color of the protective sleeve.

The illustrated method then includes disposing an outer sheath of the type shown and described above over the expandable member, at 960. As described above, the outer sheath can be secured to the expandable member by an adhesive, a clamp or the like.

FIG. 53 is a flow chart illustrating a method 970 according to an embodiment of the invention. The illustrated method includes moving an actuator from a first position to a second position such that a first shaft is rotatable relative to a second shaft, 971. The second shaft is disposed within the first shaft and is coupled to an expandable member. The actuator is then moved from the second position to the first position such that the second shaft is rotatable relative to the first shaft through a plurality of discrete increments, 972. In some embodiments, for example, the first shaft and the second shaft can be a portion of a catheter assembly that includes an actuator, as described above.

In some embodiments, the method 970 can optionally include percutaneously inserting into a body at least a distal portion of the first shaft and at least a distal portion of the second shaft before the moving the actuator from the first position to the second position and before the moving the actuator from the second position to the first position. In this manner, for example, the expandable member can be disposed within a bone structure.

In other embodiments, the method can optionally include moving the expandable member from a first collapsed configuration to an expanded configuration after the moving the actuator from the first position to the second position. In this manner, as described above, the expandable member can displace a portion of a bone structure. In yet other embodiments, the method can include moving the expandable member from the expanded configuration to a second collapsed configuration after the moving the expandable member from the first collapsed configuration.

In other embodiments, the method can optionally include removing from the body the distal portion of the first shaft and the distal portion of the second shaft after the moving the actuator from the first position to the second position and after the moving the actuator from the second position to the first position.

FIG. 54 is a flow chart illustrating a method 975 according to an embodiment of the invention. The illustrated method includes engaging a ratchet of a first member with a pawl portion of a second member, 976. The first member is coupled to a first shaft, as described above. The second member is coupled to a second shaft such that the second shaft can rotate relative to the first shaft in a first direction. The second shaft coupled to an expandable member. In this manner, rotation of the second shaft relative to the first shaft can twist at least a portion of the expandable member about the second shaft, as described above. The ratchet of the first member is disengaged from the pawl portion of the second member such that that the second shaft can rotate relative to the first shaft in a second direction opposite the first direction, 977.

FIG. 55 is a flow chart illustrating a method 980 according to an embodiment of the invention. The illustrated method includes inserting into a body a catheter assembly, 981. The catheter assembly, which can be any suitable catheter assembly as shown and described above, includes a shaft and an expandable member coupled to the shaft. In some embodiments, the inserting includes disposing the expandable member within a bone structure. In some embodiments, the catheter assembly is inserted via a cannula.

The expandable member is moved from a first collapsed configuration to an expanded configuration, 982. In some embodiments, at least a portion of a bone structure is displaced relative to another portion of the bone structure when the expandable member is moved from its first collapsed configuration to its expanded configuration.

The expandable member is moved from the expanded configuration to a second collapsed configuration, 983, after the moving the expandable member from the first collapsed configuration. In some embodiments, the second collapsed configuration can be different than the first collapsed configuration. In other embodiments, the second collapsed configuration can be substantially the same as the first collapsed configuration.

The expandable member is then rotated about a centerline of the shaft through a plurality of discrete increments, 984. In this manner, as described above, the profile of the expandable member can be reduced. In some embodiments, the method can optionally include removing the catheter assembly from the body after the expandable member has been rotated, 985.

FIG. 56 is a flow chart illustrating a method 990 according to an embodiment of the invention. The illustrated method includes inserting into a body a distal portion of a catheter assembly, 991. The catheter assembly includes a shaft and an expandable member coupled to the shaft. In some embodiments, the catheter assembly is inserted via a cannula.

The expandable member is then moved from a first collapsed configuration to an expanded configuration, 992. In some embodiments, an end plate of the vertebral body is displaced when the expandable member is moved from its first collapsed configuration to its expanded configuration.

The expandable member then is moved from the expanded configuration to a second collapsed configuration, 993, after the moving the expandable member from the first collapsed configuration. In some embodiments, the second collapsed configuration can be different than the first collapsed configuration. In other embodiments, the second collapsed configuration can be substantially the same as the first collapsed configuration.

A knob coupled to a proximal portion of the catheter assembly is then rotated in a first direction such that the expandable member is twisted about a centerline of the shaft, 994. The knob, which can be any knob of the type shown and described above, is configured to resist rotation in a second direction opposite the first direction. In this manner, the profile of the expandable member can be reduced. The distal portion of the catheter assembly is then from the vertebral body, 995.

Figure 57:
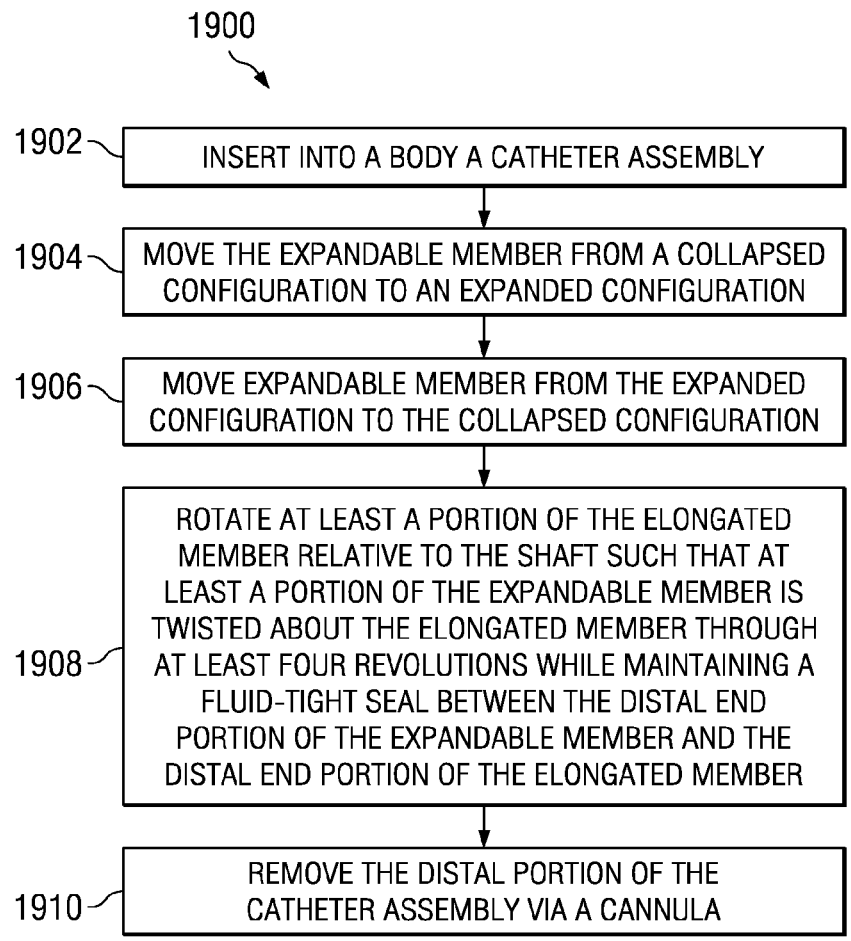
FIG. 57 is a flow chart of a method according to an embodiment of the invention.

FIG. 57 is a flow chart illustrating a method 1900 according to an embodiment of the invention. The illustrated method includes inserting into a body a catheter assembly, 1902. The catheter assembly, which can be any catheter assembly as shown and described above, includes an expandable member, a shaft having a distal end portion coupled to a proximal end portion of the expandable member, and an elongated member rotatably disposed within the shaft. A distal end portion of the elongated member is coupled to a distal end portion of the expandable member. In this manner, when the elongated member is rotated relative to the shaft, at least a portion of the expandable member is twisted about the elongated member. In some embodiments, the inserting includes disposing the expandable member within a bone structure. In some embodiments, the catheter assembly is inserted via a cannula.

The expandable member is moved from a collapsed configuration to an expanded configuration, 1904. In some embodiments, a bone structure is displaced when the expandable member is moved from its first collapsed configuration to its expanded configuration. The expandable member is then moved from the expanded to the collapsed configuration, 1906.

At least a portion of the elongate member is then rotated relative to the shaft such that at least a portion of the expandable member is twisted about the elongated member through at least four revolutions while maintaining a fluid-tight seal between the distal end portion of the expandable member and the distal end portion of the elongated member, 1908. In this manner, as described above, the profile (e.g., the diameter) of the expandable member when in the collapsed configuration can be reduced such that it less than a diameter of a cannula. In some embodiments, the method optionally includes removing the expandable member from the body via the cannula, 1910.

Figure 58:
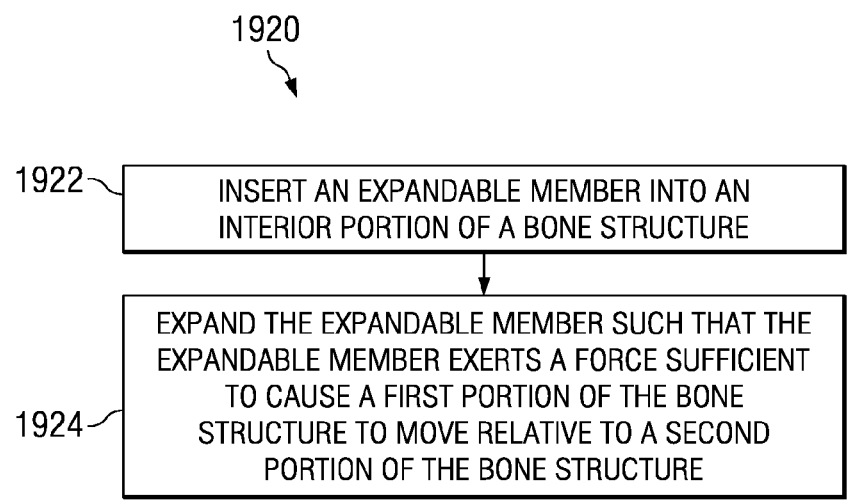
FIG. 58 is a flow chart of a method according to an embodiment of the invention.

FIG. 58 is a flow chart illustrating a method 1920 according to an embodiment of the invention. The illustrated method includes inserting an expandable member into an interior portion of a bone structure, 1922. As described above with reference to FIG. 47, the expandable member includes a first layer and a second layer. The second layer is disposed about the first layer such that an outer surface of the first layer is in discontinuous contact with an inner surface of the second layer. The first layer constructed from a first polymer having a molecular structure. The second layer constructed from a second polymer having a molecular structure more amorphous than the molecular structure of the first polymer.

In some embodiments, the expandable member is inserted via a cannula. In some embodiments, the bone structure can be a vertebral body. In some embodiments, the bone structure can include recalcitrant bone, such as the type of recalcitrant bone found in bone defects that are more than three months old.

The expandable member is then expanded while disposed within the interior portion of the bone structure such that the expandable member exerts a force sufficient to cause a first portion of the bone structure to move relative to a second portion of the bone structure, 1924. In some embodiments, the expanding includes inflating the expandable member to a pressure of at least 1.4 Megapascals. In other embodiments, the expanding includes inflating the expandable member to a pressure of at least 2.8 Megapascals. In yet other embodiments, the expanding includes inflating the expandable member to a pressure of at least 5.5 Megapascals.

In some embodiments, the first layer of the expandable member is moved relative to the second layer of the expandable member when the expandable member is expanded.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Thus, the breadth and scope of the invention should not be limited by any of the above-described embodiments. While the invention has been particularly shown and described with reference to specific embodiments thereof, it will be understood that various changes in form and details may be made. Finally, all publications and patent applications cited in this specification are herein incorporated by reference in their entirety as if each individual publication or patent application were specifically and individually put forth herein.

For example, although the twisting apparatuses described herein are shown and described as being used to rotate an expandable member relative to a catheter, in other embodiments, a twisting apparatus can be used to control the twisting of other medical devices. For example, in some embodiments, a twisting apparatus according to an embodiment of the invention can be used to rotate a portion of a spinal implant and/or implant insertion tool. In other embodiments, a twisting apparatus according to an embodiment of the invention can be used to rotate a portion of a bone screw and/or bone screw insertion device.

Although the twisting apparatuses described herein include a second member configured to rotate relative to a first member thereby controlling the rotation of an elongated member, in other embodiments, a twisting apparatus can include a second member configured to move linearly relative to a first member to control the rotation of an elongated member. For example, in some embodiments, a second member can include a trigger style actuator configured to rotate the elongated member in discrete amounts.

Although the twisting apparatuses described herein include a second member configured to rotate about a longitudinal axis of a stylet, in other embodiments, the second member can be configured to rotate about an axis that is offset from the longitudinal axis of the stylet. In yet other embodiments, the second member can be configured to rotate about an axis that is angularly offset from the longitudinal axis of the stylet.

Although the twisting apparatuses described herein include a second member engaged with an elongated member such that rotation of the second member causes equal rotation of the elongated member, in other embodiments, the elongated member can be configured to rotate with the second member at a ratio other than 1:1. For example, in some embodiments, a twisting apparatus includes a gear reducer disposed between the second member and the elongated member. In this manner, rotation of the second member over a set angular distance can result in rotation of the elongated member over a different angular distance. In other embodiments, a gear reducer can be configured to change the direction of rotation of the elongated member with respect to the second member.

For example, although the method 900 includes coupling an outer sheath to the expandable member after the pleat-forming process is completed, in other embodiments, the outer sheath can be coupled to the expandable member before the pleats are formed in the expandable member. In this manner, the expandable member and the outer sheath can include complimentary pleats. In yet other embodiments, an outer sheath is not coupled to the expandable member. Similarly, in some embodiments, a coating need not be applied to the expandable member.

Although the expandable members shown and described include an outer sheath or a coating, in some embodiments, an expandable member can include an outer sheath and a coating disposed on the outer sheath. For example, in some embodiments, an expandable member can include an outer sheath configured increase the tear resistance of the expandable member and a coating configured to sterilize a portion of the body.

Although the catheter assemblies are shown and described as including an outer shaft and a stylet, in some embodiments a catheter assembly can include an outer shaft, an inner shaft disposed within the outer shaft and a stylet disposed within the inner shaft. In such an arrangement, the inner shaft can extend along with the stylet to the distal bond portion of the expandable member.

Although various embodiments have been described as having particular features and/or combinations of components, other embodiments are possible having a combination of any features and/or components from any of embodiments as discussed above. For example, one such embodiment includes a catheter assembly, an expandable member and a twisting apparatus, as described further below.

The catheter assembly includes an outer shaft, an inner shaft, a stylet and a Y-connector. The outer shaft is extruded using a blend of Nylon 12, nano-composite fillers and colorant. The wall of the outer shaft defines an inflation lumen and provides rigidity and sufficient column strength to withstand internal pressure from inflation, to prevent buckling during insertion and/or to provide torque resistance during use of the twisting device, as described above. The inner shaft is extruded using Nylon 12 and defines a lumen for receiving the stylet. A portion of the inner shaft includes a bonding surface for bonding the inner shaft to the stylet, as described above. The stylet is disposed within the inner shaft and transmits torque from the twisting apparatus to the distal end portion of the expandable member. The stylet is constructed from stainless steel and includes a "U" shaped proximal end portion to be received within the twisting apparatus, as described above. The distal end portion of the stylet is bead-blasted to provide an outer surface to be bonded to the inner shaft.

The Y-connector is molded with a blend of polycarbonate and includes a colorant. The Y-connector is an interface for the outer shaft, inner shaft/stylet sub-assembly, the twisting apparatus and the source of inflation fluid. The Y-connector includes a "one-way" fluid valve to control the flow of the inflation fluid to the inflation lumen described above.

The expandable member is constructed from a polyamide (PA), using a hot mold balloon blowing technology, as described above. The external surface of the expandable member includes an aliphatic polyester (poly) urethane coating to improve the abrasion and durability of the expandable member. During manufacture, the expandable member is coated by first priming the outer surface thereof with an acrylic copolymer and then applying the coating on the outer surface. The coating is then cross linked and cured by one or more annealing operations, as described above. In some embodiments, the coating can include an inorganic filler for increased durability.

As described above, the expandable member is a low-compliant expandable member having a geometry. More particularly, the expandable member is approximately ten percent compliant and has a burst pressure of approximately 350 psi. Moreover, the expandable member is resistant to chemical corrosion and/or degradation, exerts a higher dynamic force and has an puncture and/or abrasion resistance of approximately 12 lbf using the test shown and described above.

An protective insertion sleeve is disposed about the expandable member to protect the expandable member and/or retain the desired shape of the expandable member prior to use. The protective insertion sleeve can be constructed from PEBAX® and a colorant.

The twisting apparatus is configured to twist the expandable member by applying a rotational force to the distal end portion of the expandable member, as described above. The twisting apparatus also includes a ratchet mechanism to prevent the loss of torsional force during the twisting operation. The components included in the twisting apparatus are constructed from Nylon and ABS and are assembled using a cyanoacrylate adhesive. As described above, the twisting apparatus is coupled to the luer cap portion of the catheter assembly. The luer cap is constructed from polycarbonate and includes a coupling portion for coupling the inner shaft/stylet assembly to the outer shaft.

What is claimed is:
1. An apparatus, comprising:
an expandable member configured to displace a first portion of a bone structure relative to a second portion of the bone structure when moved from a collapsed configuration to an expanded configuration;
an elongate assembly including:
a shaft defining a lumen; and
an elongated member rotatably disposed within the lumen of the shaft; and
an actuator coupled to a proximal end portion of the shaft, the actuator having a first component and a second component and operable to control twisting of the expandable member about the longitudinal axis of the elongated member, the actuator having a first position in which the first and second components remain engaged with each other to allow twisting of the expandable member about the longitudinal axis of the elongated member in a first direction and prevent twisting of the expandable member about the longitudinal axis of the elongated member in an opposing second direction, the actuator having a second position in which the first and second components are separated from each other to allow twisting of the expandable member about the elongated member in both the first and second directions,
a proximal end portion of the expandable member being coupled to a distal end portion of the shaft such that the proximal end portion of the expandable member does not rotate relative to the distal end portion of the shaft when at least a portion of the expandable member is twisted about the elongated member through at least four revolutions,
a distal end portion of the expandable member being coupled to a distal end portion of the elongated member such that the distal end portion of the expandable member does not rotate relative to the distal end portion of the elongated member when at least the portion of the expandable member is twisted about the elongated member through at least four revolutions.

2. The apparatus of claim 1, wherein the elongate assembly is a catheter assembly configured to be inserted percutaneously into a body.

3. The apparatus of claim 1, wherein:
the elongate assembly is a catheter assembly configured to be inserted percutaneously into a body via a cannula defining a lumen having a size; and
the expandable member has an insertion configuration in which a size of the expandable member is less than the size of the lumen defined by the cannula, the portion of the expandable member being twisted about the elongated member through at least four revolutions when the expandable member is in the insertion configuration.

4. The apparatus of claim 1, wherein the expandable member has a rated burst pressure of at least 1.4 Megapascals.

5. The apparatus of claim 1, wherein:
the distal end portion of the expandable member is coupled to the distal end portion of the elongated member such that a hermetic seal is maintained between the distal end portion of the expandable member and the distal end portion of the elongated member when at least the portion of the expandable member is twisted about the elongated member through at least four revolutions; and
the proximal end portion of the expandable member is coupled to the distal end portion of the shaft such that a hermetic seal is maintained between the proximal end portion of the expandable member and the distal end portion of the shaft when at least the portion of the expandable member is twisted about the elongated member through at least four revolutions.

6. The apparatus of claim 1, wherein:
the distal end portion of the expandable member is coupled to the distal end portion of the elongated member such that a hermetic seal is maintained between the distal end portion of the expandable member and the distal end portion of the elongated member when at least the portion of the expandable member is twisted about the elongated member through at least six revolutions; and
the proximal end portion of the expandable member is coupled to the distal end portion of the shaft such that a hermetic seal is maintained between the proximal end portion of the expandable member and the distal end portion of the shaft when at least the portion of the expandable member is twisted about the elongated member through at least six revolutions.

7. The apparatus of claim 1, wherein the distal end portion of the expandable member is bonded to the distal end portion of the elongated member for a length along a longitudinal axis of the elongated member less than approximately 3 millimeters.

8. The apparatus of claim 1, wherein the distal end portion of the expandable member is bonded to the distal end portion of the elongated member for a length along a longitudinal axis of the elongated member less than approximately 2 millimeters.

9. The apparatus of claim 1, wherein the proximal end portion of the expandable member is bonded to the distal end portion of the shaft such for a length along a longitudinal axis of the shaft less than 7 millimeters.

10. The apparatus of claim 1, wherein the distal end portion of the expandable member is bonded to the distal end portion of the elongated member using a thermal bonding process and a laser bonding process.

11. The apparatus of claim 1, wherein the expandable member has a wall thickness of at least 0.1 millimeters and a size along an axis substantially normal to the longitudinal axis of the elongated member of at least 8 millimeters when in an expanded configuration.

12. The apparatus of claim 1, wherein:
the shaft is configured to have an angle of twist between a proximal end portion of the shaft and the distal end portion of the shaft of less than three hundred sixty degrees when at least the portion of the expandable member is twisted about the longitudinal axis of the elongated member through four revolutions.

13. The apparatus of claim 1, wherein:
the shaft is constructed from a composite polymer including nano-particle fillers; and
the shaft is configured to have an angle of twist between a proximal end portion of the shaft and the distal end portion of the shaft of less than one hundred eighty degrees when at least the portion of the expandable member is twisted about the longitudinal axis of the elongated member through four revolutions.

14. The apparatus of claim 1, wherein:
the elongated member is configured to have an angle of twist between a proximal end portion of the elongated member and the distal end portion of the elongated member of less than three hundred sixty degrees when at least the portion of the expandable member is twisted about the longitudinal axis of the elongated member through four revolutions.

15. The apparatus of claim 1, wherein:
the elongated member includes a stylet, at least a portion of the stylet being bonded to the elongated member; and
the stylet is configured to have an angle of twist between a proximal end portion of the stylet and the distal end portion of the elongated member of less than one hundred eighty degrees when at least the portion of the expandable member is twisted about the longitudinal axis of the elongated member through four revolutions.

16. The apparatus of claim 1, further comprising a sleeve disposed between an outer surface of the elongated member and an inner surface of the expandable member, the sleeve, the distal end portion of the expandable member and the distal end portion of the elongated member collectively coupled.

17. The apparatus of claim 1, further comprising a sleeve disposed between an outer surface of the elongated member and an inner surface of the expandable member, the sleeve, the distal end portion of the expandable member and the distal end portion of the elongated member collectively coupled, the sleeve including a colorant.

18. An apparatus, comprising:
an expandable member configured to displace a first portion of a bone structure relative to a second portion of the bone structure when moved from a collapsed configuration to an expanded configuration;
a shaft having a distal end portion coupled to a proximal end portion of the expandable member;
an elongated member rotatably disposed within the shaft, a distal end portion of the elongated member coupled to a distal end portion of the expandable member; and
an actuator coupled to the shaft and having a first component and a second component operable to control twisting of the expandable member about the elongated member, the actuator having a first configuration in which the first and second components remain engaged with each other to allow one of clockwise twisting and counter-clockwise twisting of the expandable member about the elongated member while preventing the other of clockwise twisting and counter-clockwise twisting of the expandable member about the elongated member and a second configuration in which the first and second components are separated from each other to allow clockwise twisting and counter-clockwise twisting of the expandable member about the elongated member,
the shaft configured to have an angle of twist between a proximal end portion of the shaft and the distal end portion of the shaft of less than one hundred eighty degrees when at least a portion of the elongated member is rotated relative to the shaft through at least four revolutions.

19. The apparatus of claim 18, wherein the shaft is constructed from a composite polymer including nano-particle fillers.

20. The apparatus of claim 18, wherein:
the elongated member is configured to have an angle of twist between a proximal end portion of the elongated member and the distal end portion of the elongated member of less than one hundred eighty degrees when at least the portion of the elongated member is rotated relative to the shaft through at least four revolutions.

21. The apparatus of claim 18, wherein:
the elongated member includes a stylet disposed therein, a portion of the stylet being bonded to the elongated member; and
the stylet is configured to have an angle of twist between a proximal end portion of the stylet and the distal end portion of the elongated member of less than one hundred eighty degrees when at least the portion of the elongated member is rotated relative to the shaft through at least four revolutions.

22. The apparatus of claim 18, wherein:
the elongated member is constructed from a composite polymer including nano-particle fillers; and
the elongated member is configured to have an angle of twist between a proximal end portion of the elongated member and the distal end portion of the elongated member of less than one hundred eighty degrees when at least the portion of the elongated member is rotated relative to the shaft through at least four revolutions.

23. The apparatus of claim 18, wherein the distal end portion of the expandable member is bonded to the distal end portion of the elongated member such that a hermetic seal is maintained between the distal end portion of the expandable member and the distal end portion of the elongated member when at least a portion of the expandable member is twisted about the elongated member through at least four revolutions.

24. The apparatus of claim 18, wherein the proximal end portion of the expandable member is coupled to the distal end portion of the shaft such that a hermetic seal is maintained between the proximal end portion of the expandable member and the distal end portion of the shaft when at least a portion of the expandable member is twisted about the elongated member through at least four revolutions.

\* \* \* \* \*